United States Patent [19]

Nason et al.

[11] Patent Number: 4,850,817
[45] Date of Patent: Jul. 25, 1989

[54] MECHANICAL DRIVE SYSTEM FOR A MEDICATION INFUSION SYSTEM

[75] Inventors: Clyde K. Nason, Valencia; John P. Pelmulder, Chatsworth, both of Calif.

[73] Assignee: Pacesetter Infusion, Ltd., Sylmar, Calif.

[21] Appl. No.: 127,133

[22] Filed: Dec. 1, 1987

[51] Int. Cl.⁴ .............................................. F04B 9/04
[52] U.S. Cl. .................................... 417/362; 417/479; 417/510
[58] Field of Search ............... 417/63, 360, 362, 410, 417/415, 479, 510; 604/65–67, 151–155; 128/DIG. 12, DIG. 13

[56] References Cited

U.S. PATENT DOCUMENTS

| | | | |
|---|---|---|---|
| 3,463,094 | 8/1969 | Fonda | 417/63 X |
| 3,606,596 | 4/1970 | Edwards | 417/479 |
| 4,236,880 | 12/1980 | Archibald | 417/479 X |
| 4,273,121 | 6/1981 | Jassawalla | 417/479 X |
| 4,277,226 | 7/1981 | Archibald | 417/63 X |
| 4,303,376 | 12/1981 | Siekmann | 417/479 X |
| 4,326,837 | 4/1982 | Gilson et al. | 417/63 X |
| 4,382,753 | 5/1983 | Archibald | 417/479 |
| 4,468,222 | 8/1984 | Lundquist | 417/360 X |
| 4,470,758 | 9/1984 | Pazerenas et al. | 417/63 |
| 4,479,797 | 10/1984 | Kabayashi et al. | 417/510 X |
| 4,559,038 | 12/1985 | Berg et al. | 417/510 X |

Primary Examiner—Carlton R. Croyle
Assistant Examiner—Eugene L. Szczecina, Jr.
Attorney, Agent, or Firm—Leslie S. Miller

[57] ABSTRACT

A mechanical drive system for use in driving a disposable cassette containing a reciprocating fluid pump and active valves from a main pump unit is disclosed which utilizes a single power module cam to drive both the reciprocating pump and the valves. By using a unitary power module cam, the system completely eliminates the possibility of a timing error between the operation of the reciprocating pump and the valves. A one-way clutch is used to prevent the system from slipping into a reverse operation, and the operation of the valve actuators prevents the possibility of free flow through a cassette installed onto the main pump unit.

19 Claims, 18 Drawing Sheets

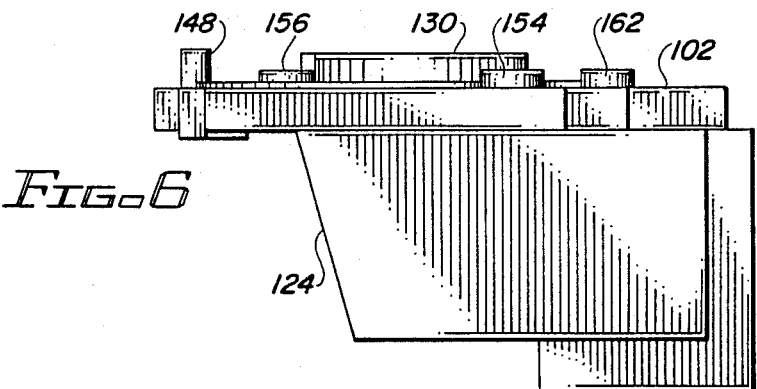
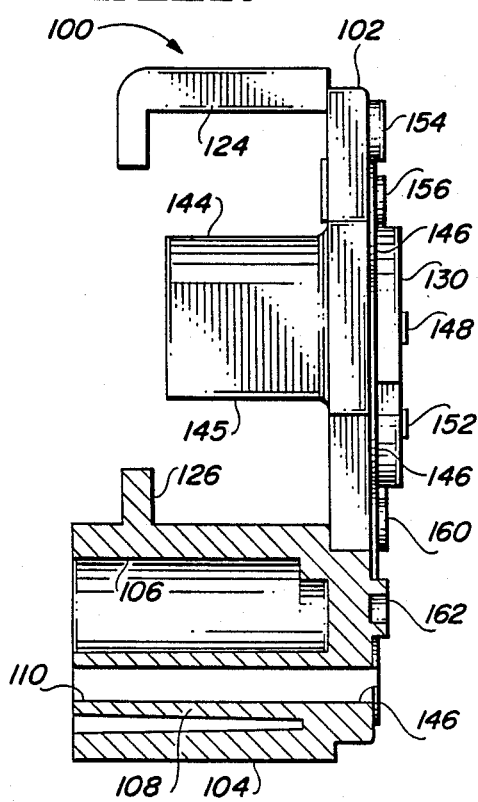
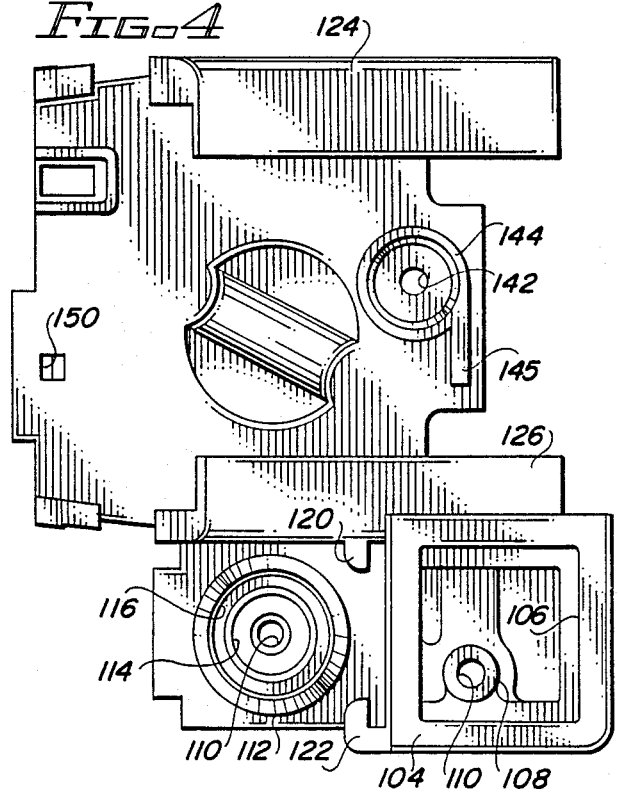
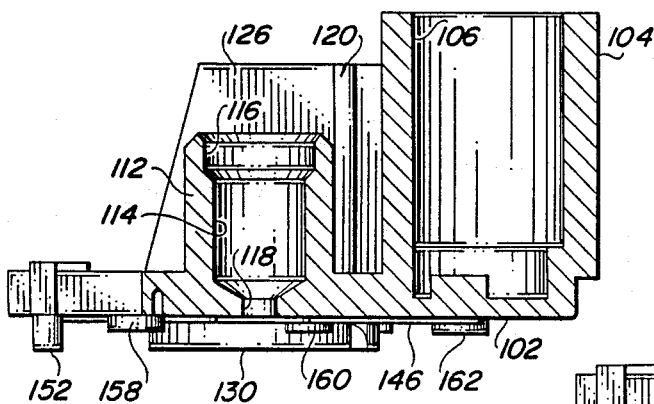
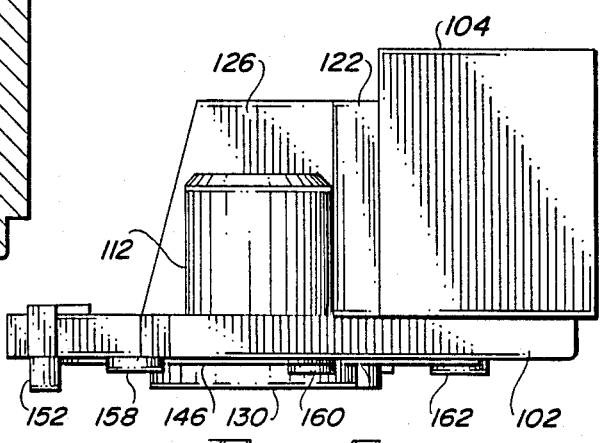

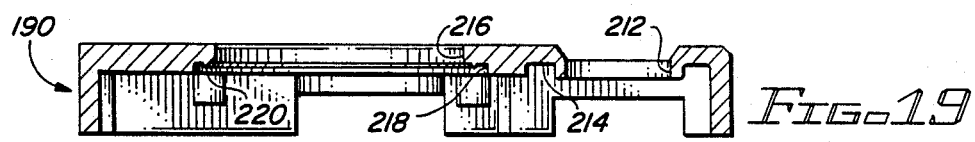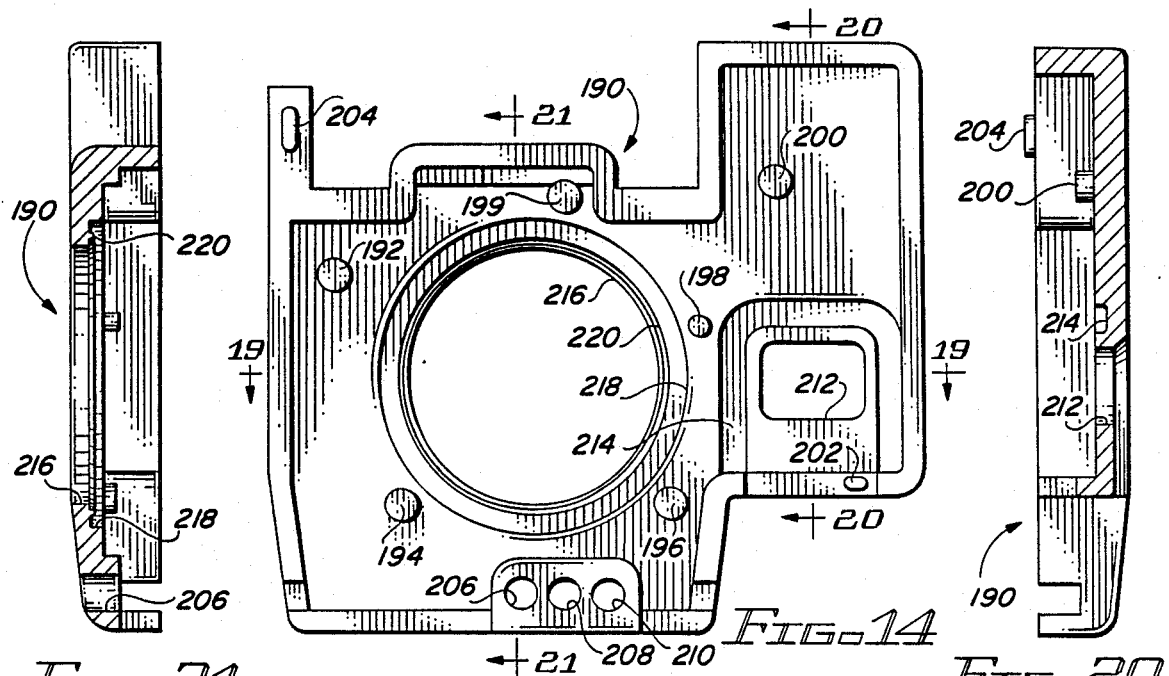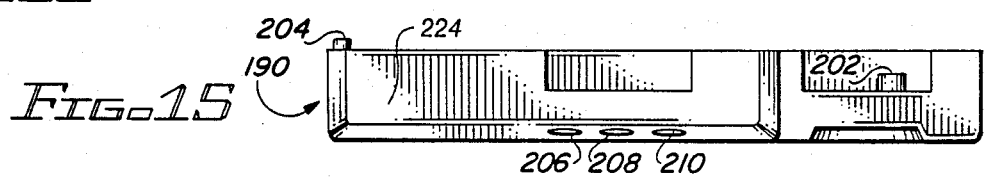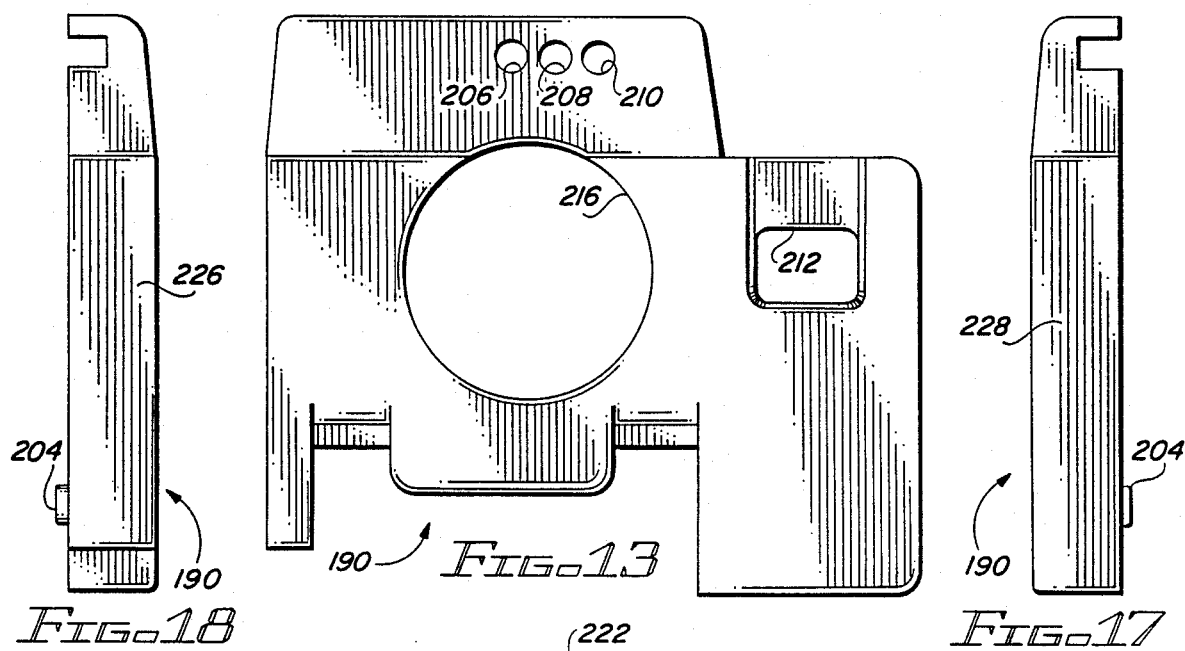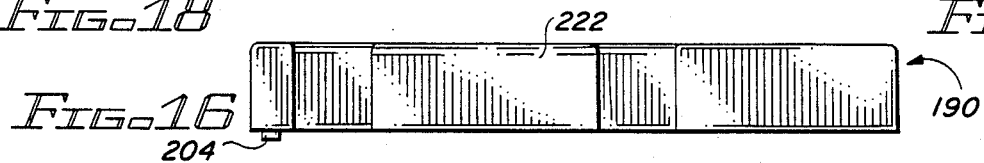

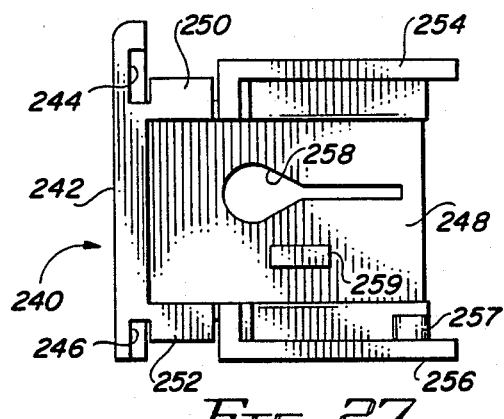
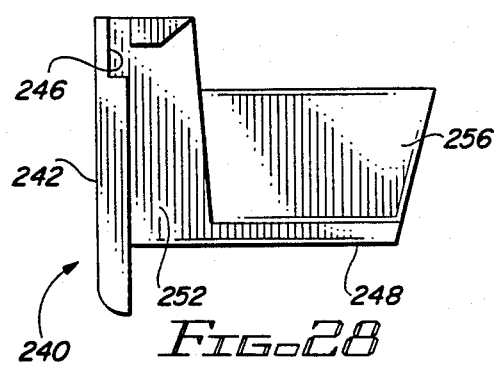
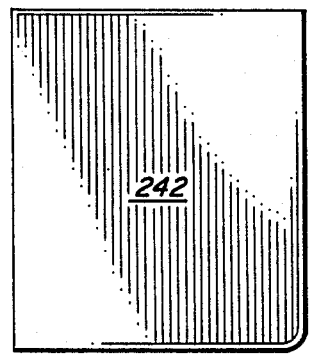
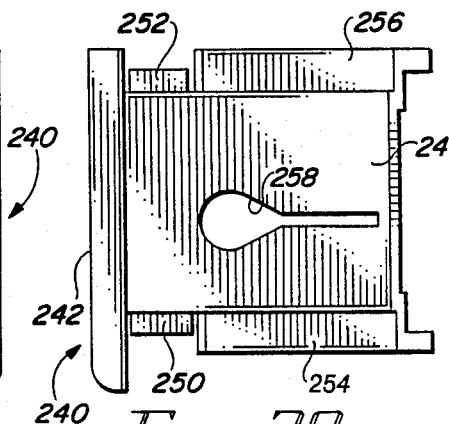
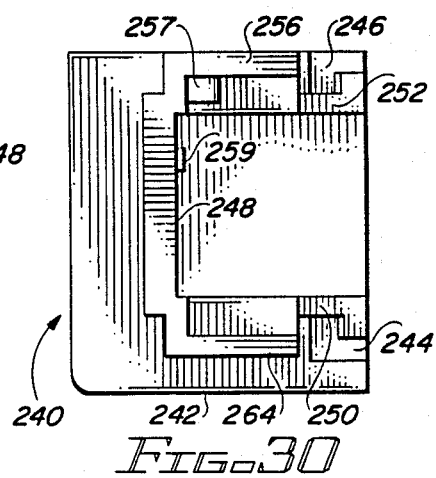
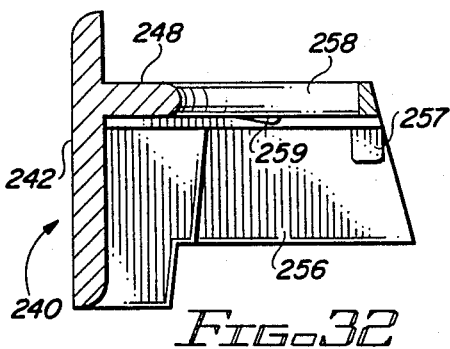
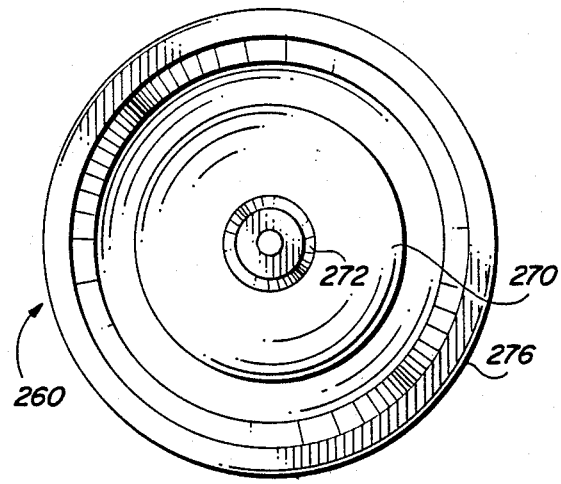
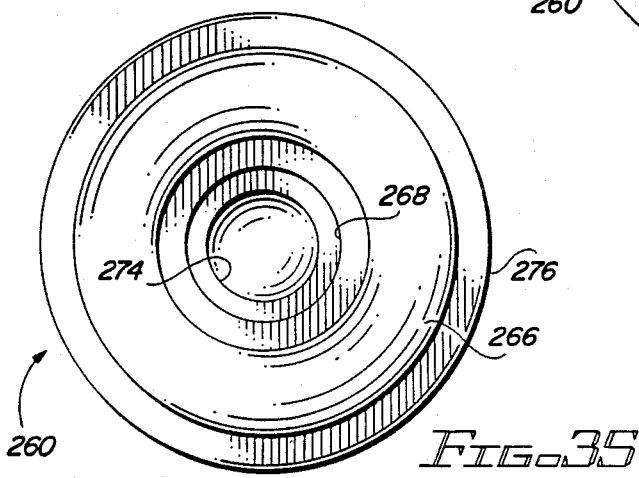

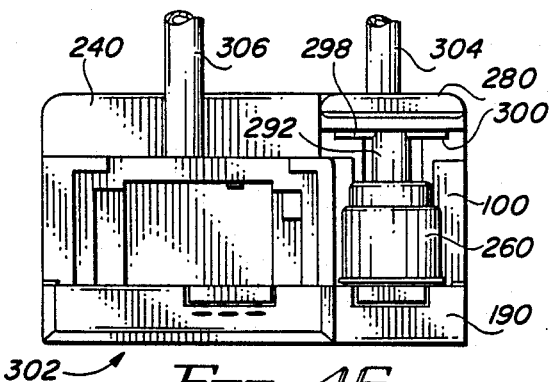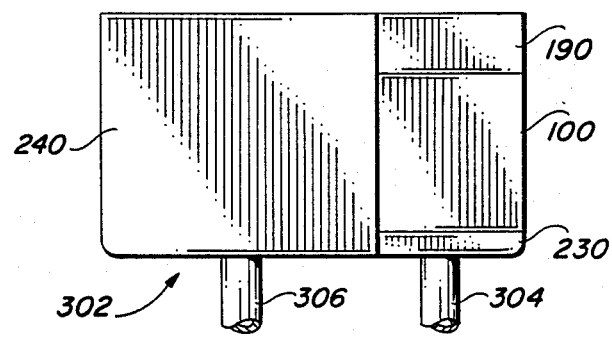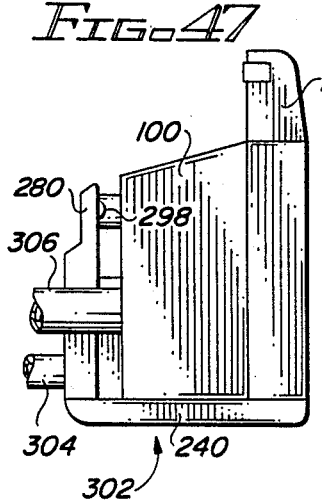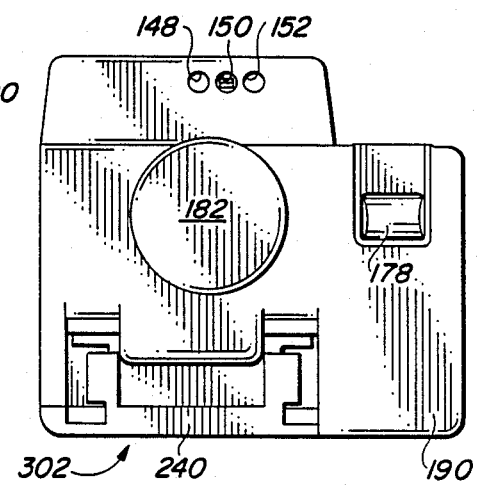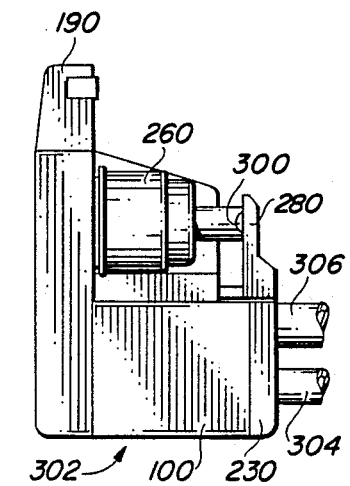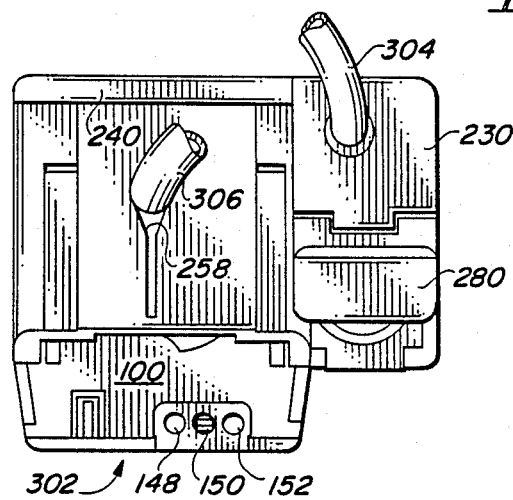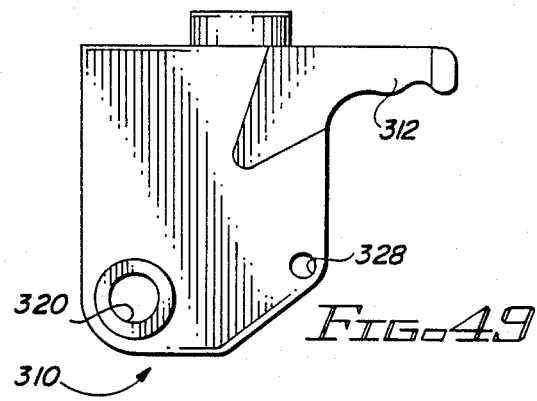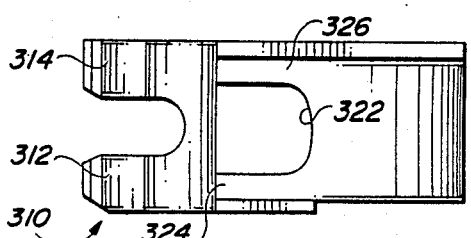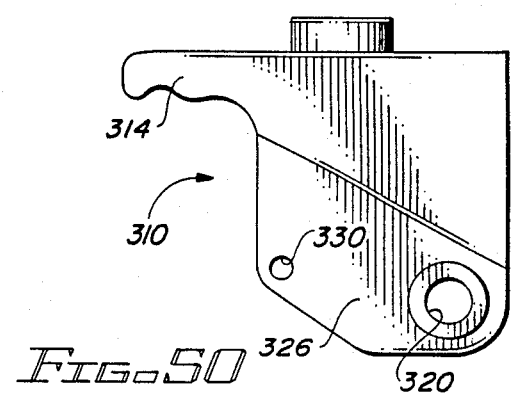

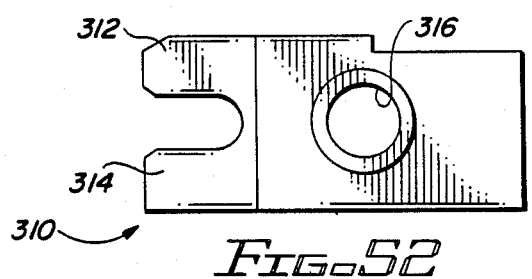
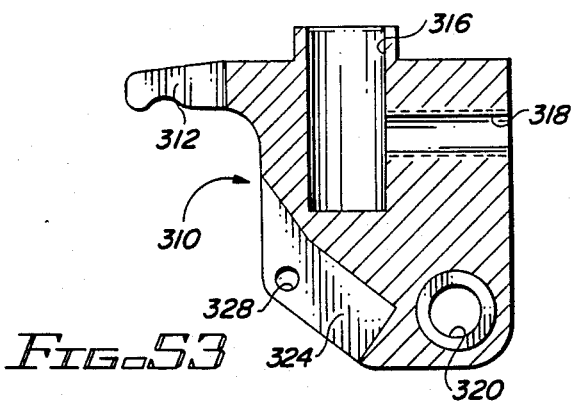
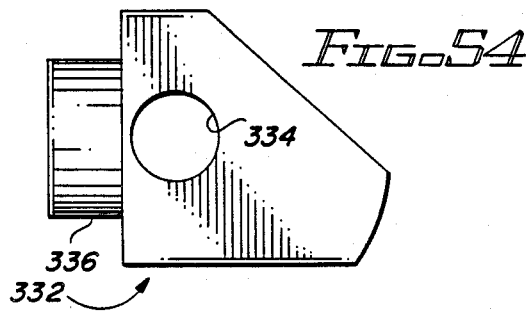
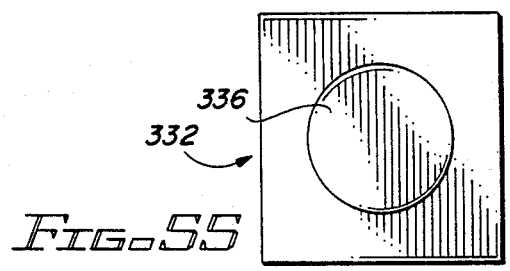
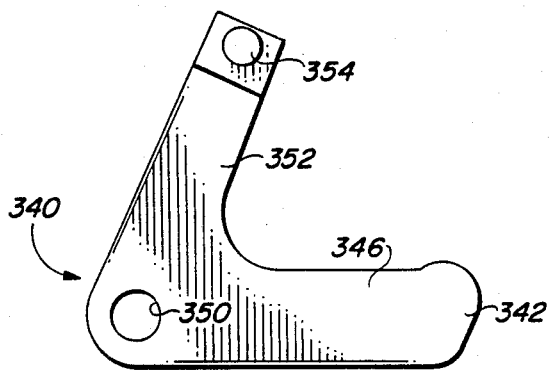
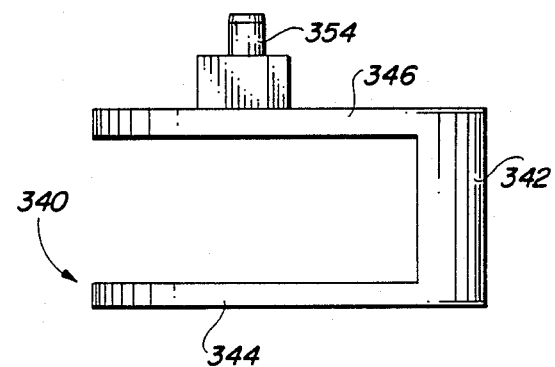
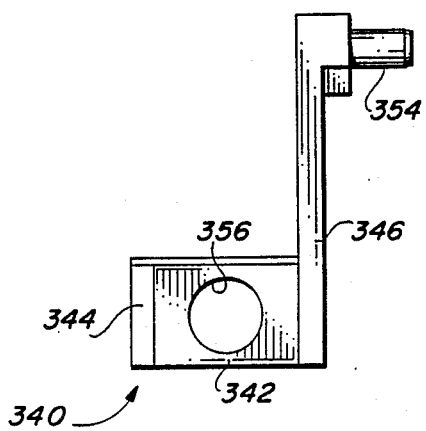
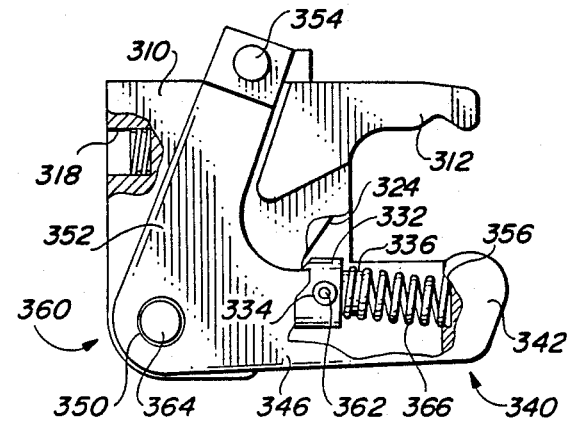

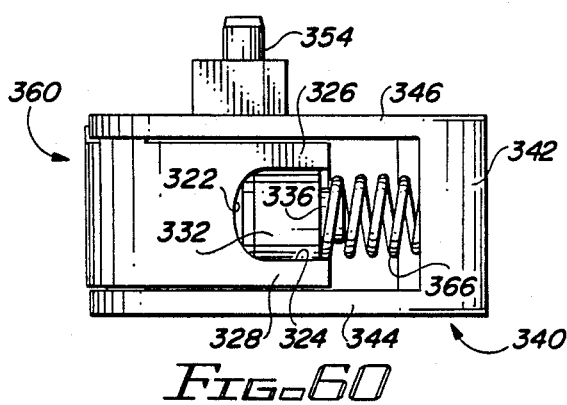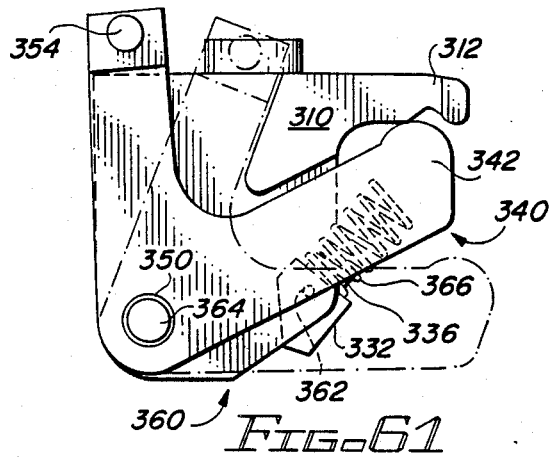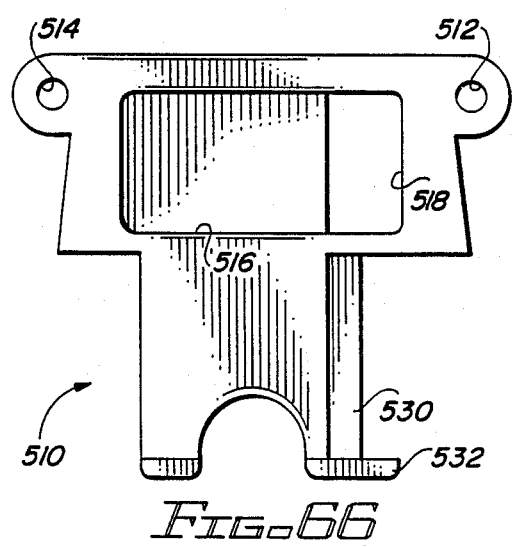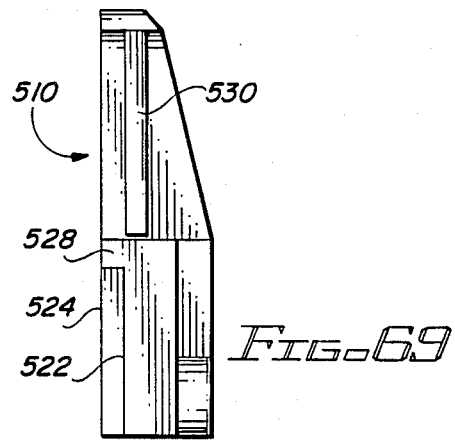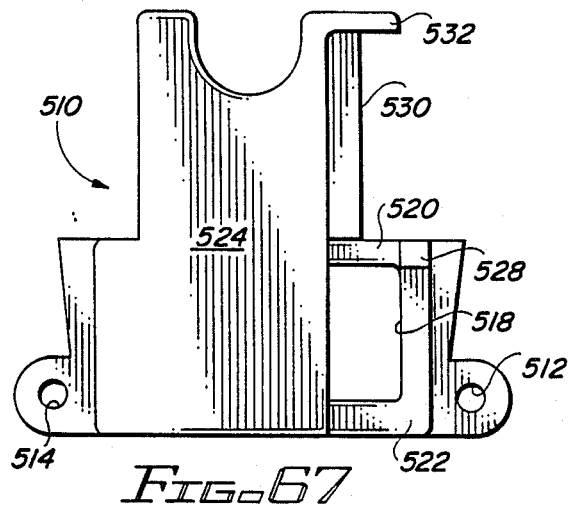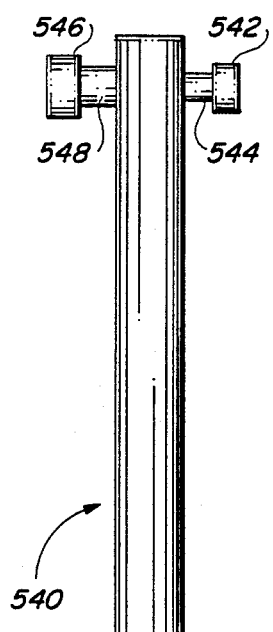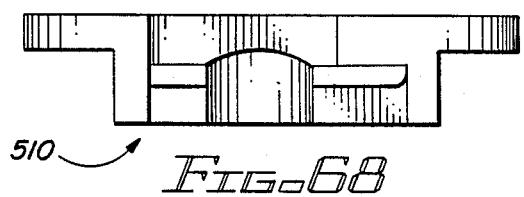

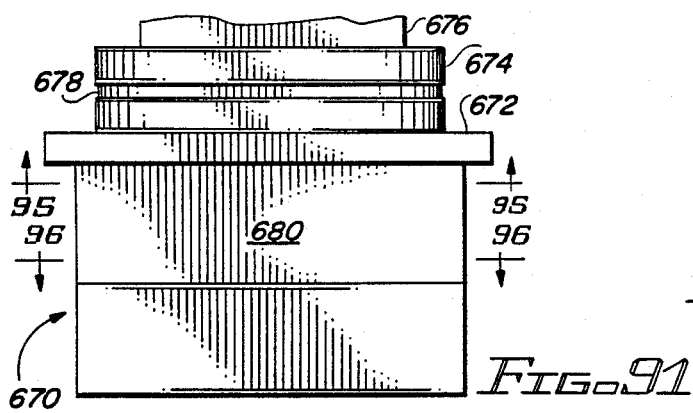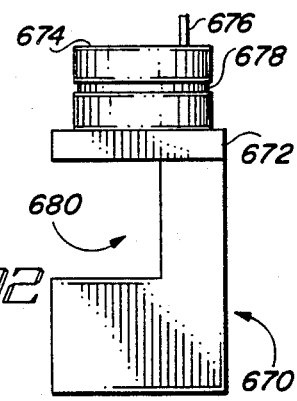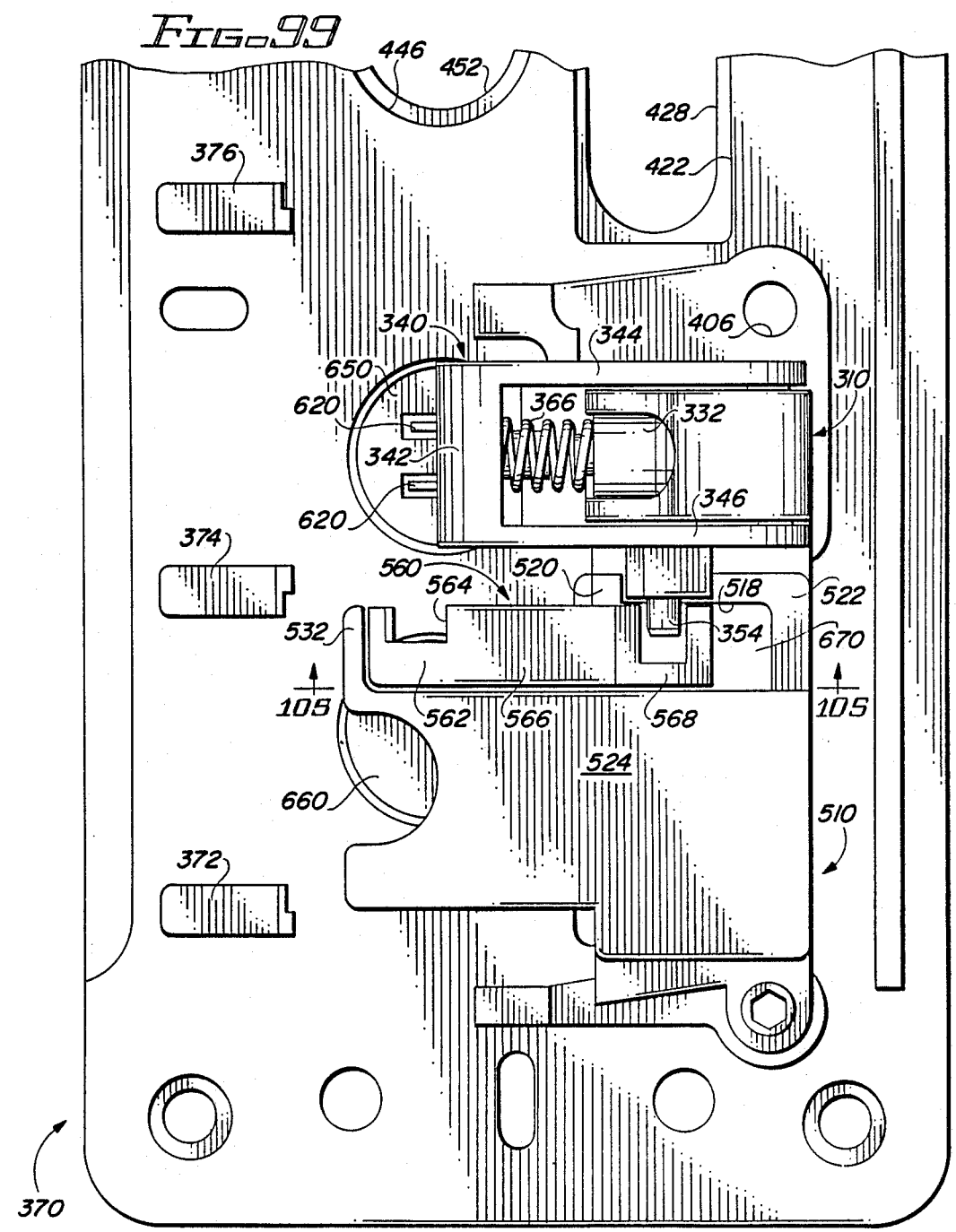

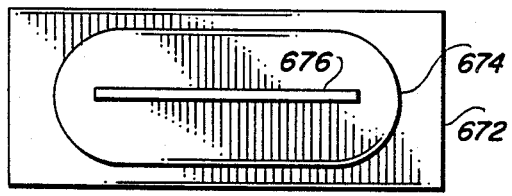
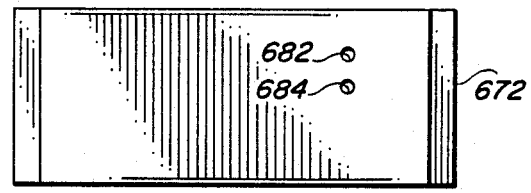
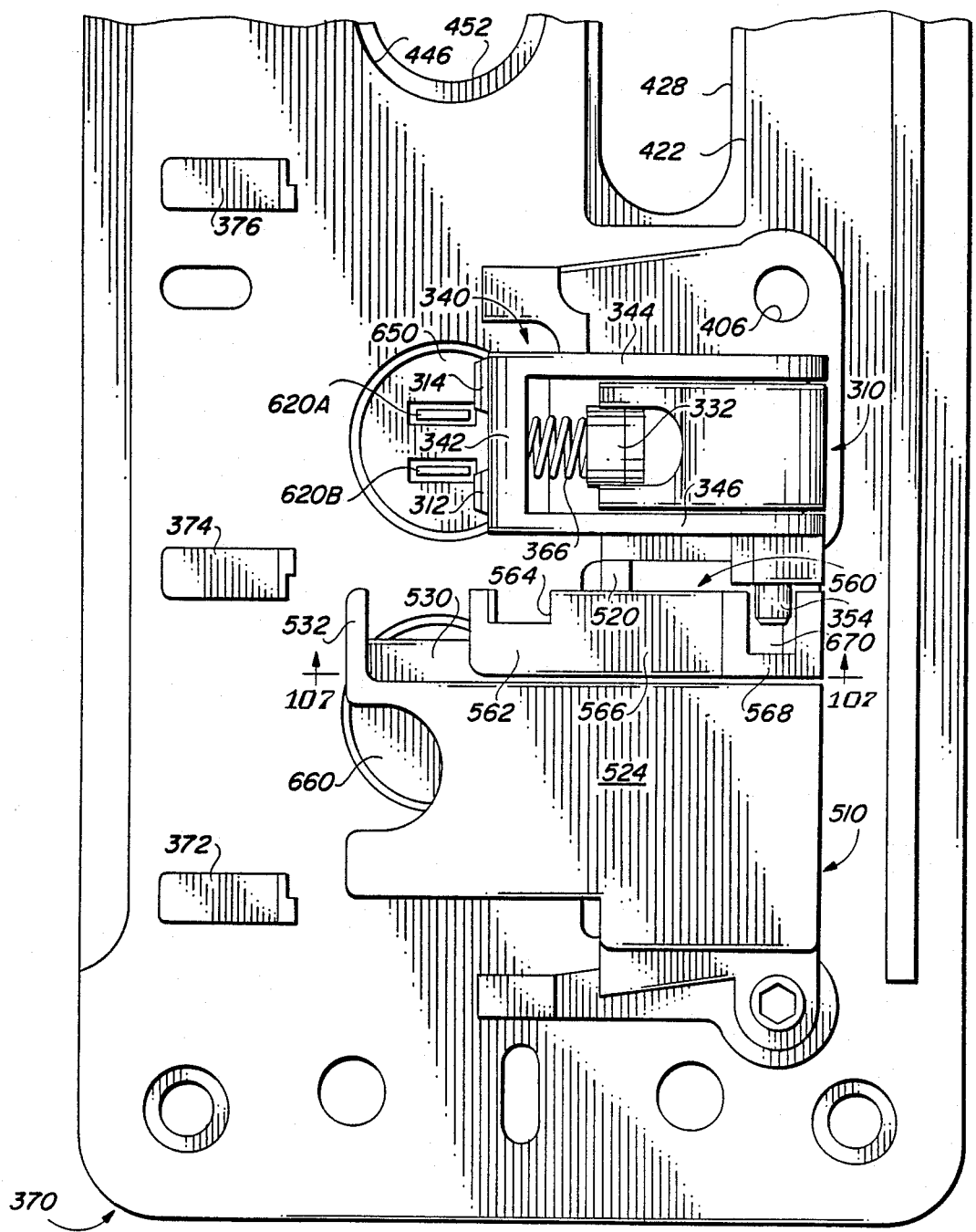

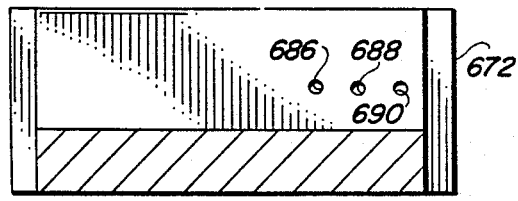
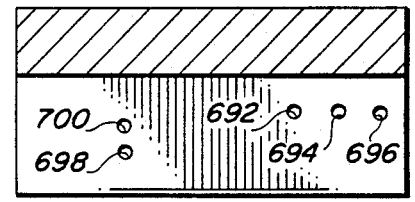
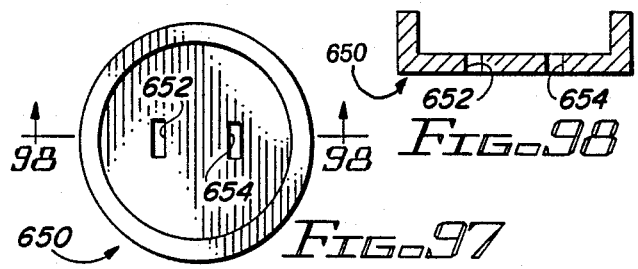
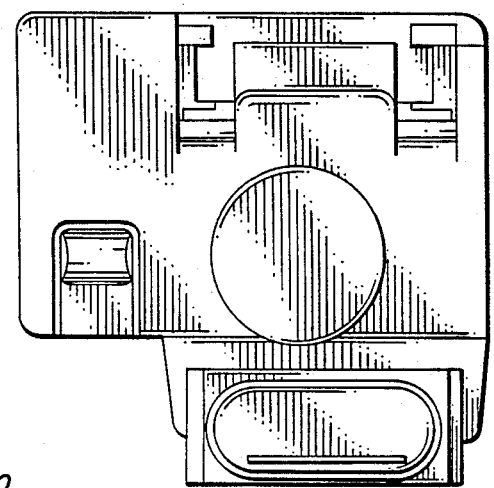
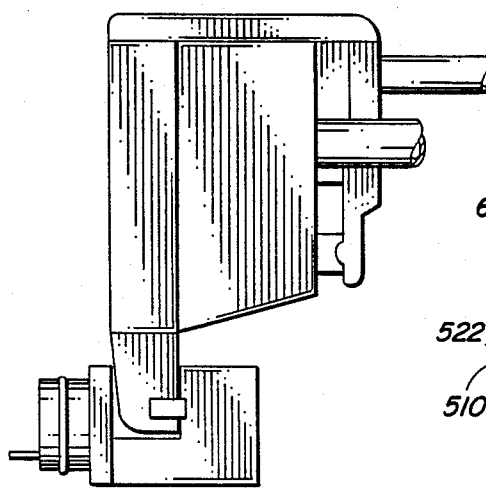
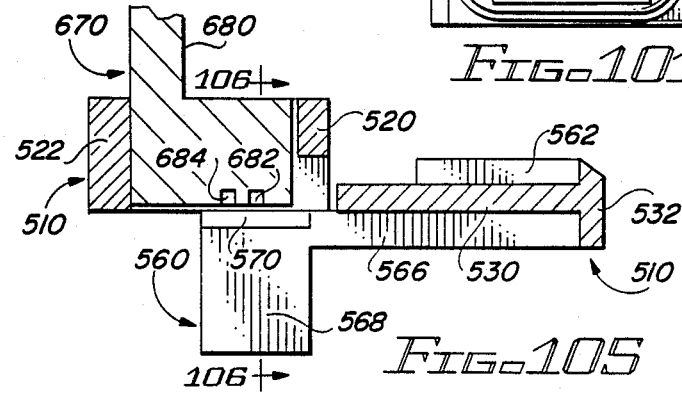
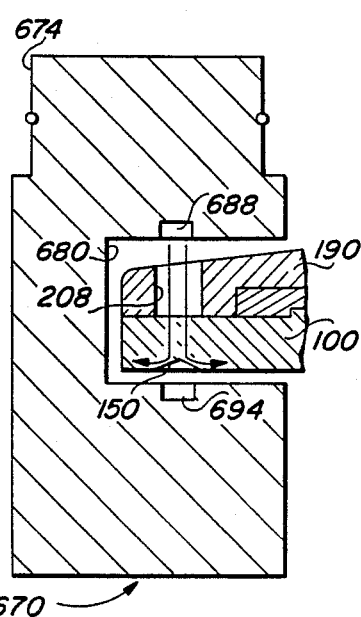
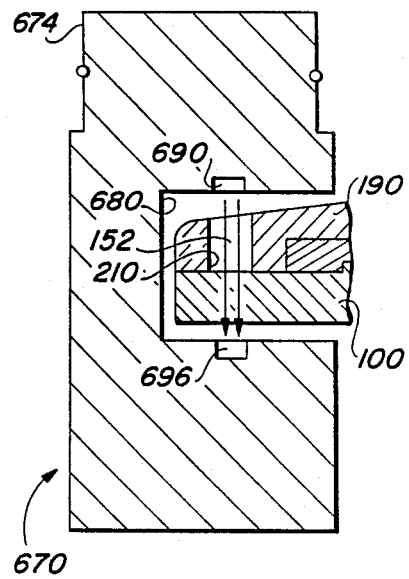
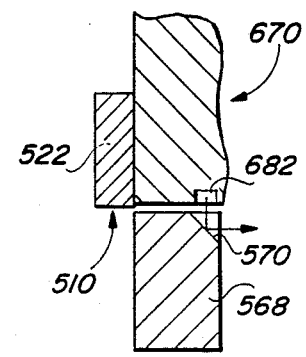

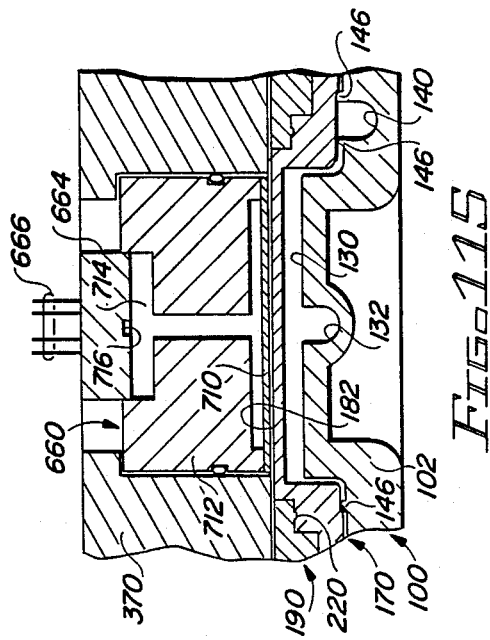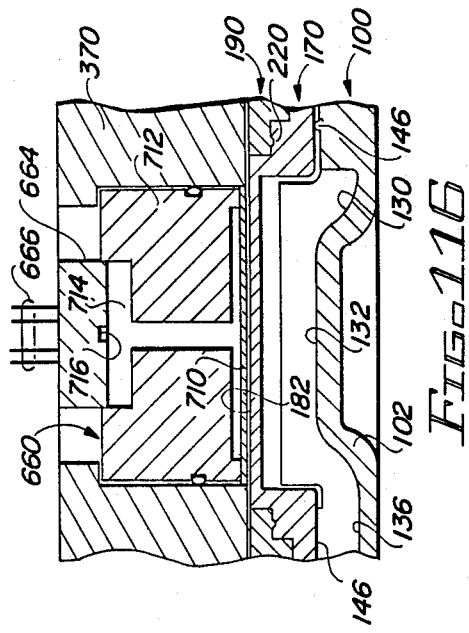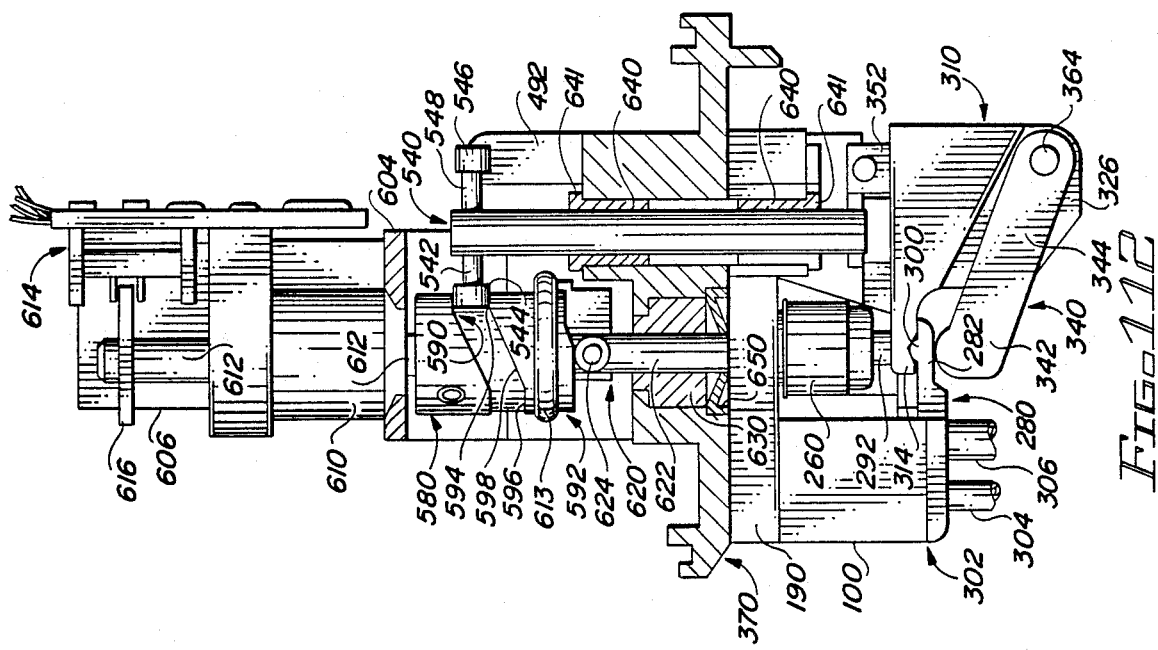

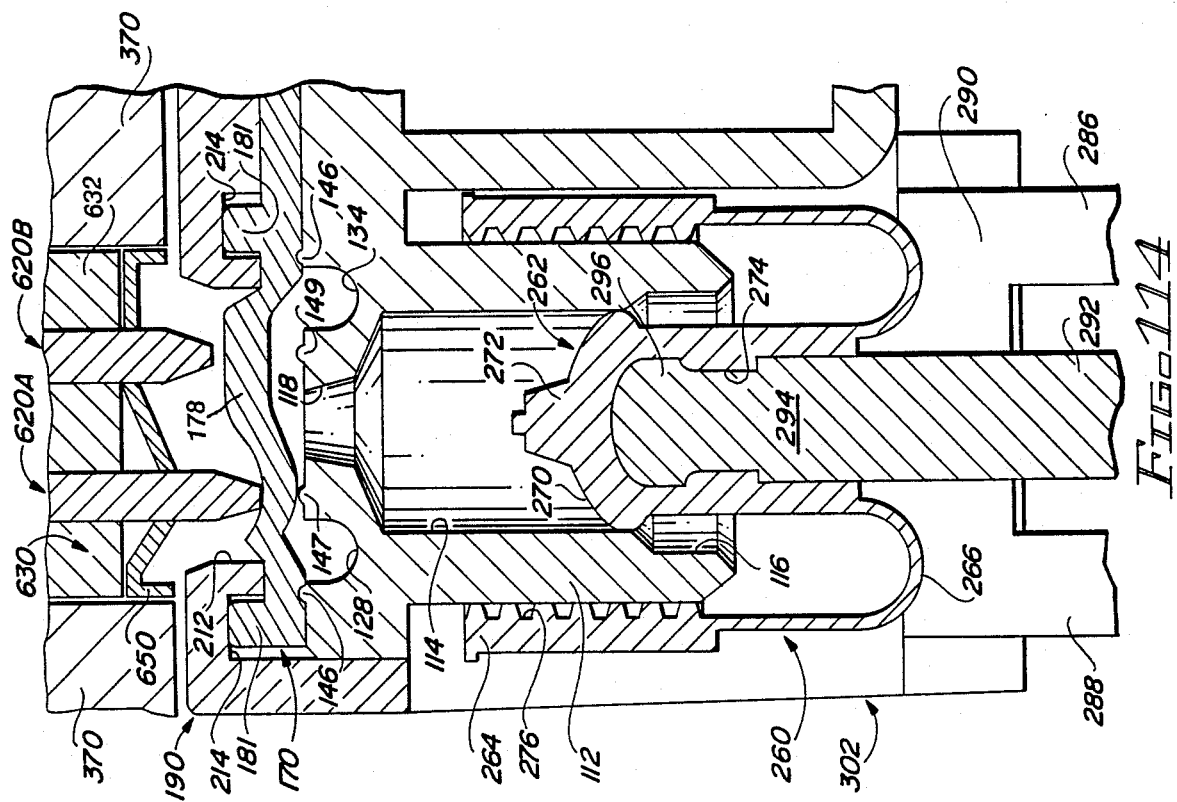
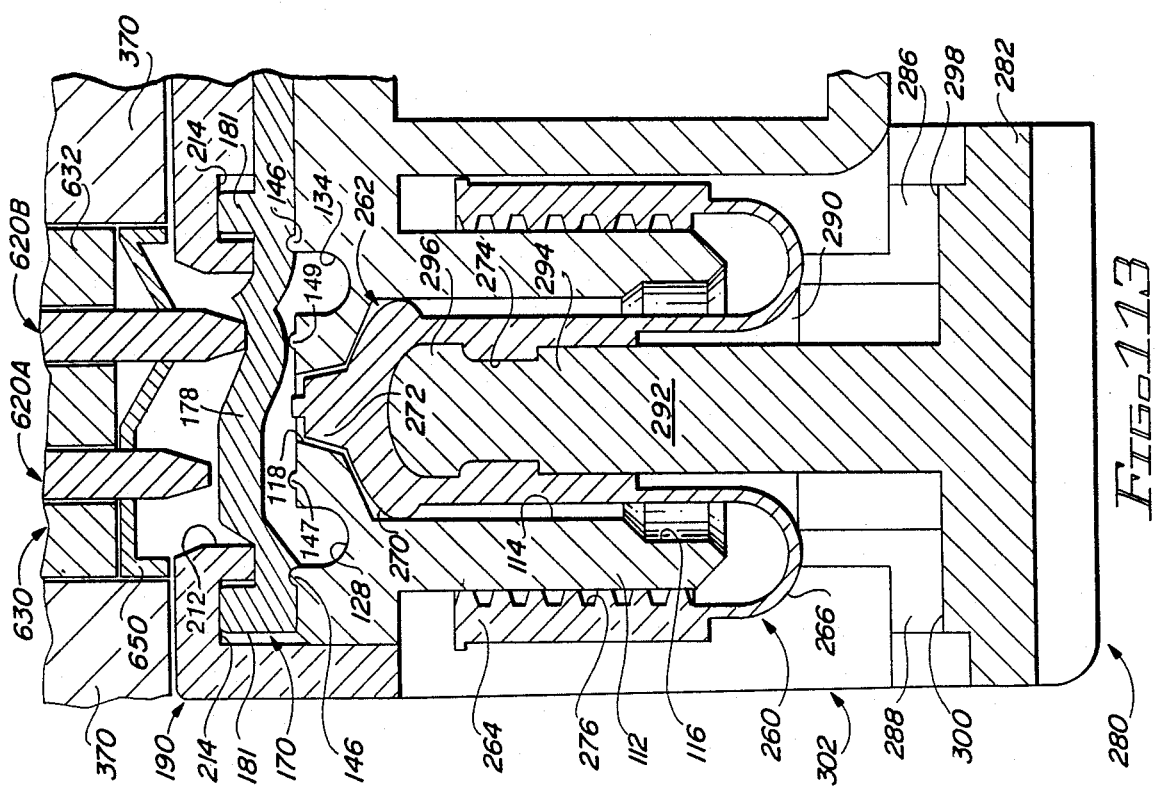

MECHANICAL DRIVE SYSTEM FOR A MEDICATION INFUSION SYSTEM

IDENTIFICATION OF RELATED PATENT APPLICATIONS

This application is related to six other concurrently filed copending patent applications. These patent applications are U.S. Ser. No. 127,333, entitled "Disposable Cassette for a Medication Infusion System," U.S. Ser. No. 127,350, entitled "Piston Cap and Boot Seal for a Medication Infusion System," U.S. Ser. No. 128,122, entitled "Pressure Diaphragm for a Medication Infusion System," U.S. Ser. No. 128,009, entitled "Cassette Optical Identification Apparatus for a Medication Infusion System," U.S. Ser. No. 128,121, entitled "Air-In-Line Detector for a Medication Infusion System," and U.S. Ser. No. 127,359, entitled "Cassette Loading and Latching Apparatus for a Medication Infusion System."

BACKGROUND OF THE INVENTION

Field of the Invention

The present invention relates generally to an electromechanical drive system for a medication infusion system, and more particularly to a medication infusion system having a disposable cassette containing a fluid pump and active valves which cassette is mounted on and driven by a main pump unit which includes a prime mover and a drive mechanism, the drive mechanism using a single power module cam to drive both the pump and the valves.

In the past there have been two primary techniques which have been used to deliver drugs which may not be orally ingested to a patient. The first such technique is through an injection, or shot, using a syringe and needle which delivers a large dosage at relatively infrequent intervals to the patient. This technique is not always satisfactory, particularly when the drug being administered is potentially lethal, has negative side effects when delivered in a large dosage, or must be delivered more or less continuously to achieve the desired therapeutic effect. This problem results in small injections being given at more frequent intervals, a compromise approach not yielding satisfactory results.

Alternatively, the second technique involves administering a continuous flow of medication to the patient, typically through an IV bottle. Medication may also be delivered through an IV system with an injection being made into a complex maze of IV tubes, hoses, and other paraphernalia. With drop counters being used to meter the amount of bulk fluid delivered, many medications still end up being administered in a large dosage through an injection into the IV lines, although the medications may be diluted somewhat by the bulk fluid.

As an alternative to these two techniques of administering medication to a patient, the relatively recent addition of medication infusion pumps has come as a welcome improvement. Medication infusion pums are utilized to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained more precisely by operating on a continuous time basis.

One of the requirements of a medication infusion system is dictated by the important design consideration of disposability. Since the portion of the device through which medication is pumped must be sterile, in most applications of modern medication infusion equipment some portions of the equipment are used only once and then disposed of, typically at regular intervals such as once daily. It is therefore desirable that the fluid pump portion of the infusion pump device be disposable, with the fluid pump being designed as an attachable cassette which is of inexpensive design, and which is easily installable onto the main pump unit.

It will be perceived that it is desirable to have a simple disposable cassette design to minimize the cost of construction of the cassette, using the minimum number of parts necessary in the design of the cassette. The design of the cassette must be mass producible, and yet result in a uniform cassette which is capable of delivering liquid medication or other therapeutic fluids with a high degree of accuracy. The cassette should include therein more than just a fluid pump; other features which has formerly been included in peripheral devices may be included in the cassette.

It is therefore the primary objective of the present invention to provide a drive system in a main pump unit for driving a reciprocating fluid pump having active inlet and outlet valves, the pump and valves being contained in the disposable cassette. The system must be highly sophisticated while mechanically uncomplex and inherently reliable. Specifically, the drive system of the present invention shall be capable of driving a pump with a high degree of precision and accuracy, with the degree of precision remaining constant throughout the extended operating life of the main pump unit.

Several other additional features are desirable in the design of a cassette and a main pump unit making up an infusion system. Such features include a simple and uncomplicated installation of the cassette onto the main pump unit, and a wide range in the volume which may be pumped by the system over a particular period of time. It is an objective of the present invention that the valves and the pump be incapable of being operated out of synchrony, and it that they always be properly synchronized. Another objective of the present invention is to prevent free flow of fluid through an installed cassette. Still another objective of the present invention is that the valves in the cassette be placed in position to be driven by the drive system by merely installing the cassette with the valves in proximity to the drive mechanism. In addition, the drive system must be capable of varying output over a broad range while retaining a high degree of accuracy across the complete range of delivery rates. No system currently known in the art has satisfactorily accomplished all of these objectives.

Despite the inclusion of more features than contained in any competing design, both the main pump unit and the cassette of the present invention shall utilize a minimum number of parts, all of the parts are of inexpensive construction yet which afford the assembled cassette the high degree of accuracy which must be retained. The system of the present invention must have other advantages necessary to compete effectively against known competing designs. The system must provide an ease of use rivaling the best of such competing systems. It must accomplish all these objects in a manner which will retain all of the advantages of reliability, durability, and safety of operation. The drive system of the present invention must provide all of these advantages and overcome the limitations of the background art without incurring any relative disadvantage. All the advantages of the present invention will result in a superior medication infusion system having a number of advantages making the system a highly desirable alternative to systems presently available.

SUMMARY OF THE INVENTION

The disadvantages and limitations of the background art discussed above are overcome by the present invention. With this invention, a disposable cassette having only seven components therein is described. The cassette utilizes a highly accurate and reliable piston-type fluid pump and an active valve design of unparalleled accuracy, simplicity, and accuracy of operation. A bubble trap is included in the cassette for removing air bubbles introduced into the system, and a bubble detector is used to ensure that fluid supplied to a patient is virtually bubble-free.

In the preferred embodiment of the present invention, the cassette includes a pressure diaphragm for enabling pressure sensing of the outlet line. The pressure diaphragm is integrated into the design of the cassette, and includes a circular raised pressure plateau on the cassette housing. The fluid channel on the outlet side of the fluid pump in the cassette leads to one side of the pressure plateau, and a fluid outlet leads from the other side of the pressure plateau.

The present invention utilizes a drive system having a DC motor driving a gear reduction unit, the output of which is used to drive a power module cam. The power module cam is mounted for rotation in a single direction only, thereby preventing reverse direction operation of the pump and valves. The power module cam itself has a groove therein which moves in longitudinal position on the power module cam as it is turned, and this groove is used to drive the reciprocal pump contained in the disposable cassette which is attached to the main pump unit.

The power module cam is mounted with one end facing the valves in the disposable cassette. On this end of the power module cam is located a cam surface around the outer edge of the end of the power module cam. The cam surface varies in height, and by mounting valve actuators between the cam surface and the valves in the cassette, the cam surface will operate the valves in the cassette. Since both the groove driving the pump and the cam surface driving the valves are located on a single, unitary power module cam, the pump and the valves will always be timed correctly with respect to each other.

The present invention therefore provides a drive system in a main pump unit which drives a reciprocating fluid pump having active inlet and outlet valves, with the pump and valves being contained in the disposable cassette. The system is highly sophisticated while mechanically uncomplex and inherently reliable. The drive system of the present invention is capable of driving a pump with a high degree of precision and accuracy, with the degree of precision remaining constant throughout the extended operating life of the main pump unit.

Several other additional features included in the system include a simple and uncomplicated installation of the cassette onto the main pump unit, and a wide range in the volume which may be pumped by the system over a particular period of time. Free flow through an installed cassette is prevented due to the construction and timing of the valve actuators. By the very nature of the present invention, the valves and the pump are incapable of being operated out of synchrony; they are always properly and prefectly synchronized. The valves in the cassette are placed in position to be driven by the drive system by merely installing the cassette with the valves in proximity to the drive mechanism. In addition, the drive system is capable of varying the flow rate over a broad range while retaining a high degree of accuracy across the complete range of delivery rates. No other system currently known in the art has satisfactorily accomplished all of these objectives.

Despite the inclusion of more features than contained in any competing design, both the main pump unit and the cassette of the present invention utilize a minimum number of parts, all of which parts are of inexpensive construction yet which afford the assembled cassette the high degree of accuracy which must be retained. The system provides an ease of use rivaling the best of competing systems. It accomplishes all these objects in a manner which retains all of the advantages of reliability, durability, and safety of operation. The drive system of the present invention provides all of these advantages and overcomes the limitations of the background art without incurring any relative disadvantage whatsoever. All the advantages of the present invention result in a superior medication infusion system which has a number of advantages making the system a highly desirable alternative to systems presently available.

DESCRIPTION OF THE DRAWINGS

In the detailed description of the preferred embodiment a uniform directional system is used in which front, back, top, bottom, left, and right are indicated with respect to the operation position of the cassette and main pump unit when viewed from the front of the main pump unit. These and other advantages of the present invention are best understood with reference to the drawings, in which:

FIG. 4 is a bottom view of the cassette body shown in FIGS. 1 through 3;

FIG. 5 is a right side view of the cassette body shown in FIGS. 1 through 4;

FIG. 6 is a left side view of the cassette body shown in FIGS. 1 through 5;

FIG. 7 is a partially cutaway view from the front side of the cassette body shown in FIGS. 1 through 6, showing the bubble trap used to remove air bubbles from the fluid supplied to the cassette;

FIG. 8 is a partially cutaway view from the right side of the cassette body shown in FIGS. 1 through 6, showing the cylinder of the fluid pump contained in the cassette;

FIG. 13 is a top plan view of a valve diaphragm retainer used to retain the valve diaphragm shown in FIGS. 9 through 12;

FIG. 14 is a bottom view of the valve diaphragm retainer shown in FIG. 13;

FIG. 15 is a back side view of the valve diaphragm retainer shown in FIGS. 13 and 14;

FIG. 16 is a front side view of the valve diaphragm retainer shown in FIGS. 13 through 15.

FIG. 17 is a right side view of the valve diaphragm retainer shown in FIGS. 13 through 16;

FIG. 18 is a left side view of the valve diaphragm retainer shown in FIGS. 13 through 17;

FIG. 19 is a cutaway view from the front side of the valve diaphragm retainer shown in FIGS. 13 through 18;

FIG. 20 is a cutaway view from the left side of the valve diaphragm retainer shown in FIGS. 13 through 19;

FIG. 21 is a cutaway view from the right side of the valve diaphragm retainer shown in FIGS. 13 through 20;

FIG. 27 is a top plan view of a slide latch used both to lock the cassette in place on a main pump unit, and to pinch off the IV outlet line prior to installation on the main pump unit;

FIG. 28 is a right side view of the slide latch shown in FIG. 27;

FIG. 29 is a bottom view of the slide latch shown in FIGS. 27 and 28;

FIG. 30 is a back side view of the slide latch shown in FIGS. 27 through 29;

FIG. 31 is a front side view of the slide latch shown in FIGS. 27 through 30;

FIG. 32 is a cutaway view from the left side of the slide latch shown in FIGS. 27 through 31;

FIG. 34 is a top end view of the piston cap and boot seal shown in FIG. 33;

FIG. 35 is a bottom end view of the piston cap and boot seal shown in FIGS. 33 and 34;

FIG. 43 is a top plan view of an assembled cassette using the components shown in FIGS. 1 through 42, with the slide latch in the closed position;

FIG. 44 is a bottom view of the assembled cassette shown in FIG. 43;

FIG. 45 is a front side view of the assembled cassette shown in FIGS. 43 and 44;

FIG. 46 is a back side view of the assembled cassette shown in FIGS. 43 through 45;

FIG. 47 is a left side view of the assembled cassette shown in FIGS. 43 through 46;

FIG. 48 is a right side view of the assembled cassette shown in FIGS. 43 through 47;

FIG. 49 is a left side view of the latch head used to capture and actuate the piston;

FIG. 50 is a right side view of the latch head shown in FIG. 49;

FIG. 51 is a bottom view of the latch head shown in FIGS. 49 and 50;

FIG. 52 is a top view of the latch head shown in FIGS. 49 through 51;

FIG. 53 is a cutaway view from the right side of the latch head shown in FIGS. 49 through 52;

FIG. 54 is a right side view of the spring retainer to be mounted in the latch head shown in FIGS. 49 through 52;

FIG. 55 is a front view of the spring retainer shown in FIG. 54;

FIG. 56 is a left side view of the latch jaw to be mounted on the latch head shown in FIGS. 49 through 52;

FIG. 57 is a bottom view of the latch jaw shown in FIG. 56;

FIG. 58 is a back view of the latch jaw shown in FIGS. 56 and 57;

FIG. 59 is a left side view of the jaws assembly in the open position, the jaws assembly being made up of the latch head shown in FIGS. 49 through 52, the spring retainer shown in FIGS. 54 and 55, the latch jaw shown in FIGS. 56 through 58, a latch spring, and pins used to assemble the various components together;

FIG. 60 is a bottom view of the jaws assembly shown in FIG. 59, with the jaws assembly being shown in the open position;

FIG. 61 is a left side view of the jaws assembly shown in FIGS. 59 and 60, with the jaws assembly being shown in the closed position (and in the open position in phantom lines);

FIG. 66 is a bottom plan view of the cassette guide used to position the cassette of FIGS. 43 through 48 on the main pump unit;

FIG. 67 is a top view of the cassette guide shown in FIG. 66;

FIG. 68 is a front view of the cassette guide shown in FIGS. 66 and 67;

FIG. 69 is a right side view of the cassette guide shown in FIGS. 66 through 68;

FIG. 70 is a left side plan view of the pump shaft on which is mounted the jaws assembly shown in FIGS. 59 through 61;

FIG. 91 is a front plan view of an optical sensor module;

FIG. 92 is a side view of the optical sensor module shown in FIG. 91;

FIG. 93 is top view of the optical sensor module shown in FIGS. 91 and 92;

FIG. 94 is a bottom view of the optical sensor module shown in FIGS. 91 through 93 showing the optical source and sensor pair for detecting the closed position of the slide lock;

FIG. 95 is a first cutaway view of the optical sensor module shown in FIGS. 91 through 94 showing the optical sources for detecting the cassette indentification bits;

FIG. 96 is a second cutaway view of the optical sensor module shown in FIGS. 91 through 94 showing the optical sensors for detecting the cassette identification bits, and the optical source and sensor pair for detecting air bubbles in the fluid line;

FIG. 97 is a bottom plan view of the elastomeric valve actuator seal used to bias the value actuators in an upward position;

FIG. 98 is a cutaway view of the valve actuator seal shown in FIG. 97;

FIG. 99 is a bottom view of the main pump unit chassis having the various components for one pump mounted thereon, with the slide lock in the open position ready to receive a cassette;

FIG. 100 is a bottom view of the main pump unit chassis shown in FIG. 99, with the slide lock in the closed position as it would be if a cassette were installed and latched onto the main pump unit;

FIG. 101 is a top view of the cassette shown in FIGS. 43 through 49 in the installed position relative to the optical sensor module, with all other parts removed for clarity;

FIG. 102 is a side view of the cassette and optical sensor module of FIG. 101;

FIG. 103 is a first cutaway view of the cassette and the optical sensor module of FIGS. 101 and 102, showing a cassette identifying indicia having a logical zero value;

FIG. 104 is a second cutaway view of the cassette and the optical sensor module of FIGS. 101 and 102, showing a cassette indentifying indicia having a logical one value;

FIG. 105 is a cutaway view from FIG. 99 showing the slide lock in the open position over the cassette-in-place sensor of the optical sensor module;

FIG. 106 is a cutaway view from FIG. 105 showing how the slanted surface reflects the light beam away from the cassette-in-place sensor;

FIG. 112 is a cutaway view from the side of the main pump unit chassis having the various components for one pump mounted thereon and a cassette installed, showing the pump drive train;

FIG. 113 is a sectional view of the pump and valves showing the beginning of the fill cycle;

FIG. 114 is a sectional view of the pump and valves showing the beginning of the pump cycle;

FIG. 115 is a sectional view of the pressure plateau, the pressure diaphragm, and the pressure transducer; and FIG. 116 is a second sectional view of the pressure plateau, the pressure diaphragm, and the pressure transducer shown in FIG. 115.

DETAILED DESCRIPTION OF THE PREFERRED EMBODIMENT

The Cassette

Figure 1:
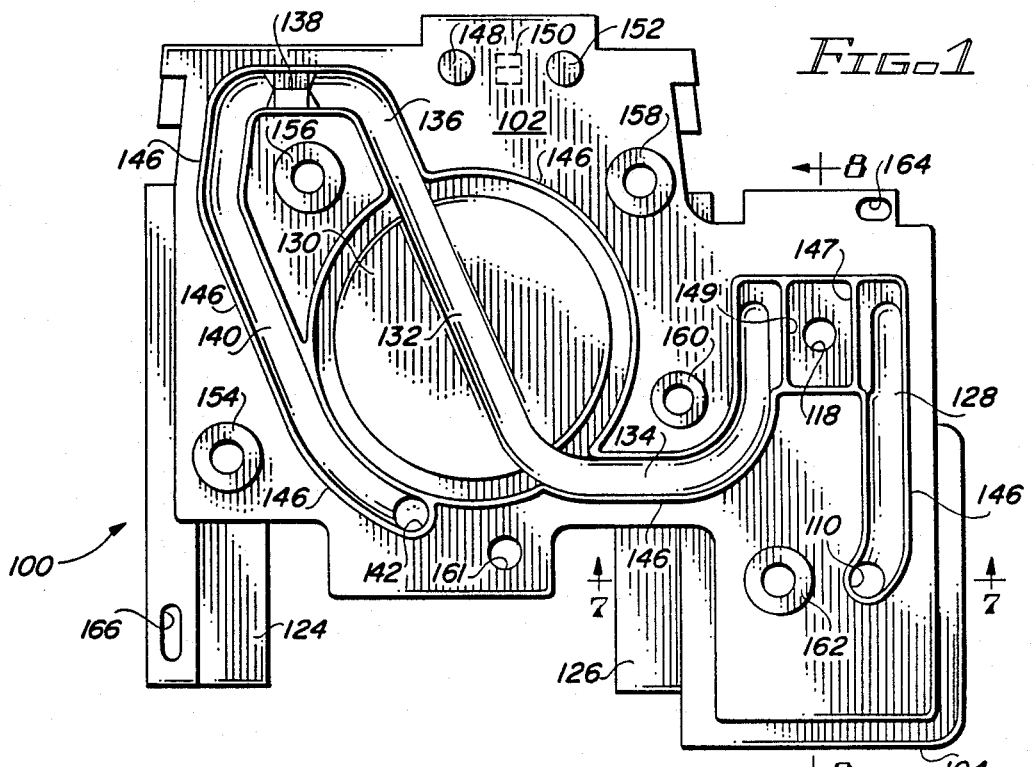
FIG. 1 is a top plan view of a disposable cassette body showing most of the fluid path through the cassette.

The preferred embodiment of the cassette operated by the drive system of the present invention includes all of the features described above in a single compact disposable cassette constructed of seven parts. Prior to a discussion of the construction and operation of the cassette, the basic construction of which is the subject of the above-identified patent application entitled "Disposable Cassette for a Medication Infusion System," it is advantageous to discuss the construction and configuration of the seven components included in the cassette. The first of these components and the one around which the other six components are assembled in a cassette body 100, which is shown in FIGS. 1 through 8. The cassette body 100 has an upper surface portion 102 which is essentially flat with a number of protrusions and indentations located in the top surface thereof (FIG. 1). The upper surface portion 102 has a thickness sufficient to accommodate the indentations mentioned above, some of which are fluid passageways which will be discussed below.

Referring generally to FIGS. 1 through 8, a bubble trap 104 is located at the front right corner of the cassette body 100 below the upper surface portion 102, which bubble trap 104 is essentially square in cross-section (FIG. 4). The bubble trap 104 includes therein a bubble chamber 106 which is open at the bottom thereof (FIGS. 4, 7, and 8) and closed at the top by the bottom of the upper surface portion 102 of the cassette body 100. A siphon tube 108 is located in the bubble chamber 106, and the siphon tube 108 has an aperture 110 therein leading from the bottom of the bubble chamber 106 to the top of the upper surface portion 102 of the cassette body 100.

Located behind the bubble trap 104 below the upper surface portion 102 of the cassette body 100 on the right side thereof is a pump cylinder 112 (FIG. 3-5, 8). The pump cylinder 112 does not extend downward as far as does the bubble trap 104. The pump cylinder 112 is open on the bottom thereof, and is arranged and configured to receive a piston which will be discussed below. The inner configuration of the pump cylinder 112 has a main diameter bore 114, with a greater diameter bore 116 near the bottom of the pump cylinder 112. The interior of the bottom of the pump cylinder 112 below the greater diameter bore 116 as well as the area immediately between the greater diameter bore 116 and the main diameter bore 114 are tapered to facilitate entry of the piston. The main diameter bore 114 terminates at the top thereof in a frustroconical smaller diameter aperture 118 leading to the top of the upper surface portion 102 of the cassette body 100 (FIG. 1). The smaller diameter aperture 118 is tapered, having a smaller diameter at the top thereof than at the bottom.

Extending from on the back side of the exterior of the bubble trap 104 facing the pump cylinder 112 are two piston retaining fingers 120 and 122 (FIGS. 3 and 4) defining slots therein. The slots defined by the two piston retaining fingers 120 and 122 face each other, and are open at the bottoms thereof to accept in a sliding fashion a flat segment fitting between the two piston retaining fingers 120 and 122. The two piston retaining fingers 120 and 122 extend from the lower surface of the upper surface portion 102 of the cassette body 100 to a location between the bottom of the pump cylinder 112 and the bottom of the bubble trap 104.

Also extending from the bottom side of the upper surface portion 102 of the cassette body 100 are two latch supporting fingers 124 and 126 (FIGS. 1–4 and 7). The latch supporting finger 124 extends downwardly from the left side of the bottom of the upper surface portion 102 of the cassette body 100, and at the bottom extends toward the right slightly to form an L-shape in cross section. The latch supporting finger 124 extends toward the front of the cassette body 100 further than does the upper surface portion 102 of the cassette body 100 (FIG. 1), and terminates approximately two-thirds of the toward the back of the upper surface portion 102 of the cassette body 100.

The latch supporting finger 126 extends downwardly from the bottom of the upper surface portion 102 of the cassette body 100 at with the left side of the bubble trap 104 forming a portion of the latch supporting finger 126. The latch supporting finger 126 extends toward the left slightly at the bottom thereof to form a backwards L-shape in cross section. The latch supporting finger 126 parallels the latch supporting finger 124, and is equally deep (FIG. 4). The latch supporting fingers 124 and 126 together will hold the slide latch, to be described below.

The passageways located in the top of the upper surface portion 102 of the cassette body 100 may now be described with primary reference to FIG. 1. The passageways in the top of the upper surface portion 102 are all open on the top side of the upper surface portion 102, and are generally U-shaped as they are recessed into the top of the upper surface portion 102. A first passageway 128 communicates with the aperture 110 in the siphon tube 108 of the bubble trap 104 at one end thereof, and extends toward the back of the upper surface portion 102 of the cassette body 100 to a location to the right of the smaller diameter aperture 118 of the pump cylinder 112.

Figure 2:
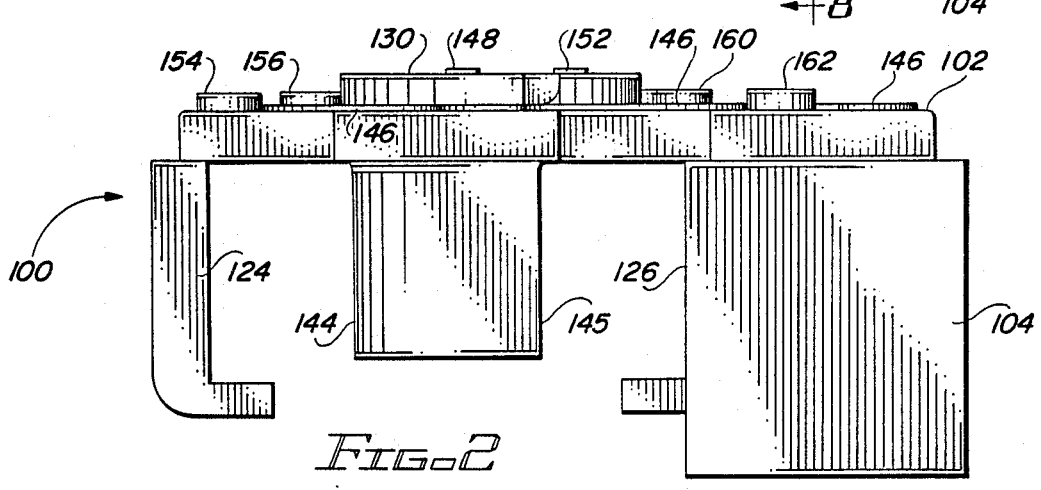
FIG. 2 is a front side view of the cassette body shown in FIG. 1.
Figure 3:
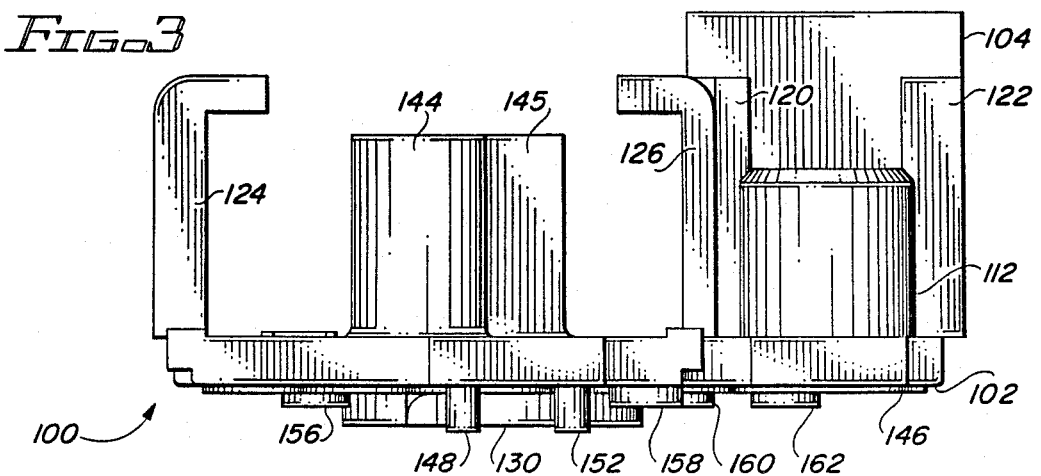
FIG. 3 is a back side view of the cassette body shown in FIGS. 1 and 2.

A cylindrical pressure plateau 130 which is essentially circular as viewed from the top extends above the upper surface portion 102 of the cassette body 100 slightly left of the center thereof (best shown in FIGS. 1 through 3, also shown in FIGS. 5 through 8). The top of the pressure plateau 130 is flat, with a channel 132 extending across the flat top of the pressure plateau 130. The channel 132 extends from five o'clock to eleven o'clock as viewed from the top in FIG. 1, with the back of the cassette body 100 being twelve o'clock. The channel 132 is also shown in cross-section in FIG. 115, and in a cutaway view in FIG. 116. The depth of the channel 132 in the surface of the pressure plateau 130 is not quite the height of the pressure plateau 130 above the upper surface portion 102 of the cassette body 100, with the channel 132 gradually becoming deeper with a smooth transition at the edges of the pressure plateau 130 to extend into the upper surface portion 102 of the cassette body 100 (FIG. 116).

A second passageway 134 in the top of the upper surface portion 102 of the cassette body 100 begins at a location to the left of the smaller diameter aperture 118 of the pump cylinder 112, and extends toward the front of the upper surface portion 102 approximately above the latch supporting finger 126. The second passageway 134 then travels to the left to connect in fluid communication with the end of the channel 132 in the pressure plateau 130 located at five o'clock. A third passageway 136 in the top of the upper surface portion 102 of the cassette body 100 begins at the end of the channel 132 in the pressure plateau 130 located at eleven o'clock, and moves toward the back and left of the cassette body 100.

At the end of the third passageway 136 is a recessed lens portion 138, which recessed lens portion is used to focus and reflect light used to detect air bubbles passing in front of the recessed lens portion 138. The recessed lens portion 138 is also recessed into the top of the upper surface portion 102 of the cassette body 100 to allow fluid to pass therethrough. The recessed lens portion 138 is part of the apparatus which is the subject of the above-identified patent application entitled "Air-In-Line Detector for a Medication Infusion System." A fourth passageway 140 in the top of the upper surface portion 102 of the cassette body 100 begins at the other side of the recessed lens portion 138 from the third passageway 136, and extends from the left and back of the cassette body 100 toward the front and right of the cassette body 100 around the pressure plateau 130 to a location at approximately seven o'clock on the pressure plateau 130. It should be noted that the fourth passageway 140 is spaced away from the pressure plateau 130 to allow for sealing means therebetween.

The end of the fourth passageway 140 terminates at the location at seven o'clock to the pressure plateau 130 in an aperture 142 extending through the upper surface portion 102 of the cassette body 100 (FIG. 1). Located underneath the upper surface portion 102 of the cassette body 100 concentrically around the aperture 142 is an the outlet tube mounting cylinder 144 (FIGS. 3 and 4) which is in fluid communication with the aperture 142. The outlet tube mounting cylinder 144 extends downwardly from the bottom of the upper surface portion 102 of the cassette body 100 to a location above the portions of the latch supporting finger 124 and the latch supporting finger 126 extending parallel to the upper surface 102 of the cassette body 100. A support fin 145 extends to the right from the front of the outlet tube mounting cylinder 144.

Located on top of the upper surface 102 of the cassette body 100 is a slightly raised border 146 (FIG. 1) which completely surrounds the first passageway 128, the smaller diameter aperture 118, the second passageway 134, the pressure plateau 130, the third passageway 136, the recessed lens portion 138, the recessed lens portion 138, and the fourth passageway 140. The slightly raised border 146, which is used for sealing purposes, closely surrounds the edges of all of the aforementioned segments of the cassette body 100, except as follows. The slightly raised border 146 is spaced away from the portions of the first passageway 128 and the second passageway 134 adjacent the smaller diameter aperture 118, and the smaller diameter aperture 118.

The portions of the slightly raised border 146 around the smaller diameter aperture 118 resembles a rectangle with its wider sides located to the front and back and spaced away from valve diaphragm 170, and its narrower sides to the right of the portion of the first passageway 128 adjacent the smaller diameter aperture 118 and to the left of the portion of the second passageway 134 adjacent the smaller diameter aperture 118. The rectangle is broken only at the locations the first passageway 128 and the second passageway 134 extends towards the front of the cassette body 100.

The slightly raised border 146 has a segment 147 located between the portion of the first passageway 128 adjacent the smaller diameter aperture 118 and the smaller diameter aperture 118 itself, with the segment 147 extending between the two wider sides of the rectangle. The slightly raised border 146 also has another segment 149 located between the portion of the second passageway 134 adjacent the smaller diameter aperture 118 and the smaller diameter aperture 118 itself, with the segment 149 extending between the two wider sides of the rectangle. The slightly raised border 146 is also spaced away from the sides of the pressure plateau 130, and the portions of the second passageway 134 and the third passageway 136 immediately adjacent the pressure plateau 130.

Located at the back of the upper surface 102 of the cassette body 100 are three cassette identifying indicia 148, 150, and 152. The first and third cassette identifying indicia 148 and 152 are small, solid cylinders extending upward from the top of the upper surface 102 of the cassette body 100 (FIGS. 1 and 3). The second cassette identifying indicia 150 is a prism cut into the bottom of the upper surface 102 of the cassette body 100 (FIG. 4). The first, second, and third cassette identifying indicia 148, 150, and 152 are the subject of the above-identified patent application entitled "Cassette Optical Indentification Apparatus for a Medication Infusion System." It will be noted that the cassette identifying indicia 148, 150, and 152 may be in any order or configuration, and are used for different ID codes to identify up to eight different cassettes. Additional ID bits could also be used if more than eight different cassettes are used. If redundant codes are desired, the three bits would of course accommodate the use of less than eight different cassettes.

Completing the construction of the cassette body 100 are five hollow cylinders 154, 156, 158, 160 and 162 protruding from the top surface of the upper surface 102 of the cassette body 100, an aperture 161 and a slot 164 located in the top surface of the upper surface 102 of the cassette body 100, and a slot 166 located in the top surface of the latch supporting finger 124. Four of the hollow cylinders 154, 156, 158, and 160 are located around the pressure plateau 130, with the fifth hollow cylinder 162 being located to the left of the aperture 110 over the bubble trap 104. The aperture 161 is located in the top surface of the upper surface 102 of the cassette body 100 in front and to the right of center of the pressure plateau 130. The slot 164 is located in the top surface of the upper surface 102 of the cassette body 100 near the back and the right side thereof. The slot 166 is located in the top surface of the latch supporting finger 124 near the front of the cassette body 100.

Referring now to FIGS. 9 through 12, a valve diaphragm 170 is shown which is arranged and configured to fit over the top of the upper surface 102 of the cassette body 100 (FIG. 1). The valve diaphragm 170 is made of flexible, resilient material, such as a medical grade silicone rubber. The hardness of the material used for the valve diaphragm 170 would be between thirty and fifty on the Shore A scale, with the preferred embodiment utilizing a hardness of approximately thirty-five. The valve diaphragm 170 has three primary functions, the first of which is to seal the tops of the first, second, third, and fourth passageways 128, 134, 136, and 140, respectively. Accordingly, the main surface of the valve diaphragm 170 is flat, and is sized to fit over the first, second, third, and fourth passageways 128, 134, 136, and 140, respectively, and also over the entire slightly raised border 146. The flat portion of the valve diaphragm 170 has three apertures 172, 174, and 176, and a notch 175 therein to accommodate the hollow cylinders 156, 160, and 162 and a pin fitting into the aperture 161 (FIG. 1), respectively, and to align the valve diaphragm 170 in position over the top of the upper surface 102 of the cassette body 100. It should be noted that the valve diaphragm 170 does not necessarily surround the other two hollow cylinders 154 and 158.

The second primary function of the valve diaphragm 170 is to provide both an inlet valve between the first passageway 128 and the smaller diameter aperture 118 leading to the pump cylinder 112, and to provide an outlet valve between the smaller diameter aperture 118 leading to the pump cylinder 112 and the second passageway 134. To fulfill this function the valve diaphragm 170 has an essentially rectangular domed portion 178 (shown in plan view in FIGS. 9 and 10, and in cross-sectional views in FIGS. 11 and 12) forming a cavity 180 in the bottom of the valve diaphragm 170. When the valve diaphragm 170 is installed in position on the top of the upper surface 102 of the cassette body 100, the cavity 180 will be located just inside the rectangular portion of the slightly raised border 146 around the smaller diameter aperture 118 leading to the pump cylinder 112 (FIG. 1).

Figure 9:
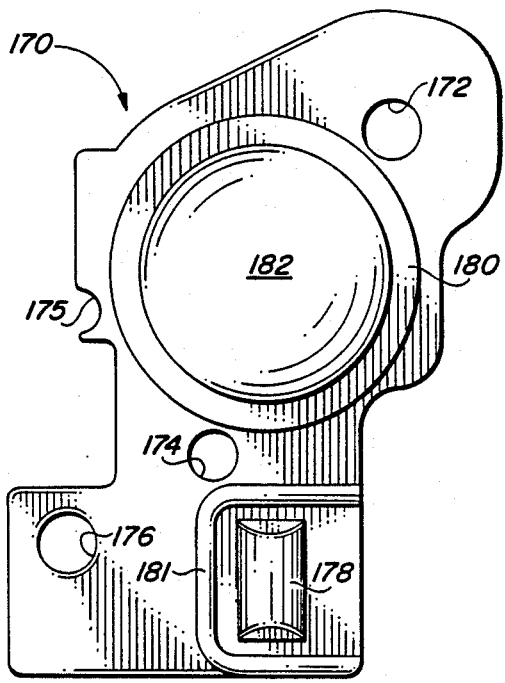
FIG. 9 is a top plan view of a valve diaphragm used to seal the passageways on the top surface of the cassette body shown in FIG. 1, to function as the pressure diaphragm, and also to function as the valves for the pump.

The cavity 180 will therefore be in fluid communication with the first passageway 128, the smaller diameter aperture 118 leading to the pump cylinder 112, and the second passageway 134. Prior to installation of the cassette onto the main pump unit, the cavity 180 allows the open fluid path to facilitate priming of the cassette, where all air is removed from the system. Once primed, the cassette may be inserted onto the main pump unit and the cavity 180 will contact valve actuators to prevent free flow through the cassette. By using an inlet valve actuator to force the domed portion 178 over the segment 147 of the slightly raised border 146 (FIG. 1), the flow of fluids between the first passageway 128 and the smaller diameter aperture 118 will be blocked, but the flow of fluids between the smaller diameter aperture 118 and the second passageway 134 will be unaffected. Likewise, by using an outlet valve actuator to force the domed portion 178 over the segment 149 of the slightly raised border 146 (FIG. 1), the flow of fluids between the smaller diameter aperture 118 and the second passageway 134 will be blocked, but the flow of fluids between the first passageway 128 and the smaller diameter aperture 118 will be unaffected. Extending around and spaced away from the front and sides of the domed portion 178 on the top surface of the valve diaphragm 170 is a U-shaped raised rib 181, the legs of which extend to the back of the valve diaphragm 170 (FIG. 9).

The third primary function of the valve diaphragm 170 is to provide a pressure diaphragm which may be used to monitor outlet fluid pressure. Accordingly, the valve diaphragm 170 has a pressure diaphragm 182 which is supported atop an upper cylindrical segment 184, which in turn is located atop a lower cylindrical segment 186 extending above the surface of the valve diaphragm 170. The upper cylindrical segment 184 and the lower cylindrical segment 186 have identical inner diameters, with a lower cylindrical segment 186 having a greater outer diameter than the upper cylindrical segment 184. A portion of the top of the lower cylindrical segment 186 extends outwardly around the bottom of the upper cylindrical segment 184, creating a lip 188.

Figure 11:
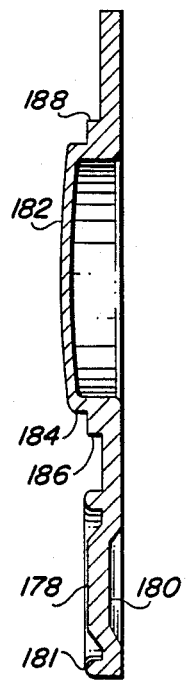
FIG. 11 is a cutaway view from the back side of the valve diaphragm shown in FIGS. 9 and 10.
Figure 22:
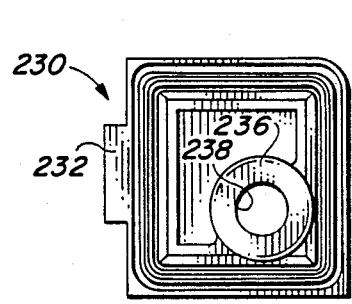
FIG. 22 is a top view of a bubble chamber cap.
Figure 24:
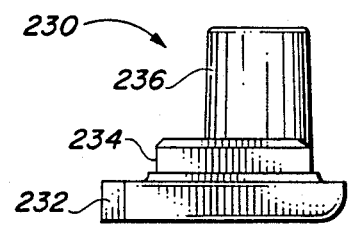
FIG. 24 is a left side view of the bubble chamber cap shown in FIGS. 22 and 23.
Figure 12:
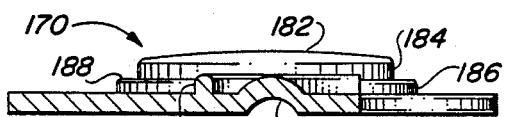
FIG. 12 is a cutaway view from the right side of the valve diaphragm shown in FIGS. 9 and 10.
Figure 25:
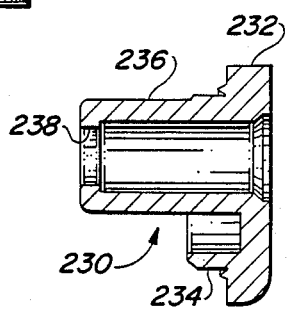
FIG. 25 is a cutaway view from the back side of the bubble chamber cap shown in FIGS. 22 through 24.

In the preferred embodiment, the pressure diaphragm 182 may be domed slightly, as seen in FIG. 11.

Turning now to FIGS. 13 through 23, a retainer cap 190 is shown which fits over the valve diaphragm 170 after it is mounted on the top of the upper surface 102 of the cassette body 100. The retainer cap 190 thus functions to cover the top of the cassette body 100, retaining the valve diaphragm 170 between the retainer cap 190 and the cassette body 100 in a sealing fashion. The retainer cap 190 thus has the same general outline when viewed from the top (FIG. 13) as the cassette body 100 (FIG. 1). Located in the bottom of the retainer cap 190 (FIG. 14) are six pins 192, 194, 196, 198, 200, and 199, which are to be received by the hollow cylinders 154, 156, 158, 160, and 162 and the aperture 161, respectively, in the cassette body 100 to align the retainer cap 190 on the cassette body 100. Also located in the bottom of the retainer cap 190 is a tab 202 to be received by the slot 164, and a tab 204 to be received by the slot 166.

The retainer cap 190 has three apertures 206, 208, and 210 therethrough located to coincide with the locations of the first cassette identifying indicia 148, the second cassette identifying indicia 150, and the third cassette identifying indicia 152, respectively. The size of the three apertures 206, 208, and 210 is sufficient to receive the small, solid cylinders which the first cassette identifying indicia 148 and the third cassette identifying indicia 152 comprise.

Located in the retainer cap 190 is a rectangular aperture 212 (FIGS. 13, 14, 19 and 20) for placement over the domed portion 178 on the valve diaphragm 170. The rectangular aperture 212 in the retainer cap 190 is slightly larger than the domed portion 178 on the valve diaphragm 170 to prevent any closure of the cavity 180 formed by the domed portion 178 when the retainer cap 190 is placed over the valve diaphragm 170 and the cassette body 100. The domed portion 178 of the valve diaphragm 170 therefore will protrude through the rectangular aperture 212 in the retainer cap 190. In the bottom of the retainer cap 190 around the rectangular aperture 212 is a U-shaped groove 214 (FIG. 14) designed to accommodate the U-shaped raised rib 181 on the valve diaphragm 170.

Also located in the retainer cap 190 is a circular aperture 216 (FIGS. 13 and 14), which has a diameter slightly larger than the outer diameter of the upper cylindrical segment 184 on the valve diaphragm 170, to allow the upper cylindrical segment 184 and the pressure diaphragm 182 to protrude from the circular aperture 216 in the retainer cap 190. The diameter of the circular aperture 216 is smaller than the outer diameter of the lower cylindrical segment 186 on 170, and on the bottom of the retainer cap 190 is disposed concentrically around the circular aperture 216 a cylindrical recess 218 to receive the lower cylindrical segment 186 on the valve diaphragm 170. Disposed in the cylindrical recess 218 on the bottom side of the retainer cap 190 is a circular raised bead 220 (FIGS. 14, 19, and 21) to help in the sealing of the cassette as it is assembled.

The retainer cap 190 has a front edge 222 (FIG. 16), a back edge 224 (FIG. 15), and left (FIG. 18) and right (FIG. 17) side edges 226 and 228, respectively. The edges 222, 224, 226, and 228 will contact the top of the upper surface 102 of the cassette body 100 when the retainer cap 190 is assembled onto the cassette body 100 with the valve diaphragm 170 disposed therebetween. The retainer cap 190 is attached to the cassette body 100 in the preferred embodiment by ultrasonic welding, but adhesives or other boding techniques known in the art may also be used.

Referring next to FIGS. 22 through 26, a bubble chamber cap 230 is illustrated which is for placement onto the open bottom of the bubble trap 104 (FIG. 4). The bubble chamber cap 230 is on the bottom (FIG. 23) the same size as the outer edges of the bottom of the bubble trap 104 (FIG. 4), and has a tab 232 (FIGS. 22 through 24) on the bottom which will project toward the back of the cassette beyond the back edge of the bubble trap 104. The bubble chamber cap 230 has a rectangular wall portion 234 (FIG. 24) extending upward from the bottom of the bubble chamber cap 230 and defining therein a square space, which rectangular wall portion 234 is sized to fit inside the bubble chamber 106 (FIG. 4).

Located at the front and left sides of the rectangular wall portion 234 and extending upwards from the bottom of the bubble chamber cap 230 is an inlet cylinder 236 (FIGS. 22, 24, and 26) having an inlet aperture 238 extending therethrough. The inlet aperture 238 extends through the bottom of the bubble chamber cap 230 (FIGS. 23 and 25), and is designed to receive from the bottom of the bubble chamber cap 230 a length of tubing therein. The bubble chamber cap 230 is attached to the bottom of the bubble trap 104 in the cassette body 100 in the preferred embodiment by ultrasonic welding, but adhesives or other bonding techniques known in the art may also be used.

Figure 26:
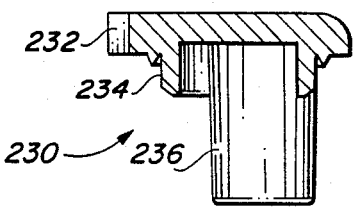
FIG. 26 is a cutaway view from the right side of the bubble chamber cap shown in FIGS. 22 through 24.
Figure 33:
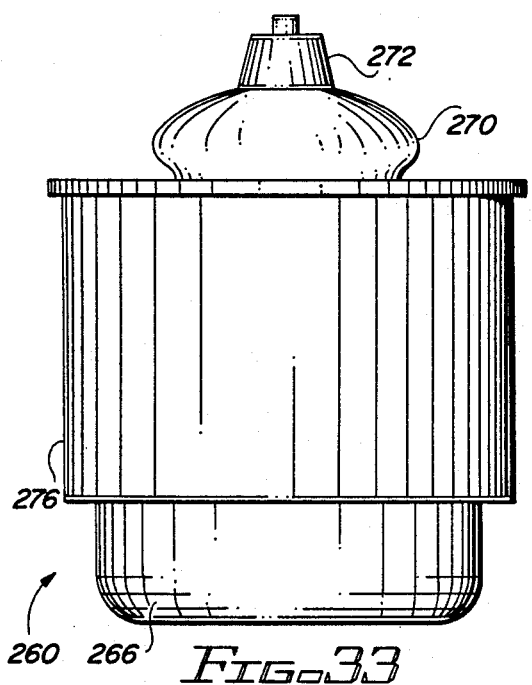
FIG. 33 is a side plan view of the piston cap and boot seal, which function both as a piston and as a bacterial seal.

When the bubble chamber cap 230 is mounted to the bubble trap 104, the inlet cylinder 236 extends up to at least half of the height of the bubble chamber 106 (FIG. 7), and the siphon tube 108 (FIG. 7) draws fluid from the bottom of the siphon tube 108 in the space within the rectangular wall portion 234 of the bubble chamber cap 230 (FIG. 26). It will be appreciated by those skilled in the art that fluid will enter the bubble chamber 106 through the inlet aperture 238 in the inlet cylinder 236 near the top of the siphon tube 108, maintaining all air bubbles above the level near the bottom of the bubble chamber 106 at which fluid is drawn from the bubble chamber 106 by the siphon tube 108.

Moving now to FIGS. 27 through 32, a slide latch 240 is disclosd which served two main functions in the cassette. The slide latch 240 first serves to latch the cassette into place in a main pump unit. It also serves to block the flow of fluid through the cassette when it is not installed, with the closing of the slide latch 240 to lock the cassette into place on the main pump unit also simultaneously allowing the flow of fluid through the cassette. The slide latch 240 slides from the front of the cassette body 100 (FIG. 2) between the latch supporting finger 124 and the latch supporting finger 126.

The slide latch 240 has an essentially rectangular, flat front portion 242 (FIG. 31) which is of a height equal to the height of the cassette body 100 with the retainer cap 190 and the bubble chamber cap 230 installed, and a width equal to the distance between the left side of the bubble trap 104 and the left side of the cassette body 100. Two small notches 244 and 246 are removed from the back side of the front portion 242 at the top thereof (FIGS. 27, 28, and 30), the small notch 244 being removed at a location near the left corner, and the small notch 246 being removed at the right corner.

Extending from the back side of the front portion 242 about three-quarters of the way down towards the back is a horizontal bottom portion 248 (FIG. 29), which has its edges directly below the closest edges of the small notch 244 and the small notch 246. Extending from the inner edge of the small notch 244 at the top of the slide latch 240 down to the bottom portion 248 is an inverted angled or L-shaped portion 250. Similarly, extending from the inner edge of the small notch 246 at the top of the slide latch 240 down to the bottom portion 248 is an inverted, backwards angled or L-shaped portion 252 (FIGS. 27 and 28).

Spaced outwardly from the left side of the bottom portion 248 and the left side of the leg of the inverted L-shaped portion 250 is a left slide side 254. Likewise, spaced outwardly from the right side of the bottom portion 248 and the right side of the leg of the inverted, backwards L-shaped portion 252 is a right slide side 256 (FIGS. 28 and 30). The left and right slide sides 254 and 256 are located slightly above the bottom of the bottom portion 248 (FIG. 30). The left and right slide sides 254 and 256 are of a height to be engaged in the latch supporting finger 124 and the latch supporting finger 126 (FIG. 2), respectively.

Located in the bottom portion 248 is an elongated, tear-shaped aperture 258 (FIG. 29), with the wider portion thereof toward the front of the slide latch 240 and the extended narrower portion thereof toward the back of the slide latch 240. When the slide latch 240 is inserted into the latch supporting finger 124 and the latch supporting finger 126 on the cassette body 100, and the slide latch 240 is pushed fully toward the back of the cassette body 100, the wider portion of the elongated, tear-shaped aperture 258 will be aligned with the aperture 142 in the outlet tube mounting cylinder 144 (FIG. 4) to allow a segment of tubing (not shown) leading from the aperture 142 to be open. When the slide latch 240 is pulled out from the front of the cassette body 100, the segment of tubing (not shown) will be pinched off by the narrower portion of the elongated, tear-shaped aperture 258.

It is critical that the design and location of the elongated, tear-shaped aperture 258 in the slide latch 240 ensure that the slide latch 240 engages the main pump unit before the tubing is opened up, and fluid is allowed to flow through the cassette. Likewise, the tubing must be pinched off and the fluid path through the cassette must be blocked before the slide latch 240 releases the cassette from the main pump unit. In addition, the choice of material for the slide latch 240 is important, with a lubricated material allowing the pinching operation to occur without damaging the tubing (not shown). Examples of such materials are silicone or Teflon impregnated acetals such as Delren.

Located at the back of the slide latch 240 on the inside of the right slide side 256 at the bottom thereof is a tab 257 (FIGS. 27, 30, and 32) which is used to engage the main pump unit with the cassette when the slide is closed. Located on the top side of the bottom portion 248 to the right of the elongated, tear-shaped aperture 258 is a small wedge-shaped retaining tab 259 (FIG. 27, 30, and 32). The retaining tab 259 cooperates with the bottom of the slightly raised border 146 of the cassette body 100 (FIG. 2), to resist the slide latch 240 from being freely removed once installed into the cassette body 100. When the slide latch 240 is pulled back out from the front of the cassette body 100 so that the wider portion of the elongated, tear-shaped aperture 258 is aligned with the aperture 142 in the outlet tube mounting cylinder 144, the retaining tab 259 will engage the slightly raised border 146 (FIGS. 2 and 4), resisting the slide latch 240 from being drawn further out.

Referring now to FIGS. 33 through 36, a one-piece piston cap and boot seal 260 is illustrated, which is the subject of the above-identified patent application entitled "Piston Cap and Boot Seal for a Medication Infusion System," and which is for use on and in the pump cylinder 112 (FIGS. 3 and 8). The piston cap and boot seal 260 is of one-piece construction, and is made of flexible, resilient material, such as silastic (silicone rubber) or medical grade natural rubber. Natural rubber may be used to minimize friction, since some sticking of a silicone rubber piston cap and boot seal 260 in the pump cylinder 112 (FIG. 8) may occur. Telfton impregnated silastic or other proprietary formulas widely available will overcome this problem. In addition, the piston cap and boot seal 260 may be lubricated with silicone oil prior to installation in the pump cylinder 112. The advantage of using silastic is that it may be radiation sterilized, whereas natural rubber must be sterilized using gas such as ethylene oxide. In addition, silastic has better wear characteristics than natural rubber, making it the preferred choice.

The piston cap and boot seal 260 includes a piston cap portion indicated generally at 262, and a boot seal portion comprising a retaining skirt 264 and a thin rolling seal 266. The piston cap portion 262 includes a hollow cylindrical segment 268 having an enlarged, rounded piston cap head 270 located at the top thereof. The piston cap head 270 has a roughly elliptical cross-section, with an outer diameter on the sides sufficient to provide a dynamic seal in the main diameter bore 114 of the pump cylinder 112 (FIG. 8). The roughly elliptical configuration of the piston cap head 270 closely fits the top of the main diameter bore 114 of the pump cylinder 112. Extending from the top of the piston cap head 270 at the center thereof is a frustroconical segment 272, with the larger diameter of the frustroconical segment 272 being at the bottom thereof attached to the piston cap head 270. The frustroconical segment 272 is of a size to closely fit in the smaller diameter aperture 118 of the pump cylinder 112 (FIG. 8).

The hollow cylindrical segment 268 and the piston cap head 270 together define a closed end of the piston cap and boot seal 260 to receive a piston, which will be described below. The hollow cylindrical segment 268 has located therein a smaller diameter portion 274, which smaller diameter portion 274 is spaced away from the bottom of the piston head 270 to provide retaining means to retain a piston in the hollow cylindrical segment 268 between the piston cap head 270 and the smaller diameter portion 274.

The retaining skirt 264 is essentially cylindrical, and is designed to fit snugly around the outer diameter of the pump cylinder 112 (FIG. 8). Prior to installation and with the piston cap and boot seal 260 in a relaxed configuration as shown in FIGS. 33 through 36, the retaining skirt 264 is located roughly around the hollow cylindrical segment 268. The retaining skirt 264 has an internal diameter sufficiently small to retain the retaining skirt 264 in position around the pump cylinder 112 (FIG. 8) without moving when the piston cap portion 262 moves.

Located around the inner diameter of the retaining skirt 264 is a tortuous path 276 leading from one end of the retaining skirt 264 to the other. The tortuous path 276 is required for sterilization of the assembled cassette, to allow the sterilizing gas to sterilize the area between the inside of the pump cylinder 112 and the piston cap and boot seal 260, which would be closed and may remain unsterilized if the tortuous path 276 did not exist. In addition, since the sterilizing gas is hot and cooling occurs rapidly after the sterilizing operation, the tortuous path 276 allows pressure equalization to occur rapidly where it otherwise would not. In the preferred embodiment, the tortuous path 276 is a series of threads in the inner diameter of the retaining skirt 264.

Completing the construction of the piston cap and boot seal 260 is the rolling seal 266, which is a segment defined by rotating around the centerline of the piston cap and boot seal 260 a U having a first leg at the radius of the hollow cylindrical segment 268 and a second leg at the radius of the retaining skirt 264, with the top of the first leg of the U being attached to the bottom of the hollow cylindrical segment 268 and the top of the second leg of the U being attached to the bottom of the retaining skirt 264. When the piston cap and boot seal 260 is installed and the piston cap portion 262 moves in and out in the main diameter bore 114 in the pump cylinder 112 (FIG. 8), the legs of the U will vary in length, with one leg becoming shorter as the outer leg becomes longer. In this manner, the rolling seal 266 provides exactly what its name implies—a seal between the piston cap portion 262 and the retaining skirt 264 which rolls as the piston cap portion 262 moves.

Figure 23:
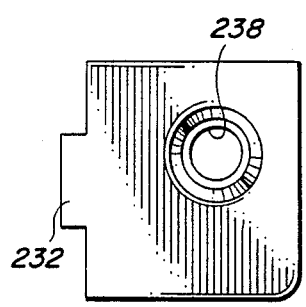
FIG. 23 is a bottom view of the bubble chamber cap shown in FIG. 22.
Figure 10:
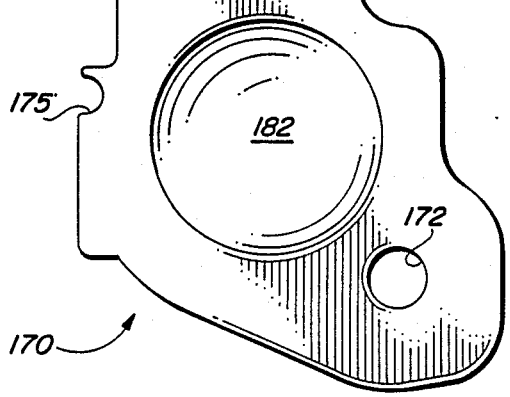
FIG. 10 is a bottom view of the valve diaphragm shown in FIG. 9.

Referring now to FIGS. 37 through 42, a piston assembly 280 is shown which drives the piston cap portion 262 of the piston cap and boot seal 260 (FIG. 36) in the pump cylinder 112 (FIG. 8). The piston assembly 280 has a rectangular base 282 which is positioned horizontally and locally directly behind the bubble chamber cap 230 (FIG. 24) when the piston cap portion 262 is fully inserted into the pump cylinder 112. The rectangular base 282 has a notch 284 (FIGS. 41 and 42) in the front edge thereof, which notch is slightly larger than the tab 232 in the bubble chamber cap 230 (FIG. 23).

Figure 38:
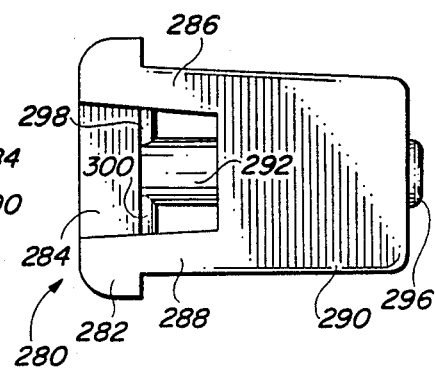
FIG. 38 is a front side view of the piston shown in FIG. 37.
Figure 64:
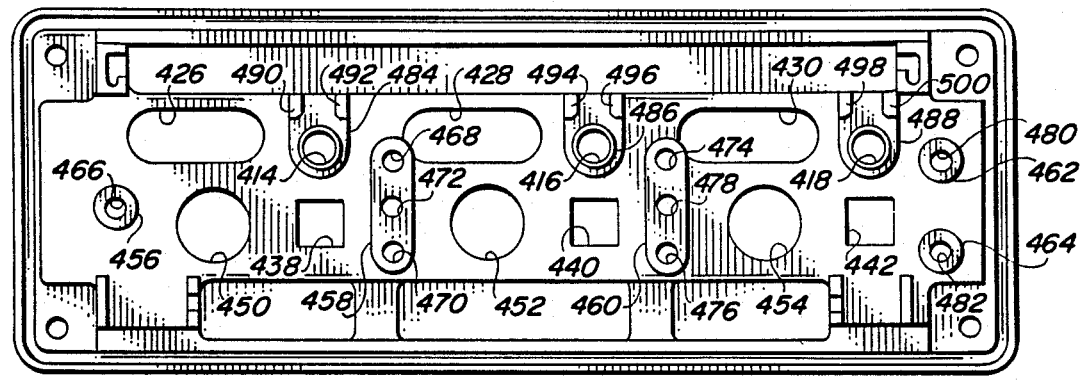
FIG. 64 is a top view of the main pump unit chassis shown in FIGS. 62 and 63.
Figure 63:
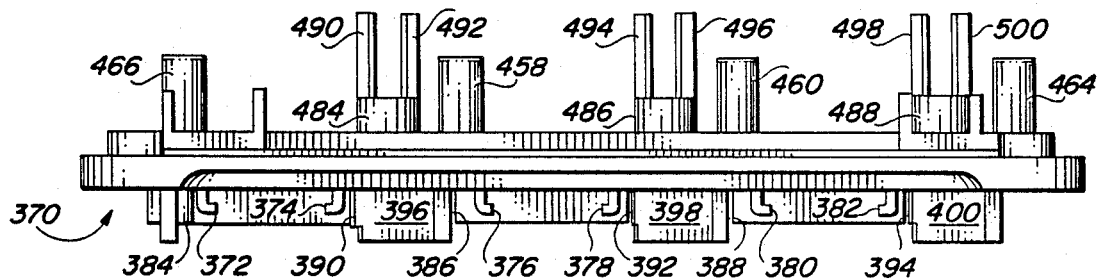
FIG. 63 is a front view of the main pump unit chassis shown in FIG. 62.

Extending upward from the front edge of the rectangular base 282 on the left side of the notch 284 is an arm 286, and extending upward from the front edge of the rectangular base 282 on the right side of the notch 284 is an arm 288. At the top of the arms 286 and 288 is a vertically extending rectangular portion 290 (FIG. 38). The rectangular portion 290 as well as the upper portions of the arms 286 and 288 are for insertion into and between the piston retaining finger 120 and the piston retaining finger 122 in the cassette body 100 (FIG. 4).

The top of the rectangular portion 290 will contact the bottom of the upper surface 102 of the cassette body 100 (FIG. 8) to limit the upward movement of the piston assembly 280, the rectangular base 282 being approximately even with the bubble chamber cap 230 (FIG. 24) installed in the bottom of the bubble trap 104 of the cassette body 100 when the piston assembly 280 is in its fully upward position. The bottom of the rectangular portion 290 (FIG. 42) will contact the tab 232 on the bubble chamber cap 230 (FIG. 24) when the piston assembly 280, the piston head 296, and the piston cap portion 262 (FIG. 36) are fully retracted from the pump cylinder 112 (FIG. 8).

Figure 36:
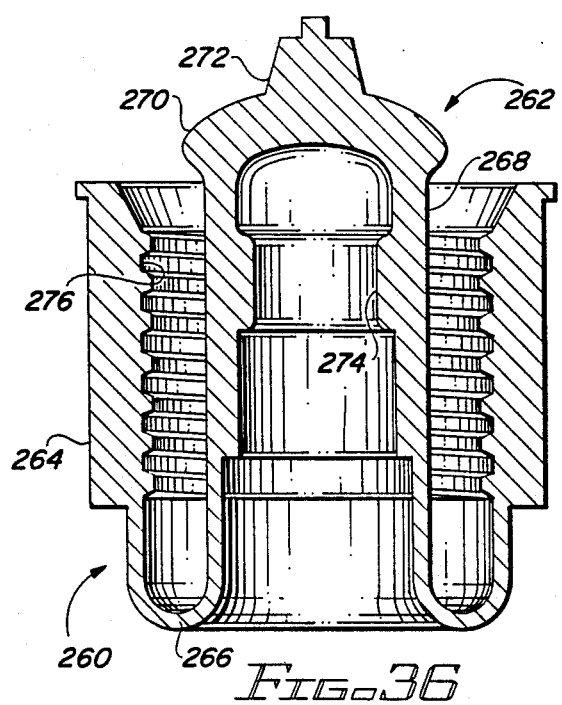
FIG. 36 is a cutaway view from the side of the piston cap and boot seal shown in FIGS. 33 through 35.
Figure 39:
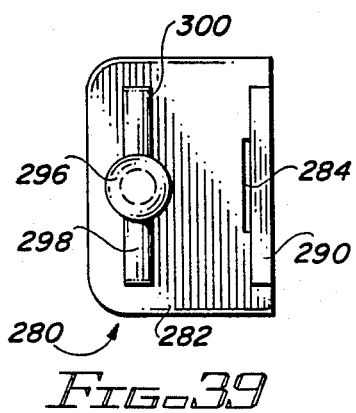
FIG. 39 is a top view of the piston shown in FIGS. 37 and 38.
Figure 40:
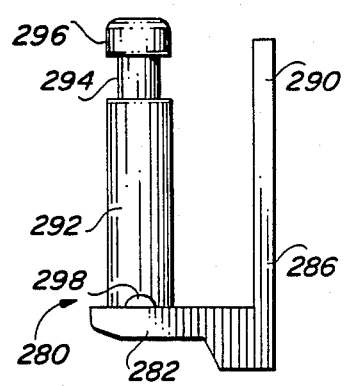
FIG. 40 is a left side view of the piston shown in FIGS. 37 through 39.
Figure 42:
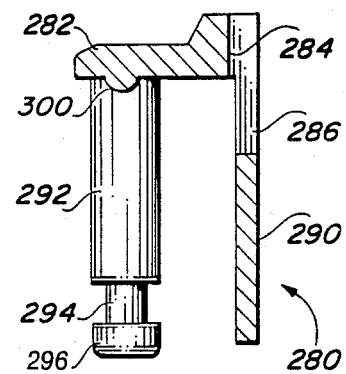
FIG. 42 is a cutaway view from the right side of the piston shown in FIGS. 37 through 41.

Extending upwards from the top of the rectangular base 282 near the back edge of the rectangular base 282 and located centrally with respect to the side edges of the rectangular base 282 is a cylindrical piston rod 292. At the top of the piston rod 292 is a reduced diameter cylindrical portion 294, and mounted on top of the reduced diameter cylindrical portion 294 is a cylindrical piston head 296. The diameter of the piston head 296 is larger than the diameter of the reduced diameter cylindrical portion 294, and the top of the piston head 296 has rounded edges in the preferred embodiment. The piston head 296 is designed to be received in the portion of the hollow cylindrical segment 268 between the smaller diameter portion 274 and the piston cap head 270 in the piston cap portion 262 (FIG. 36). The reduced diameter cylindrical portion 294 is likewise designed to be received in the smaller diameter portion 274 of the piston cap portion 262.

The top of the piston head 296 is slightly above the top of the rectangular portion 290, and when the piston assembly 280 is in its fully upward position, the piston head 296 will have brought the piston cap head 270 and the frustroconical segment 272 thereon (FIG. 36) to the top of the pump cylinder 112 and into the smaller diameter aperture 118 (FIG. 8), respectively, to completely eliminate volume both within the pump cylinder 112 and within the smaller diameter aperture 118.

Completing the construction of the piston assembly 280 are two raised beads 298 and 300, with the raised bead 298 being on the top surface of the rectangular base 282 on the left side of the piston rod 292, and the raised bead 300 being on the top surface of the rectangular base 282 on the right side of the piston rod 292. Both of the raised beads 298 and 300 extend from the sides of the piston rod 292 laterally to the sides of the rectangular base 282. The raised beads 298 and 300 will be used to center the piston assembly 280 with the jaws of the main pump unit used to drive the piston assembly 280, as well as to facilitate retaining the piston assembly 280 in the jaws.

The assembly and configuration of the cassette may now be discussed, with reference to an assembled cassette 302 in FIGS. 43 through 48, as well as to other figures specifically mentioned in the discussion. The valve diaphragm 170 is placed over the top of the upper surface 102 of the cassette body 100, with the apertures 172, 174, and 176 placed over the hollow cylinders 156, 160, 162, respectively. The retainer cap 190 is then located over the valve diaphragm 170 and the cassette body 100, and is secured in place by ultrasonic welding. Note again that while adhesive sealing may be used, it is more difficult to ensure the consistent hermetic seal required in the construction of the cassette 302.

The step of firmly mounting the retainer cap 190 onto the cassette body 100 exerts a bias on the valve diaphragm 170 (FIG. 9) causing it to be compressed in certain areas, particularly over the slightly raised border 146 on the top surface of the upper surface 102 of the cassette body 100 (FIG. 1). This results in excellent sealing characteristics, and encloses the various passageways located in the upper surface 102 of the cassette body 100. The first passageway 128 is enclosed by the valve diaphragm 170, communicating at one end thereof with the aperture 110 and at the other end thereof with the area between the cavity 180 and the upper surface 102 of the cassette body 100. The second passageway 134 also communicates with the area between the cavity 180 and the upper surface 102 of the cassette body 100 at one end thereof, with the other end of the second passageway 134 communicating with one end of the passageway 132 in the pressure plateau 130.

The pressure diaphragm 182 is located above the surface of the pressure plateau 130 (FIGS. 115 and 116), and a space exists between the edges at the side of the pressure plateau 130 and the inner diameters of the upper cylindrical segment 184 and the lower cylindrical segment 186. This allows the pressure diaphragm 182 to be quite flexible, a design feature essential to proper operation of the pressure monitoring apparatus. It may therefore be appreciated that the flow area between the second passageway 134 and the third passageway 136 is not just the area of the passageway 132, but also the area between the pressure diaphragm 182 and the pressure plateau 130, as well as the area around the sides of the pressure plateau 130 adjacent the upper cylindrical segment 184 and the lower cylindrical segment 186.

The third passageway 136 (FIG. 1) is also enclosed by the valve diaphragm 170 (FIG. 9), and communicates at one end with the other end of the passageway 132, and at the other end with the recessed lens portion 138. The fourth passageway 140 is enclosed by the valve diaphragm 170, and communicates at one end with the recessed lens portion 138 and at the other end with the aperture 142.

Next, the bubble chamber cap 230 is placed on the bottom of the bubble chamber 106, as shown in FIG. 44, and is secured by ultrasonically sealing the bubble chamber cap 230 to the cassette body 100. The piston cap portion 262 of the piston cap and boot seal 260 (FIG. 36) is inserted into the main diameter bore 114 of the pump cylinder 112 (FIG. 8), and pushed toward the top of the main diameter bore 114. Simultaneously, the retaining skirt 264 is placed over the outside of the pump cylinder 112 and is moved up the outer surface of the pump cylinder 112 to the position shown in FIGS. 46 and 48, which is nearly to the top of the outer surface of the pump cylinder 112. Next, the piston head 296 of the piston assembly 280 (FIGS. 37 and 40) is inserted into the hollow cylindrical segment 268 of the piston cap and boot seal 260, and is forced past the smaller diameter portion 274 until it snaps home, resting against the bottom of the piston cap head 270.

The slide latch 240 is then inserted into engagement with the cassette body 100, which is accomplished by sliding the left slide side 254 into the latch supporting finger 124 on the right side thereof and by sliding the right slide side 256 into the latch supporting finger 126 on the left side thereof. The slide latch 240 is then pushed fully forward to align the wider portion of the elongated, tear-shaped aperture 258 with the outlet tube mounting cylinder 144. An inlet tube 304 is adhesively secured in the inner diameter of the inlet aperture 238 in the bubble chamber cap 230, in fluid communication with the bubble chamber 106. An outlet tube 306 extends through the wider portion of the elongated, tear-shaped aperture 258 and is adhesively secured in the inner diameter of the outlet tube mounting cylinder 144 in the cassette body 100, in fluid communication with the fourth passageway 140 through the aperture 142.

The inlet tube 304 and the outlet tube 306 are shown in the figures only in part; on their respective ends not connected to the assembled cassette 302 they may have connector fittings such as standard luer connectors (not shown), which are well known in the art. The use of adhesives to attach the inlet tube 304 and the outlet tube 306 to the assembled cassette 302 also utilizes technology well known in the art. For example, adhesives such as cyclohexanone, methylene dichloride, or tetrahydrofuron (THF) may be utilized.

The Main Pump Unit

Figure 37:
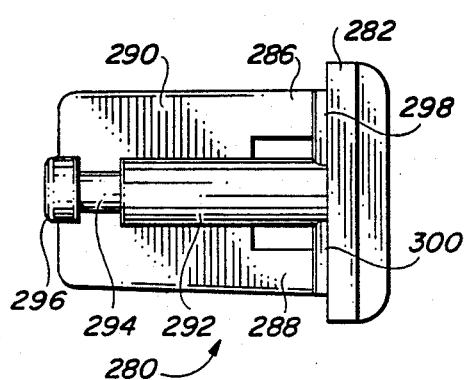
FIG. 37 is a back side plan view of a piston for insertion into the piston cap and boot seal shown in FIGS. 33 throug 36.
Figure 41:
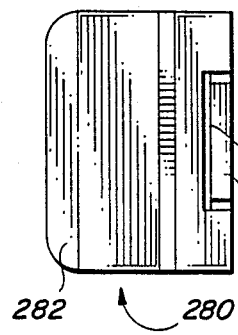
FIG. 41 is a bottom view of the piston shown in FIGS. 37 through 40.

The preferred embodiment of the main pump unit of the present invention includes a number of components used to hold, latch, and drive the cassette described above. Referring first to FIGS. 49 through 53, a latch head 310 is illustrated which is used to grasp the raised bead 298 and the raised bead 300 of the piston assembly 280 (FIG. 37). Extending from the front of the latch head 310 at the top thereof on the left side is a left jaw 312, and extending from the front of the latch head 310 at the top thereof on the right side is a right jaw 314. The left and right jaws 312 and 314 have curved indentations on the bottom sides thereof to receive the raised bead 298 and the raised bead 300 (FIG. 37), respectively. A space between the left jaw 312 and the right jaw 314 allows them to fit around the piston rod 292 of the piston assembly 280.

A cylindrical aperture 316 is located in the top of the latch head 310, which cylindrical aperture 316 is designed to receive a shaft on which the latch head 310 is mounted. A threaded aperture 318 in the back side of the latch head 310 communicates with the cylindrical aperture 316, and will have locking means installed therein to lock a shaft in the cylindrical aperture 316. An aperture 320 extends through the latch head 310 from the left side to the right side thereof near the back and bottom of the latch head 310.

A notch 322 is located in the latch head 310 at the bottom and front thereof and in the corner thereof, leaving a side portion 324 on the left side and a side portion 326 on the right side. An aperture 328 is located through the side portion 324, and an aperture 330 is located through the side portion 326, which apertures 328 and 330 are aligned. In addition, the portion of the latch head 310 including the left jaw 312 has a raised edge 327 facing upward and backward, and a raised edge 329 facing down and forward. The portion of the latch head 310 including the right jaw 314 has a raised edge 331 facing downward and forward. The raised edges 327, 329, and 331 will be used to limit the movement of the latch jaw, which will be discussed below.

A spring seat 332 is shown in FIGS. 54 and 55, which is designed to fit in the notch 322 in the latch head 310 (FIGS. 51 and 53). The spring seat 332 has an aperture 334 extending therethrough from the left side to the right side, which aperture 334 is slightly larger than the apertures 328 and 330 in the latch head 310. The spring seat 332 also has a cylindrical segment 336 extending from the front side thereof.

A latch jaw 340 is illustrated in FIGS. 56 through 58, which latch jaw 340 is used to grasp the bottom of the rectangular base 282 of the piston assembly 280 (FIG. 37) and maintain the left and right jaws 312 and 314 of the latch head 310 (FIG. 51) in contact with the raised bead 298 and the raised bead 300, respectively. The latch jaw 340 has a front jaw portion 342 approximately as wide as the left and right jaws 312 and 314 of the latch head 310, which jaw portion 342 is the portion of the latch jaw 340 which contacts the bottom of the rectangular base 282 of the piston assembly 280. Extending back from the left side of the jaw portion 342 is a left arm 344, and extending back from the right side of the jaw portion 342 is a right arm 346.

The left arm 344 has an aperture 248 (not shown) therethrough from the left side to the right side at the end of the left arm 344 away from the jaw portion 342. Likewise, the right arm 346 has an aperture 350 therethrough from the left side to the right side at the end of the right arm 346 away from the jaw portion 342. The apertures 348 and 350 are slightly smaller in diameter than the aperture 320 in the latch head 310 (FIGS. 49 and 50).

Extending upward from and at an approximately sixty degree angle with respect to the right arm 346 from the end of the right arm 346 away from the jaw portion 342 is a driving arm 352. At the end of the driving arm 352 which is not attached to the right arm 346 is a link pin 354 extending to the right. Completing the construction of the latch jaw 340 is a cylindrical recess 356 located in the back side of the jaw portion 342, which cylindrical recess 356 has an inner diameter larger than the outer diameter of the cylindrical segment 336 of the spring seat 332 (FIG. 55).

Referring now to FIGS. 59 through 61, the construction of a jaws assembly 360 from the latch head 310, the spring seat 332, and the latch jaw 340 is illustrated. The spring seat 332 fits within the notch 322 and between the left jaw 312 and the right jaw 314 of the latch head 310. A pin 362 is inserted through the aperture 328 in the side portion 324, the aperture 334 in the spring seat 332, and the aperture 330 in the side portion 326. The pin 362 is sized to fit snugly in the apertures 328 and 330, thereby retaining the pin 362 in place and allowing the spring seat 332 to rotate about the pin 362.

The latch jaw 340 is mounted onto the latch head 310 with the left jaw 312 and the right jaw 314 of the latch head 310 facing the jaw portion 342 of the latch jaw 340 using a pin 364.

The pin 364 is inserted through the aperture 348 (not shown) in the left arm 344, the aperture 320 in the latch head 310, and the aperture 350 in the right arm 346. The pin 364 is sized to fit snugly in the apertures 348 and 350, thereby retaining the pin 364 in place and allowing the latch jaw 340 to rotate about the pin 364.

A spring 366 has one end thereof mounted over the cylindrical segment 336 on the spring seat 332, and the other end thereof mounted in the cylindrical recess 356 in the latch jaw 340. The spring 366 acts to bias the latch jaw 340 in either the open position shown in FIG. 59 with the jaw portion 342 of 340 away from the left jaw 312 and the left jaw 312 of the latch head 310, or in the closed position shown in FIG. 61, with the jaw portion 342 of the latch jaw 340 urged closely adjacent the left jaw 312 and the right jaw 314 of the latch head 310. The movement of the latch jaw 340 in both directions with respect to the latch head 310 is limited, to the position shown in FIG. 59 by the driving arm 352 contacting the raised edge 327, and to the position shown in FIG. 61 by the right arm 346 contacting the raised edge 329 and by the left arm 344 contacting the raised edge 331. When the assembled cassette 302 is installed, movement of the latch jaw 340 to the position of FIG. 61 will also be limited by the presence of the piston assembly 280, with the rectangular base 282 being grasped by the jaws assembly 360. It will be noted that by moving the pin 354 either toward the front or toward the back, the latch jaw 340 may either be opened or closed, respectively.

Referring next to FIGS. 62 through 65, a main pump unit chassis 370 is illustrated which is designed to mount three independent pump units including three drive mechanisms into which three disposable assembled cassettes 302 may be installed. The assembled cassettes 302 are mounted on the bottom side of the pump chassis 370 shown in FIG. 62, with the motors and drive train being mounted on top of the pump chassis 370 (FIG. 64) and being installed in a housing (not shown) mounted on top of the pump chassis 370.

Located on the pump chassis 370 are three pairs of angled segments 372 and 374, 376 and 378, and 380 and 382. Each pair of angled segments 372 and 374, 376 and 378, and 380 and 382 defines two facing channels therebetween. In the preferred embodiment, the angled segments 372 and 374, 376 and 378, and 380 and 382 are angled slightly further from the bottom of the pump chassis 370 near the front, to thereby have a camming effect as the assembled cassette 302 is installed and the slide latch 240 is closed. Specifically, the angled segment 372 defines a channel facing the angled segment 374, and the angled segment 374 defines a channel facing the angled sement 372. The angled sement 376 defines a channel facing the angled segment 378, and the angled segment 378 defines a channel facing the angled segment 376. Finally, the angled segment 380 defines a channel facing the angled segment 382, and the angled segment 382 defines a channel facing the angled segment 380.

Each of the pairs of angled segments 372 and 374, 376 and 378, and 380 and 382 provides means on the bottom of pump chassis 370 for one assembled cassette 302 to be securely latched to. The inverted L-shaped portion 250 and the inverted, backwards L-shaped portion 252 in the slide latch 240 (FIGS. 29 and 30) of the assembled cassette 302 are designed to facilitate attachment to one of the pairs of angled segments 372 and 374, 376 and 378, and 380 and 382. With the slide latch 240 pulled back away from the front of the assembled cassette 302, an area between the front portion 242 of the slide latch 240 and the top front of the cassette body 100 and the retainer cap 190 is open, allowing the top of the assembled cassette 302 to be placed over one of the pairs of angled segments 372 and 374, 376 and 378, and 380 and 382.

Figure 62:
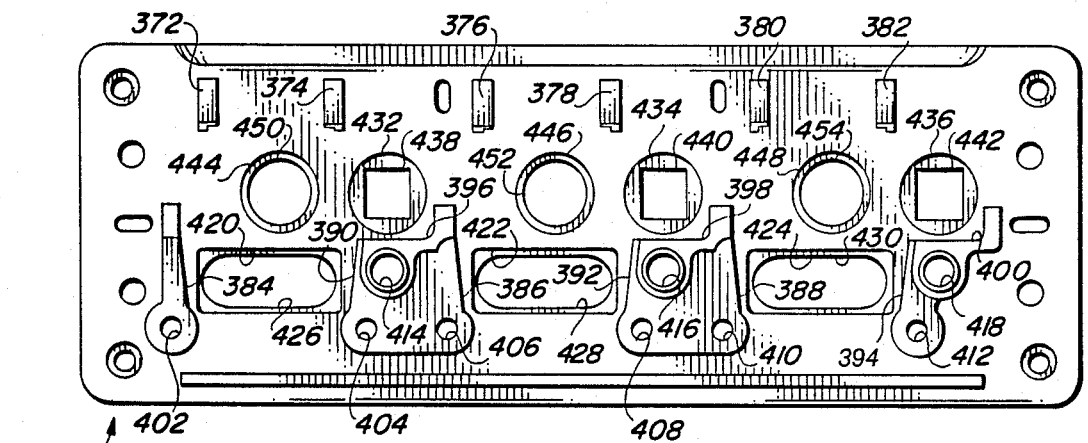
FIG. 62 is a bottom plan view of the main pump unit chassis.
Figure 65:
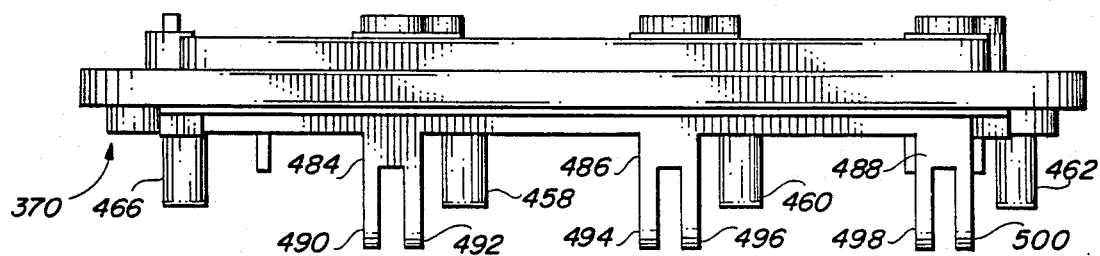
FIG. 65 is a back view of the main pump unit chassis shown in FIGS. 62 through 64.
Figure 71:
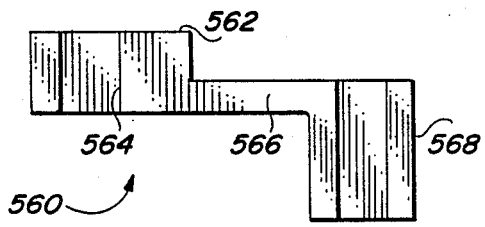
FIG. 71 is a right side view plan view of the slide lock used to retain the cassette shown in FIGS. 43 through 48 in position on the main pump unit.
Figure 72:
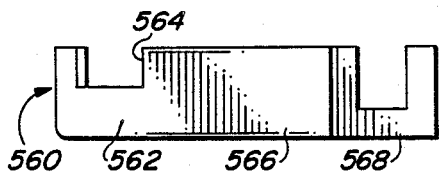
FIG. 72 is a bottom view of the slide lock shown in FIG. 71.
Figure 73:
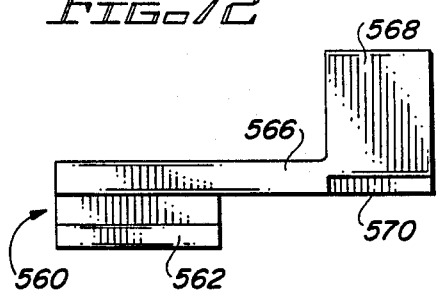
FIG. 73 is left side view of the slide lock shown in FIGS. 71 and 72, showing the bevel used to reflect the light beam from the optical light source away from the optical light sensor when the slide lock is in the open position.
Figure 74:
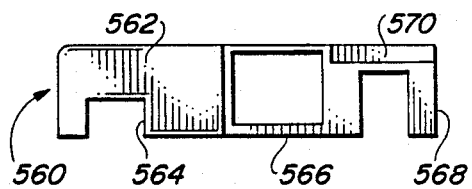
FIG. 74 is a top view of the slide lock shown in FIGS. 71 through 73, showing the reflective surface used to reflect the light beam from the optical light source to the optical light sensor when the slide lock is in the closed position.
Figure 75:
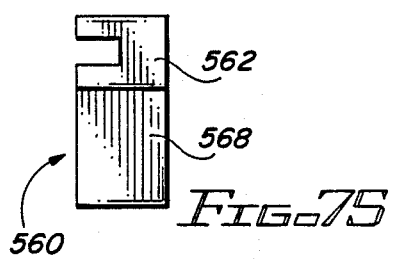
FIG. 75 is a front side view of the slide lock shown in FIGS. 71 through 74.

By way of example, assume that the assembled cassette 302 is to be mounted in the first position (the position on the left end of the pump chassis 370) on the first pair of angled segments 372 and 374. The top surface of the assembled cassette 302, which is the retainer cap 190 (FIG. 43), will mount against the bottom of the pump chassis 370 (FIG. 62). In order to place the assembled cassette 302 in condition to be installed, the slide latch 240 is pulled back fully from the front of the assembled cassette 302, leaving an area between the front portion 242 of the slide latch 240 and the front top portion of the assembled cassette 302 (made up of the cassette body 100 and the retainer cap 190) facing the front portion 242 of the slide latch 240.

The top of the assembled cassette 302 is then placed against the bottom of the pump chassis 370 with the first pair of angled segments 372 and 374 fitting in the area between the front portion 242 of the slide latch 240 and the front top portion of the assembled cassette 302. The slide latch 240 is then pushed forward into the cassette body 100, sliding the inverted L-shaped portion 250 of the slide latch 240 into engagement with the angled segment 372, and sliding the inverted, backwards L-shaped portion 252 of the slide latch 240 into engagement with the angled segment 374. The assembled cassette 302 will thus be held in position on the bottom of the pump chassis 370 until the slide latch 240 is again pulled back, releasing the assembled cassette 302.

Projecting from the bottom of the pump chassis 370 are a number of segments used to position and align the assembled cassettes 302 in the first (the position on the left end of the pump chassis 370), second (intermediate), and third (the position on the right end of the pump chassis 370) positions on the pump chassis 370. Three left lateral support walls 384, 386, and 388 protrude from the bottom of the pump chassis 370 at locations to support the upper left side portion of the assembled cassettes 302 near the back thereof in proper positions in the first, second, and third positions, respectively. Likewise, three right lateral support walls 390, 392, and 394 protrude from the bottom of the pump chassis 370 at locations to support the rear-most extending upper portion of the assembled cassettes 302 on the right side thereof in proper positions in the first, second, and third positions, respectively.

Additional support and positioning for the installation of the assembled cassettes 302 into the first, second, and third positions are provided for the upper right back corner of the assembled cassettes 302 by three right corner support walls 396, 398, and 400, respectively. The three right corner support walls 396, 398, and 400 are L-shaped when viewed from the bottom (FIG. 62), and support and position the back of the assembled cassettes 302 behind the pump cylinders 112 (FIG. 4) and a portion of the right side of the assembled cassettes 302 adjacent the pump cylinders 112. Note that the three right lateral support walls 390, 392, and 394 and the three right corner support walls 396, 398, and 400 together provide continuous support and positioning for the assembled cassettes 302 in the first, second, and third positions, respectively.

Located in the raised material forming the left lateral support wall 384 near the back thereof is a threaded aperture 402. A single segment of raised material forms the right lateral support wall 390, the right corner support wall 396, and the left lateral support wall 386; located in that segment of raised material near the back thereof is a threaded aperture 404 on the left side near the right lateral support wall 390, and a threaded aperture 406 on the right side near the left lateral support wall 386. Likewise, a single segment of raised material forms the right lateral support wall 392, the right corner support wall 398, and the left lateral support wall 388; located in that segment of raised material near the back thereof is a threaded aperture 408 on the left side near the right lateral support wall 392, and a threaded aperture 410 on the right side near the left lateral support wall 388. Finally, a single segment of raised material forms the right lateral support wall 394 and the right corner support wall 400 near the back thereof is a threaded aperture 412 near the right lateral support wall 394.

Located in the segment of raised material forming the right lateral support wall 390, the right corner support wall 396, and the left lateral support wall 386 near the corner where the right lateral support wall 390 and the right corner support wall 396 meet is an aperture 414 which extends through the pump chassis 370 from top to bottom. Located in the segment of raised material forming the right lateral support wall 392, the right corner support wall 398, and the left lateral support wall 388 near the corner where the right lateral support wall 392 and the right corner support wall 398 meet is an aperture 416 which extends through the pump chassis 370 from top to bottom. Located in the segment of raised material forming the right lateral support wall 394 and the right corner support wall 400 near the corner where the right lateral support wall 394 and the right corner support wall 400 meet is an aperture 418 which extends through the pump chassis 370 from top to bottom.

Note that with the assembled cassettes 302 positioned and mounted in the first, second, and third positions, the aperture 414, the aperture 416, and the aperture 418, respectively, will be directly back of the piston rods 292 of the assembled cassettes 302 (FIG. 46). The apertures 414, 416, and 418 will be used to mount the drive shafts connected to the jaws assembles 360 (FIGS. 59 through 61) used to drive the piston assembly 280.

Located between the left lateral support wall 384 and the right lateral support wall 390 is a longitudinal rectangular recess 420 in the bottom surface of the pump chassis 370. Similarly, located between the left lateral support wall 386 and the right lateral support wall 392 is a longitudinal rectangular recess 422 in the bottom surface of the pump chassis 370. Finally, located between the left lateral support wall 384 and the right lateral support wall 390 is a longitudinal rectangular recess 424 in the bottom surface of the pump chassis 370. While the rectangular recesses 420, 422, and 424 do not extend through the pump chassis 370, oval aperture 426, 428, and 430 smaller than the rectangular recesses 420, 422, and 424 are located in the rectangular recesses 420, 422, and 424, respectively, and extend through to the top side of the pump chassis 370.

The rectangular recesses 420, 422, and 424 will be used to mount sensor modules therein, and the oval aperture 426, 428, and 430 are to allow the wires from the sensor modules to extend through the pump chassis 370. Note that with the assembled cassettes 302 positioned and mounted in the first, second, and third positions, the rear-most extending upper portions of the assembled cassettes 302 will be located over the rectangular recesses 420, 422, and 424.

Located in front of the right corner support wall 396 is a circular recess 432 in the bottom surface of the pump chassis 370. Similarly, located in front of the right corner support wall 398 is a circular recess 434 in the bottom surface of the pump chassis 370. Finally, located in front of the right corner support wall 400 is a circular recess 436 in the bottom surface of the pump chassis 370. While the circular recesses 432, 434, and 436 do not extend through the pump chassis 370, square apertures 438, 440, and 442 smaller than the circular recesses 432, 434, and 436 are located in the circular recesses 432, 434, and 436, respectively, and extend through to the top side of the pump chassis 370.

The circular recesses 432, 434, and 436 will be used to mount valve actuator guides therein, and the cylindrical aperture 450, 452, and 454 are to allow valve actuators to extend through the pump chassis 370 and to orient the valve actuator guides. Note that with the assembled cassettes 302 positioned and mounted in the first, second, and third positions, the circular recess 432, the circular recess 434, and the circular recess 436, respectively, will correspond exactly with the locations of the domed portions 178 of the valve diaphragms 170 in the assembled cassettes 302 (FIG. 43).

Located to the left of the circular recess 432 and in front of the rectangular recess 420 is a circular recess 444 in the bottom surface of the pump chassis 370. Similarly, located to the left of the circular recess 434 and in front of the rectangular recess 422 is a circular recess 446 in the bottom surface of the pump chassis 370. Finally, located to the left of the circular recess 436 and in front of the rectangular recess 424 is a circular recess 448 in the bottom surface of the pump chassis 370. While the circular recesses 444, 446, and 448 do not extend through the pump chassis 370, cylindrical apertures 450, 452, and 454 of a smaller diameter than the circular recesses 444, 446, and 448 are located in the circular recesses 444, 446, and 448, respectively, and extend through to the top side of the pump chassis 370.

The circular recesses 444, 446, and 448 will be used to mount pressure transducers therein, and the cylindrical apertures 438, 440, and 442 are to allow wires from the pressure transducers to extend through the pump chassis 370. Note that with the assembled cassettes 302 positioned and mounted in the first, second, and third positions, the circular recess 444, the circular recess 446, and the circular recess 448, respectively, will correspond with the locations of the pressure diaphragms 182 of the valve diaphragms 170 in the assembled cassettes 302 (FIG. 43).

Projecting from the surface on the top side of the pump chassis 370 are a number of raised segments in which threaded apertures are located to support the drive assembly. A cylindrical raised segment 456 is located to the left of the cylindrical aperture 450 on the top side of the pump chassis 370. A laterally extending oval raised segment 458 is located between the square aperture 438 and the cylindrical aperture 452 on the top side of the pump chassis 370. A second laterally extending oval raised segment 460 is located between the square aperture 440 and the cylindrical aperture 454 on the top side of the pump chassis 370. A cylindrical raised segment 462 is located to the right of the square aperture 442 and is laterally aligned with the rear-most portions of the oval raised segments 458 and 460. Finally, a cylindrical raised segment 464 is located to the right of the square aperture 442 and is laterally aligned with the front-most portions of the oval raised segments 458 and 460.

Located in the cylindrical raised segment 456 is a threaded aperture 466. Located in the oval raised segment 458 is a threaded aperture 468 near the rear-most portion of the oval raised segment 458, a threaded aperture 470 near the front-most portion of the oval raised segment 458, and a threaded aperture 472 centrally located in the oval raised segment 458. Similarly, located in the oval raised segment 460 is a threaded aperture 474 near the rear-most portion of the oval raised segment 460, a threaded aperture 476 near the front-most portion of the oval raised segment 460, and a threaded aperture 478 centrally located in the oval raised segment 460. Located in the cylindrical raised segment 462 is a threaded aperture 480. Finally, located in the cylindrical raised segment 464 is a threaded aperture 482.

The apertures 414, 416, and 418 through the pump chassis 370 terminate in raised segments extending from the top surface of the pump chassis 370. A raised segment 484 is located around the opening of the aperture 414 on top of the pump chassis 370, a raised segment 486 is located around the opening of the aperture 416 on top of the pump chassis 370, and a raised segment 488 is located around the opening of the aperture 418 on top of the pump chassis 370.

Extending upwardly from the raised segment 484 behind the aperture 414 on the left side is a guide finger 490, and on the right side is a guide finger 492. The guide fingers 490 and 492 are parallel and have a space therebetween. Extending upwardly from the raised segment 486 behind the aperture 416 on the left side is a guide finger 494, and on the right side is a guide finger 496. The guide fingers 494 and 496 are parallel and have a space therebetween. Extending upwardly from the raised segment 488 behind the aperture 418 on the left side is a guide finger 498, and on the right side is a guide finger 500. The guide fingers 498 and 500 are parallel and have a space therebetween.

Referring now to FIGS. 66 through 69, a cassette guide 510 for use in guiding the installation of the assembled cassette 302 into the proper location for latching on the pump chassis 370 is illustrated. Disposed to the rear of the cassette guide 510 at the right side is an aperture 512, and at the left side is an aperture 514. The aperture 512 will be aligned with the threaded aperture 404 (FIG. 62), the threaded aperture 408, or the threaded aperture 412 while the aperture 514 will be aligned with the threaded aperture 402, the threaded aperture 406, or the threaded aperture 410 to install the cassette guide 510 in either the first, second, or third position.

The top side (FIG. 66) of the cassette guide 510 has a rectangular recess 516 therein, which rectangular recess 516 corresponds in size to the rectangular recesses 420, 422, and 424 in the pump chassis 370. The sensor modules will be accommodated between the rectangular recesses 516 in the cassette guides 510 and the rectangular recesses 420, 422, and 424 in the pump chassis 370. The right side of this rectangular recess 516 is exposed through a rectangular aperture 518 on the bottom of the cassette guide 510 (FIG. 67).

An area 520 on the bottom of the cassette guide 510 immediately to the front of the rectangular aperture 518 and an area 522 to the right and to the back of the rectangular aperture 518 is recessed upward from the bottom surface 524 of the cassette guide 510. At the front right corner of the rectangular aperture 518 a square segment 528 extends downward to the level of the bottom surface 524 of the cassette guide 510. Located immediately forward of the square segment 528 is a thin rectangular track 530 extending from the right side of the cassette guide 510. The thin rectangular track 530 terminates at the front end thereof in a blocking segment 532.

The front end of the cassette guide 510 has a rounded notch 534 therein, which rounded notch is positioned when the cassette guide 510 is installed on the pump chassis 370 to receive the outlet tube mounting cylinder 144 on the cassette body 100 (FIG. 4). When the cassette guide 510 is installed on the pump chassis 370, the rear-most portion of the assembled cassette 302 will fit between the cassette guide 510 and the bottom of the pump chassis 370. Accordingly, the cassette guide 510 together with the various support walls on the bottom of the pump chassis 370 aids in the installation of the assembled cassettes 302 in the proper position for latching.

Referring next to FIG. 70, a pump shaft 540 is illustrated which is essentially cylindrical. Near the top end of the pump shaft 540 on the front side thereof a cam follower wheel 542 is mounted for rotation about a short axle 544 extending orthogonally from the pump shaft 540. On the front side of the pump shaft 540 at the same location an alignment wheel 546 is mounted for rotation about a short axle 548 extending orthogonally from the pump shaft 540 on the opposite side of the short axle 544. Near the bottom end of the pump shaft 540 on the rear side thereof is a conical recess 550, which will be used to attach the jaws assembly 360 (FIG. 59 through 61) to the pump shaft 540.

Referring next to FIGS. 71 through 76, a slide lock 560 which is for mounting on the thin rectangular track 530 of the cassette guide 510 (FIG. 67) is illustrated. The slide lock 560 has a U-shaped slide channel 562 at the front thereof, with the open portion of the U facing left and extending from front to rear. The right side of the slide channel 562, which is the bottom of the U, has a rectangular notch 564 located near the front thereof, which notch 564 runs from the top to the bottom of the slide channel 562.

Extending back from the rear of the slide channel 562 at the bottom thereof is a thin rectangular connecting segment 566, which effectively extends from the leg of the U at the bottom of the slide channels 562. Attached at the rear end of the rectangular connecting segment 566 is a U-shaped channel 568 with the open portion of the U facing right and extending from top to bottom. The forward leg of the U of the U-shaped channel 568 is attached to the rectangular connecting segment 566 at the top of the U-shaped channel 568. It will be appreciated that the top surface of the rectangular connecting segment 566 and the top of the U-shaped channel 568 (which is U-shaped) are coplanar, and that the interior surface of the lowermost leg of the slide channel 562 is also coplanar.

Figure 76:
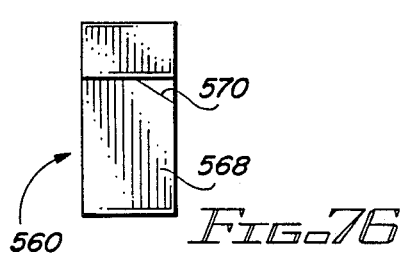
FIG. 76 is a back side view of the slide lock shown in FIGS. 71 through 75, showing the slanted surface used to reflect the light beam away from the corresponding sensor when the slide lock is in the open position.

The upper left edge of the U-shaped channel 568 has a bevel 570 located thereon, with the bevel 570 being best illustrated in FIG. 76. The function of the bevel 570 is as a light reflector, and will become apparent later in conjunction with the discussion of the mechanism for latching the assembled cassette 302.

Figure 77:
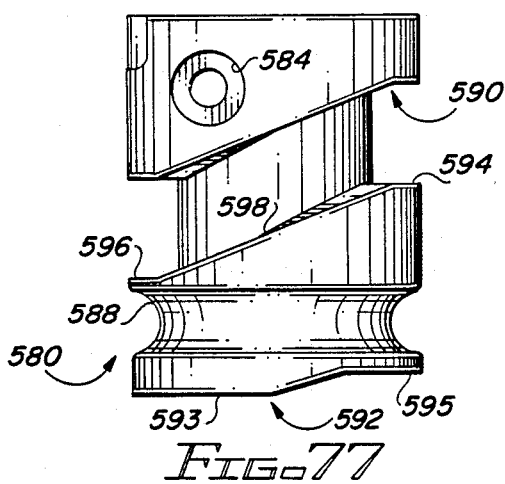
FIG. 77 is a side view of the power module cam used both to drive the pump through the pump shaft shown in FIG. 70 and to drive the valve actuators.
Figure 78:
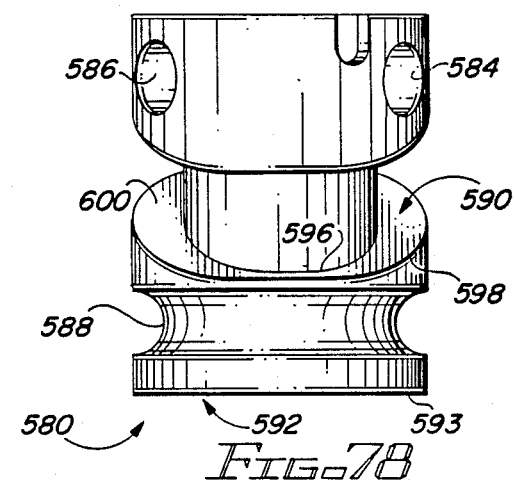
FIG. 78 is a side view of the power module cam rotated ninety degrees from the view of FIG. 77.
Figure 79:
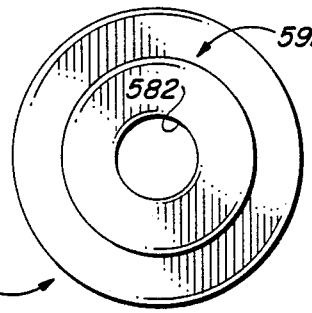
FIG. 79 is a bottom view of the power module cam shown in FIGS. 77 and 78.

Referring now to FIGS. 77 through 79, an essentially cylindrical power module cam 580 is illustrated. The power module cam 580 has an aperture 582 therethrough for mounting the power module cam 580 on a shaft (not shown), which the aperture 582 is shown from the bottom in FIG. 79. The power module cam 580 has aperture 584 and 586 through which means for retaining the power module cam 580 in position on a shaft may be installed. Located near to the bottom of the power module cam 580 is a groove 588 located around the outer circumference of the power module cam 580. The groove 588 will receive a drive belt which will drive the power module cam 580 is a rotary fashion.

Located above and spaced slightly away from the groove 588 in the power module cam 580 is a retaining groove indicated generally at 590 formed in the surface of and extending around the circumference of the power module cam 580. The retaining groove 590 is of essentially uniform width and depth in the surface of the power module cam 580, and varies in distance from the top side of the power module cam 580. As best seen in FIG. 77, the portion of the retaining groove 590 closest to the top of the power module cam 580 is disposed approximately one-hundred-eighty degrees away from the portion of the retaining groove 590 furthest from the top of the power module cam 580. It will be noted that a non-rotating member having a portion thereof engaged in the retaining groove 590 of the power module cam 580 will be driven in a reciprocating fashion as the power module cam 580 is turned.

Located on the bottom of the power module cam 580 about the outer diameter thereof is a cam surface indicated generally at 592. The cam surface 592 extends lower in one portion 593 than in the other portion 595, as best shown again in FIG. 77. It will be apparent to those skilled in the art that one or more non-rotating member bearing on the cam surface 592 will be driven in reciprocating fashion as the power module cam 580 is turned.

The configurations of the retaining groove 590 and the cam surface 592 are graphically illustrated in FIG.

80, which indicates how three members driven by the power module cam 580 are caused to operate as the power module cam 580 is rotated through a three-hundred-sixty degree cycle. The retaining groove 590 is used to drive a pump member, which draws fluid in from a source to fill the pump chamber on an intake stroke, and pumps the fluid out on a pumping stroke. The cam surface 592 is used to drive two valves members, namely an inlet valve and an outlet valve, which are driven by portions of the cam surface 592 which are separated by approximately one-hundred-eighty degrees. It will at once be appreciated that the pump and valves being driven will be those of the assembled cassette 302.

Figure 80:
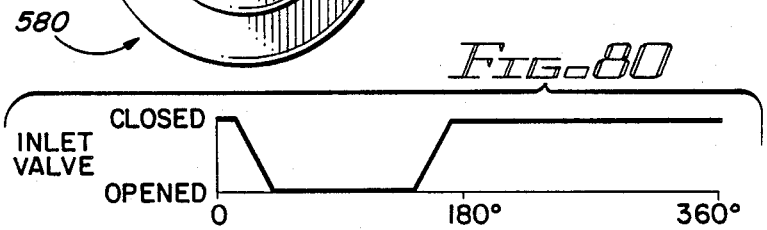
FIG. 80 is a chart of the inlet and outlet valve positions and the pump displacement versus angular position of the power module cam shown in FIGS. 77 through 79.

The plot of pump displacement in FIG. 80 illustrates that there is a fill cycle during which displacement increases from zero (or near zero) to full, and a pump cycle during which displacement decreases from full to empty (or near empty). The retaining groove 590 has two flat portions which correspond to the flat portions of the pump displacement plot. One of the flat portions 594 is the portion of the retaining groove 590 which is closest to the top thereof, and this flat portion 594 corresponds to the zero displacement portion of the pump displacement plot. The other flat portion 596 is the portion of the retaining groove 590 which is closest to the bottom thereof, and this flat portion 596 corresponds to the full displacement portion of the pump displacement plot.

The portions of the retaining groove 590 which are located intermediate the flat portions 594 and 596 are a positive portion 598 which corresponds to the increasing displacement portion of the pump displacement plot, and a negative portion 600 which corresponds to the decreasing displacement portion of the pump displacement plot. It should be noted that the flat portions 594 and 596 are substantial enough to allow valve movement entirely during the flat portions of the pump displacement plot. In the preferred embodiment, the flat portions 594 and 596 each represent approximately sixty degrees of rotational movement, while the positive and negative portions 598 and 600 each represent approximately one-hundred-twenty degrees of rotational movement.

The cam surface 592 of the power module cam 580 is described with reference to the inlet and outlet valve plots of FIG. 80. It will first be noted that the plots for the inlet and outlet valves are identical, but are located one-hundred-eighty degrees apart. As will become evident later in conjunction with the discussion of the valve actuators and the valve actuator guide, the inlet and outlet valves are both driven by the cam surface 592, but by points on the cam surface which are located one-hundred-eighty degrees apart.

The lower portion 593 of the cam surface 592 corresponds to the closed positions of both the inlet and outlet valves, while the higher portion 595 of the cam surface 592 corresponds to the opened positions of both the inlet and outlet valves. All valve movement is accomplished entirely during the periods in which pump displacement remains constant. In the preferred embodiment where pump displacement is constant during two sixty degree periods and either increasing or decreasing during two one-hundred-twenty degree periods, all valve movement is accomplished during the two sixty degree periods.

In addition, at least one valve is closed at any given time to prevent free flow through the assembled cassette 302. Therefore, it will be appreciated by those skilled in the art that the period during which the inlet and outlet valves transition between fully open and closed positions will be limited to thirty degrees or less in the preferred embodiment. During each of the sixty degree periods during which pump displacement is constant, the one of the valves which is open will close, and only then will the other valve, which was closed, be allowed to open.

Figure 81:
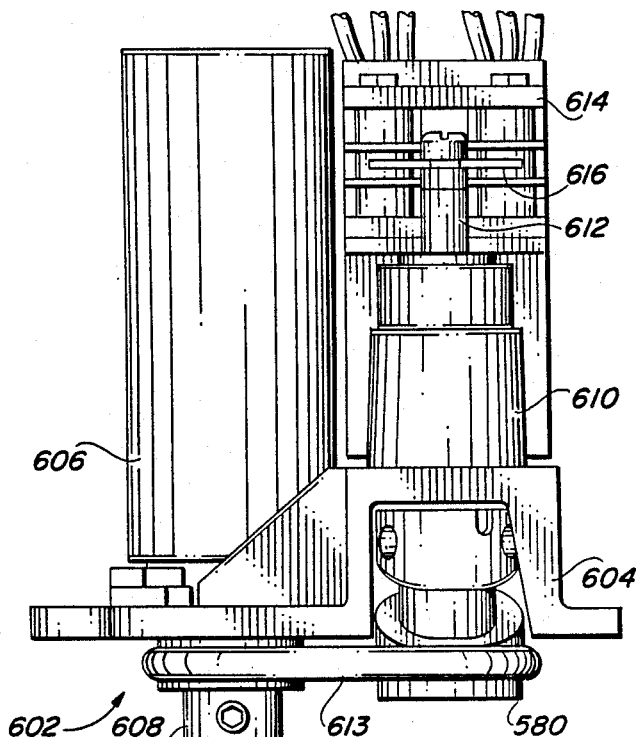
FIG. 81 is a plan view from the front side of the drive assembly including the motor/cam mount, the motor, the power module cam shown in FIGS. 77 through 79, and the position encoder assembly.
Figure 82:
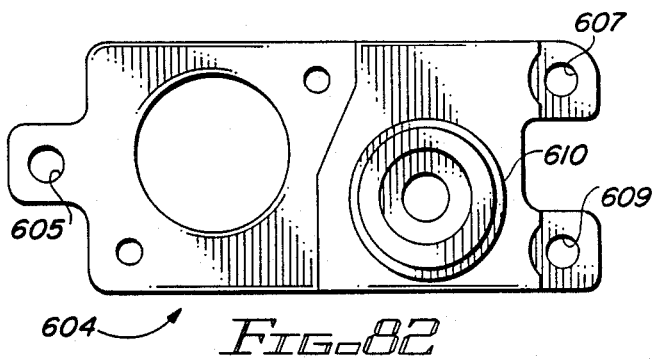
FIG. 82 is a top view of the motor/cam mount included in the drive assembly shown in FIG. 81.

Moving next to FIG. 81, a drive module assembly 602 is illustrated which includes the power module cam 580 discussed above. The various parts described in conjunction with FIG. 81 are mounted onto a drive module chassis 604, which will in turn be mounted onto one of the three pump positions on the top side of the pump chassis 370. As shown in FIG. 82, the drive module chassis 604 has an aperture 605 therethrough on the left side thereof, and two apertures 607 and 609 therethrough on the right side thereof. The apertures 605, 607, and 609 are for use in fastening the drive module assembly 602 to the pump chassis 370.

An ironless core DC motor 606 is used to drive the system. The motor 606 typically has a built-in gear reduction unit to reduce the output speed of the motor 606. The end of the motor 606 having the output shaft (not shown) is mounted onto the top of the drive module chassis 604 at one side thereof with the output shaft extending through the drive module chassis 604. A drive pulley 608 is mounted on the output shaft and is driven by the motor 606.

A one-way clutch 610 is mounted onto the top of the drive module chassis 604 at the other side thereof. Such devices are commercially available, and are also referred to as DC roller clutches or overrunning clutches. The one-way clutch 610 supports a drive shaft 612 for rotation therein; both ends of the drive shaft 612 extend from the one-way clutch 610. The one-way clutch 610 allows the drive shaft 612 to rotate in one direction only; in the preferred embodiment, the rotation is clockwise when viewed from the top. The power module cam 580 is mounted on the bottom end of the drive shaft 612 extending from the one-way clutch 610. A drive belt 613 is mounted over the drive pulley 608 and in the groove 588 in the power module cam 580. The motor 606 will thereby drive the power module cam 580 and the drive shaft 612.

Fixedly mounted above the one-way clutch 610 is an angular incremental position sensor 614. A sensor disk 616 is fixedly mounted on the top end of the drive shaft 612, and rotates with the drive shaft 612 and the power module cam 580. The position sensor 614 is used to provide angular incremental and absolute position feedback for control of the drive mechanism and cassette. In the preferred embodiment, the position sensor 614 should also be capable of direction sensing.

Figure 85:
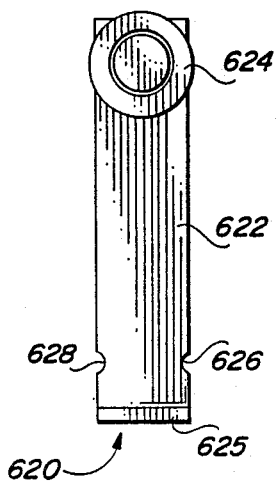
FIG. 85 is a side plan view of a valve actuator.
Figure 86:
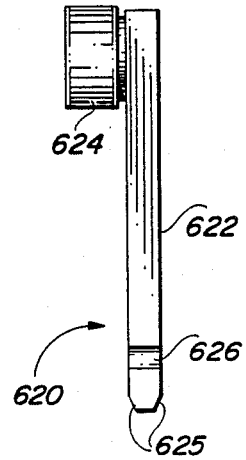
FIG. 86 is an side edge view of the valve actuator shown in FIG. 85.
Figure 87:
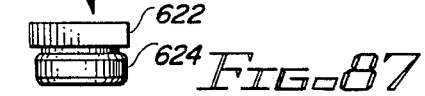
FIG. 87 is a bottom view of the valve actuator shown in FIGS. 85 and 86.

Referring next to FIGS. 85 through 87, a valve actuator 620 is illustrated which is driven by the power module cam 580 (FIGS. 77 through 79). The valve actuator 620 includes a thin, essentially rectangular portion 622, and has a circular bearing 624 rotatably mounted near the top thereof. The circular outer diameter of the bearing 624 extends slightly above the top of the rectangular portion 622. The bearing 624 is the portion of the valve actuator 620 which will be in contact with the cam surface 592 of the power module cam 580.

The rectangular portion 622 of the valve actuator 620 has chamfered edges on the lower end thereof as indicated generally at 625, and has a small notch 626, 628 in both lateral sides of the rectangular portion 622 at a location above the lower end thereof. The small notches 626 and 628 are for receiving means for retaining the valve actuator 620 in position once it is installed; this will become evident below in conjunction with the discussion of the assembly of the main pump unit.

Figure 83:
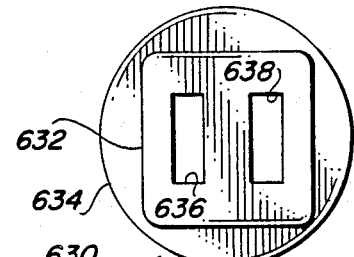
FIG. 83 is a top view of one of the actuator guides used to guide and retain in position the valve actuators for one cassette.
Figure 84:
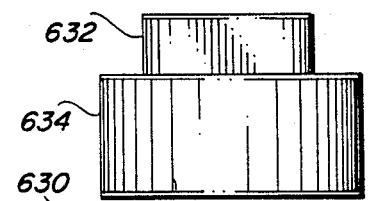
FIG. 84 is a side view of the actuator guide shown in FIG. 83.

Moving next to FIGS. 83 and 84, a valve actuator guide 630 is illustrated which is used to guide and retain in position pairs of the valve actuators 620. The upper portion 632 of the valve actuator guide 630 is square in cross-section, and lower portion 634 is circular in cross-section. Extending vertically through both the square upper portion 632 and the circular lower portion 634 of the valve actuator guide 630 are two apertures 636 and 638, which are rectangular in cross-section. The apertures 636 and 638 are sized to allow the rectangular portion 622 of the valve actuator 620 to slide freely therein in each of the apertures 636 and 638.

One of the valve actuator guides 630 will be installed into each of the pump positions in the pump chassis 370. In the first pump position, the square upper portion 632 of the valve actuator guide 630 will be located in the square aperture 438 on the pump chassis 370 and the circular lower portion 634 of the valve actuator guide 630 will be located in the circular recess 432 on the pump chassis 370. In the second pump position, the square upper portion 632 will be located in the square aperture 440 and the circular lower portion 634 will be located in the circular recess 434. In the third pump position, the square upper portion 632 will be located in the square aperture 442 and the circular lower portion 634 will be located in the circular recess 436.

Figure 88:
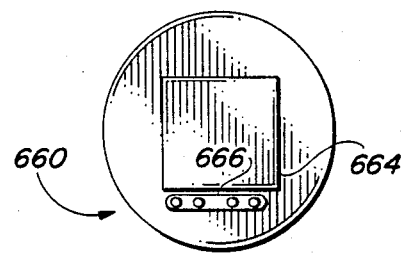
FIG. 88 is a top plan view of a pressure transducer.
Figure 89:
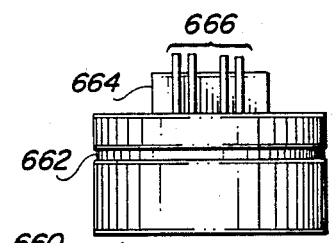
FIG. 89 is a side view of the pressure transducer shown in FIG. 88.
Figure 90:
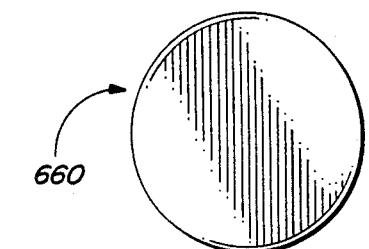
FIG. 90 is a bottom view of the pressure transducer shown in FIGS. 88 and 89.

Referring next to FIGS. 88 through 90, a pressure transducer 660 is illustrated. One of the pressure transducers 660 will be installed in the pump chassis 370 in each pump position, in the circular recesses 444, 446, and 448. The pressure transducer 660 is essentially cylindrical, with a groove 662 located around the circumference of the pressure transducer 660. The groove 662 is to receive an elastomeric O-ring, which will both retain the pressure transducers 660 in the circular recesses 444, 446, and 448, and provide a fluid seal. Located on top of the pressure transducer 660 is a square segment 664 in which is located the actual transducer, which square segment 664 will be received in the cylindrical apertures 450, 452, and 454. Extending upward from the square segment 664 are several leads 666.

Referring next to FIGS. 91 through 96, an optical sensor module 670 is illustrated. The optical sensor module 670 is essentially rectangular in cross-section, with a wider rectangular flange 672 on top of the rectangular portion, and an oval portion 674 above the rectangular flange 672. A flex cable 676 extends from the top of the oval portion 674. Located around the circumference of the oval portion 674 is a groove 678, which will receive an elastomeric O-ring, which will retain the oval portion 674 of the optical sensor modules 670 in the oval apertures 426, 428, or 430. The rectangular flange 672 of the optical sensor modules 670 will fit into the rectangular recesses 420, 422, or 424, in the first, second, or third pump positions, respectively.

The rectangular portion of the optical sensor module 670 has located in the front thereof and immediately under the rectangular flange 672 a notch indicated generally by 680, which notch 680 will receive the rearmost portion of the assembled cassette 302. The bottom of the rectangular portion of the optical sensor module 670 has an optical light source 682 and an optical light sensor 684 located thereon in locations near and equidistant from the right side thereof. The optical light source 682 and the optical light sensor 684 are used to detect when the slide lock 560 is in the closed position, as will be discussed below.

Located on the upper surface of the notch 680 in the optical sensor module 670 are three optical light sources 686, 688, and 690, which extend in a line from left to right on the upper surface of the notch 680. Located immediately below the three optical light sources 686, 688, and 690 on the lower surface of the notch 680 in the optical sensor module 670 near the right side thereof are three optical light sensors 692, 694, and 696, which also extend in a line from left to right on the lower surface of the notch 680. The three optical light sources 686, 688, and 690 and the three optical light sensors 692, 694, and 696 are used to provide the three cassette identification bits, as will be discussed below.

Also located on the lower surface of the notch 680 in the optical sensor module 670 toward the left side thereof is an optical light source 698. Located in front of the optical light source 698 is an optical light sensor 700. The optical light source 698 and the optical light sensor 700 are used to detect the presence (or absence) of an air bubble in the fluid line in the cassette. The location of the optical light source 698 and the optical light sensor 700 as illustrated in FIG. 96 is that of the preferred embodiment, and operation of that preferred embodiment as well as the configurations and operational descriptions of several alternate embodiments are discussed below.

Referring next to FIGS. 97 and 98, a valve actuator seal 650 is shown which is used both to provide a fluid seal and, more importantly, to retain the valve actuators 620 (FIGS. 85 through 87) in an upward position with their bearings 624 against the lower portion 593 of the power module cam 580. The outer circumference of the valve actuator seals 650 is of a size allowing them to be retained in a friction fit in the circular recesses 432, 434, and 436 below the valve actuator guides 630. A metal ring (not shown) may be molded into the outer diameter of the valve actuator seals 650 to better enable them to be better retained in the circular recesses 432, 434 and 436.

Two apertures 652 and 654, which are rectangular in configuration, are located in the valve actuator seal 650 to receive the bottom portions of the rectangular portion 622 of the valve actuator 620. The lengths of the apertures 652 and 654 are shorter than the width of the rectangular portion 622 of the valve actuator 620, with the small notches 626 and 628 in the rectangular portion 622 being used to capture to ends of one of the apertures 652 and 654. It will be appreciated that the small notches 626 and 628 of the valve actuators 620 will engage the apertures 652 and 654 in the valve actuator seal 650, thereby allowing the valve actuator seal 650 to exert a bias on the valve actuators 620. As will be seen below, the bias exerted by the valve actuator seal 650 on the valve actuators 620 is an upward one, urging the valve actuators 620 against the lower portion 593 of the power module cam 580.

In the previous discussions of the various parts of the main pump unit, the function and interrelationship between parts has been briefly discussed. Before moving on to the operation of the main pump unit and the assembled cassette 302, a brief discussion of the assembly of the main pump unit is in order. This discussion specifically refers to FIGS. 62 through 65 (the pump chassis 370), FIG. 99, and FIG. 112, and also to other figures which are specifically mentioned in the discussion.

A pump shaft bearing 640 is installed in both the top and the bottom of each of the apertures 414, 416, and 418 in the pump chassis 370. The pump shaft bearings 640 (FIG. 112) are essentially cylindrical and have a cylindrical aperture therethrough. In the preferred embodiment, the outer surface of the pump shaft bearings 640 have a raised portion or ridge 641 near the top thereof and fit in the apertures 414, 416, and 418 from the top and the bottom thereof in an interference fit to retain them in the apertures 414, 416, and 418 in the pump chassis 370. The pump shaft bearing 640 are preferably made of a low friction material such as Teflon to allow the pump shafts 540 to move freely therein. It will also be appreciated that a single bearing could be used in each of the apertures 414, 416, and 418 in the pump chassis 370 which bearing would extend all the way through the apertures 414, 416, and 418.

Next, the valve actuator guides 630 are installed from the bottom of the pump chassis 370 into the circular recess 432 and the square aperture 438 in the first pump position, into the circular recess 434 and the square aperture 440 in the second pump position, and into the circular recess 436 and the square aperture 442 in the third pump position. With the value actuator guides 630 installed in the pump chassis 370 the bottom surface of the valve actuator guides 630 leaves a portion of the circular recesses 432, 434, and 436 open from the bottom side of the pump chassis 370. The valve actuator seals 650 (FIGS. 97 and 98) will be installed later in the circular recesses 432, 434, and 436 below the valve actuator guides 630.

The next step in the assembly is to install the two sensor modules. The pressure transducers 660 (FIGS. 88 through 90) are installed from the bottom of the pump chassis 370 into the circular recesses 444, 446, and 448. The pressure transducers 660 are essentially cylindrical, and with O-rings in the grooves 662 fit snugly into the circular recesses 444, 446, and 448 with their bottom surfaces flush with the bottom surface of the pump chassis 370 around the circular recesses 444, 446, and 448; the tops of the cylindrical portion of the pressure transducers 660 fit against the cylindrical apertures 450, 452, and 454 in the pump chassis 370. Not shown in the drawings is the preferred embodiment's use of a thin membrane adhesively placed over the bottom of the pressure transducer 660 and the portions of the bottom surface of the pump chassis 370 thereabout. This thin membrane protects the pressure transducer 660 from fluids which may inadvertently or accidentally end up on the device.

The optical sensor assembles 570 (FIGS. 91 through 96) are installed in the rectangular recesses 420, 422, and 416 of the pump chassis 370, with the oval portions 674 of the optical sensor modules 670 fitting into the oval apertures 426, 428, and 430. The optical sensor modules 670 are retained in position by the pressure of O-rings in the grooves 678 in the optical sensor modules 670, and by the cassette guides 510.

The next step in the assembly of the main pump unit mechanical components onto the pump chassis 370 is the installation of the cassette guide 510 (FIGS. 66 through 69) and the slide lock 560 (FIGS. 71 through 76). The slide lock 560 is installed onto the cassette guide 510 by placing the portion of the slide lock 560 including the bottom of the slide channel 562 into the rectangular aperture 518 in the cassette guide 510 from the top, with the rectangular connecting segment 566 of the slide lock 560 extending over the portion of the area 522 in the back of the cassette guide 510. This aligns the interior of the U-shaped slide channel 562 on the slide lock 560 with the back end of the thin rectangular track 530 on the cassette guide 510. The slide lock 560 is then moved forward with respect to the cassette guide 510, with the interior of the slide channel 562 fitting over the thin rectangular track 530 until the blocking segment of the cassette guide 510 is contacted by the slide lock 560.

The cassette guides 510 together with the slide locks 560 may then be mounted into the three pump positions on the pump chassis 370, which already contain the optical sensor module 670, using two screws (not shown). In the first pump position, a screw is placed through the aperture 514 in the cassette guide 510 into the threaded aperture 402 in the pump chassis 370, and a second screw is placed through the aperture 512 in the cassette guide 510 into the threaded aperture 404 in the pump chassis 370. In the second pump position, a screw is placed through the aperture 514 in the cassette guide 510 into the threaded aperture 406 in the pump chassis 370, and a second screw is placed through the aperture 512 in the cassette guide 510 into the threaded aperture 408 in the pump chassis 370. In the third pump position, a screw is placed through the aperture 514 in the cassette guide 510 into the threaded aperture 410 in the pump chassis 370, and a second screw is placed through the aperture 512 in the cassette guide 510 into the threaded aperture 412 in the pump chassis 370. By way of example, the cassette guide 510 and the slide lock 560 are shown mounted in the first pump position in FIG. 99.

Next, the pump shafts 540 are installed in the pump shaft bearings 640, which have previously been installed in the apertures 414, 416, and 418. The end of the pump shafts 540 containing the conical recess 550 therein are inserted through the pump shaft bearings 640 from the top, with the alignment wheel 546 being located between one of the three pairs of guide fingers, namely the guide fingers 490 and 492 for the first pump position, the guide fingers 494 and 496 for the second pump position, and the guide fingers 494 and 496 for the third pump position. For example, the pump shaft 540 is shown installed in the first pump position in FIG. 112.

The valve actuators 620 are installed next, with one pair of the valve actuators 620 being installed in each pump position. The bottom ends of the valve actuators 620 having the chamfered edges 625 are inserted through the top sides of the valve actuator guides 630, with one pair of the valve actuators 620 being installed in each of the three valve actuator guides 630. The pair of valve actuators 620 are inserted into the apertures 636 and 638 in the valve actuator guides 630 with the bearings 624 on each of the pair of the valve actuators 620 facing away from each other.

It will be appreciated that the rectangular portions 622 of the valve actuators 620 will extend downward through the apertures 636 and 638 in the valve actuator guides 630. As stated above, valve actuator seals 650 are used in each of the three pump positions, and are mounted from the bottom of the pump chassis 370 into the circular recesses 432, 434, and 436 below the valve actuator guides 630. The outer circumference of the valve actuator seals 650 causes them to be retained in a friction fit in the circular recesses 432, 434, and 436.

The lower ends of the rectangular portions 622 of each pair of the valve actuators 620 extend downward through the apertures 652 and 654 in the valve actuator seal 650. The small notches 626 and 628 in one of the valve actuators 620 in each pair is retained in the aperture 652 in the valve actuator seal 650, and the other one of the valve actuators 620 in each pair is retained in the aperture 654. As shown in FIGS. 113 and 114, the valve actuator seals 650 will tend to urge the value actuators 620 in an upward direction. In the preferred embodiment, the bottoms of the valve actuators 620 having the chamfered edges 625 will protrude somewhat from the bottom surface of the pump chassis 370 around the circular recesses 432, 434, and 436 even when the valve actuators 620 are in their open position. For example, in their closed position they may protrude approximately thirty thousands of an inch, and in their open position they may protrude seventy thousands of an inch.

This upward biasing of the valve actuator 620 is essential both to allow the assembled cassettes 302 to be freely inserted, and to maintain the valve actuators 620 in an upward position with their bearings 624 against the lower portion 593 of the power module cam 580. The valve actuator seals 650 accordingly function both to provide a fluid seal and to bias the valve actuators 620 in the upward position described.

The next step in the assembly of the main pump unit is to install a drive module assembly 602 (FIG. 81) onto each of the three pump positions on the pump chassis 370. In the first pump position, the drive module assembly 602 will be supported above the top of the pump chassis 370 by the cylindrical raised segment 456 and the oval raised segment 458. Three screws (not shown) will be used to secure the drive module assembly 602 in the first pump position, with a first screw being placed through the aperture 605 in the drive module chassis 604 into the threaded aperture 466 in the pump chassis 370, a second screw being placed through the aperture 607 in the drive module chassis 604 into the threaded aperture 468 in the pump chassis 370, and a third screw being placed through the aperture 609 in the drive module chassis 604 into the threaded aperture 470 in the pump chassis 370. In the first pump position, the power module cam 580 is supported directly above the square aperture 438 in the pump chassis 370, and the valve actuator guide 630 and the two valve actuators 620 located in the first pump position.

In the second pump position, the drive module assembly 602 will be supported above the top of the pump chassis 370 by the oval raised segment 458 and the oval raised segment 460. Three screws (not shown) will be used to secure the drive module assembly 602 in the second pump position, with a first screw being placed through the aperture 605 in the drive module chassis 604 into the threaded aperture 472 in the pump chassis 370, a second screw being placed through the aperture 607 in the drive module chassis 604 into the threaded aperture 474 in the pump chassis 370, and a third screw being placed through the aperture 609 in the drive module chassis 604 into the threaded aperture 476 in the pump chassis 370. In the second pump position, the power module cam 580 is supported directly above the square aperture 440 in the pump chassis 370, and the valve acutator guide 630 and two valve actuators 620 located in the second pump position.

In the third pump position, the drive module assembly 602 will be supported above the top of the pump chassis 370 by the oval raised segment 460, the cylindrical raised segment 462, and the cylindrical raised segment 464. Three screws (not shown) will be used to secure the drive module assembly 602 in the third pump position, with a first screw being placed through the aperture 605 in the drive module chassis 604 into the threaded aperture 478 in the pump chassis 370, a second screw being placed through the aperture 607 in the drive module chassis 604 into the threaded aperture 480 in the pump chassis 370, and a third screw being placed through the aperture 609 in the drive module chassis 604 into the threaded aperture 482 in the pump chassis 370. In the third pump position, the power module cam 580 is supported directly above the square aperture 442 in the pump chassis 370, and the valve actuator guide 630 and the two valve actuators 620 located in the third pump position.

The final component to be installed is the jaws assembly 360 (FIGS. 59 through 61), with one jaws assembly 360 being installed in each of the three pump positions onto the bottom of the pump shafts 540, which are installed in the apertures 414, 416, and 418. The bottom end of the pump shaft 540 having the conical recess 550 therein is inserted into the cylindrical aperture 316 in the latch head 310 of the jaws assembly 360. A retaining screw (not shown) is screwed into the threaded aperture 318 in the latch head 310, and into the conical recess 550 of the pump shaft 540 to retain the jaws assembly 360 in place on the bottom of the pump chassis 370.

The location of the installed jaws assembly 360 is shown in FIG. 99, with the slide lock 560 and the latch jaw 340 in the open position. The link pin 354 on the latch jaw 340 is located in the U-shaped channel 568 of the slide lock 560, and movement of the slide lock 560 will accordingly cause the latch jaw 340 to move. When the slide lock 560 is fully forward, as shown in FIG. 99, the latch jaw 340 will be in the open position, with the jaw portion 343 of the latch jaw 340 away from the right jaw 314 of the latch head 310. When the slide lock 560 is pushed toward the back of the pump chassis 370, as shown in FIG. 100, the latch jaw 340 will be in the closed position, with the jaw portion 342 of the latch jaw 340 closely adjacent the right jaw 314 of the latch head 310.

This completes the discussion of the assembly of the main pump unit with three pump positions. It will, of course, be appreciated that the main pump unit may be constructed with different numbers of pump positions without departing from the spirit of the present invention. It is now appropriate to discuss the installation of the assembled cassette 302 into the first pump position, which is the subject of the above-identified application entitled "Cassette Loading and Latching Apparatus for a Medication Infusion System," and the operation of the device to pump fluid and to perform the other associated functions. The operations of the other two pump positions are identical to the operation of the first pump position described below.

With the slide latch 240 pulled back fully away from the front of the assembled cassette 302 (FIGS. 43 through 48), the wider portion of the elongated, tear-shaped aperture 258 in the slide latch 240 will close the outlet tube 306, preventing fluid from flowing through the assembled cassette 302. The inlet tube 304 is connected to a fluid source such as an IV bag (not shown), and the outlet tube 306 is connected to a fluid delivery device such as an injection set (not shown), the use of which is well known in the art. The slide latch 240 is opened, together with any other closures in the IV bag line, and fluid fills the lines, the assembled cassette 302, and the injection set. By tapping or shaking the assembled cassette 302 any residual air bubbles will flow out through the line. The slide latch 240 is then pulled back and the outlet tube 306 is closed, and the system is in a primed condition with the assembled cassette 302 ready to be installed onto the main pump unit.

When the slide latch 240 is pulled back, an opening is left between the front portion 242 of the slide latch 240 and the front top portion of the assembled cassette 302 (made up of the cassette body 100 and the retainer cap 190) facing the front portion 242 of the slide latch 240. By way of the example used herein where the assembled cassette 302 is to be mounted in the first position (the position on the left end of the pump chassis 370), the opening between the front portion 242 of the slide latch 240 and the front top portion of the assembled cassette 302 will admit the first pair of angled segments 372 and 374 as the assembled cassette 302 is installed. The top surface of the assembled cassette 302, which is the retainer cap 190 (FIG. 43), will mount against the bottom of the pump chassis 370 (FIG. 62).

Prior to installing the assembled cassette 302 into the main pump unit, the slide lock 560 must be fully forward with the latch jaw 340 opened away from the latch head 310, as mentioned previously and as shown in FIG. 99. In addition, the jaws assembly 360 should be in its fully upward position, which may be achieved by using the motor 606 to drive the power module cam 580 to cause the jaws assembly 360 to be driven to this position using the position sensor 614.

With the rear-most edge of the assembled cassette 302 tilted upward, the rear-most edge of the top of the assembled cassette 302 is then placed against the bottom of the pump chassis 370 between the pressure transducer 660 (mounted flush with the bottom of the pump chassis 370) and the top side of the cassette guide 510. The rear-most portion of the top of the assembled cassette 302 is slid toward the back of the pump chassis 370 into position between the left lateral support wall 384 on the left side thereof and the right lateral support walls 390 on the right side thereof, with most of the rear-most portion of the top of the assembled cassette 302 fitting into the notch 680 in the optical sensor module 670. The upper right back corner of the assembled cassette 302 is supported and positioned in the back of the assembled cassette 302 behind the pump cylinder 112 (FIG. 4) and on the portion of the right side of the assembled cassette 302 adjacent the pump cylinder 112 by the right corner support wall 396.

When the assembled cassette 302 is pushed fully back in place, the front of the assembled cassette 302 is tilted upward against the bottom of the pump chassis 370, with the first pair of angled segments 372 and 374 on the bottom of the pump chassis 370 fitting into the area between the front portion 242 of the slide latch 240 and the front top portion of the assembled cassette 302. The slide latch 240 may then be pushed into the cassette body 100, sliding the inverted L-shaped portion 250 of the slide latch 240 into engagement with the angled segment 372, and sliding the inverted, backwards L-shaped portion 252 of the slide latch 240 into engagement with the angled segment 374. The assembled cassette 302 will thus be held in position on the bottom of the pump chassis 370 until the slide latch 240 is again pulled back, releasing the assembled cassette 302.

Simultaneously, the outlet tube 306 will be opened, but fluid will not flow through the outlet tube 306 since at least one of the valve actuators 620 will be in its fully downward position at any given time, thereby preventing free flow through the assembled cassette 302 whenever the assembled cassette 302 is installed on the main pump unit. It will also be noted that in this initially installed position, the piston cap portion 262 is located at the very top of the pump cylinder 112.

It will be appreciated as discussed above that in the mechanical drive system of the present invention, the power module cam 580 will operate both the reciprocations of the piston assembly 280 and the movement of the valve actuators 620A and 620B (FIG. 112). The movement of the piston assembly 280 and the valve actuators 620A and 620B will correspond to the charts of FIG. 80, with the initially installed position corresponding roughly to the zero degree position of the charts. In this position, both the inlet valve actuator 620A and the outlet valve actuator 620B are in their closed positions.

Note that the open positions of the inlet valve actuator 620A and the outlet valve actuator 620B are their fully upward positions, and that their closed positions are their fully downward positions. Without the inlet valve actuator 620A and the outlet valve actuator 620B in place on the domed portion 178 of the valve diaphragm 170 of the assembled cassette 302, the area including the first passageway 128, the smaller diameter aperture 118 to the pump cylinder 112, and the second passageway 134 is entirely open and fluid flow therein is unrestricted. When the inlet valve actuator 620A is in its closed or fully downward position, the portion of the domed portion 178 located intermediate the first passageway 128 and the smaller diameter aperture 118 is forced down onto the portion of the slightly raised border 146 between the first passageway 128 and the smaller diameter aperture 118, thereby preventing fluid flow between the first passageway 128 and the smaller diameter aperture 118. This position of the inlet valve actuator 620A is referred to as its closed position.

Similarly, when the outlet valve actuator 620B is in its closed or fully downward position, the portion of the domed portion 178 located intermediate the smaller diameter aperture 118 and the second passageway 134 is forced down onto the portion of the slightly raised border 146 between the smaller diameter aperture 118 and the second passageway 134, thereby preventing fluid flow between the smaller diameter aperture 118 and the second passageway 134. This position of the outlet valve actuator 620B is referred to as its open position.

The motor 606 will begin to drive the power module cam 580, causing the inlet valve actuator 620A to open, with the outlet valve actuator 620B remaining closed, as shown in FIG. 113. As the power module cam 580 continues to be turned by the motor 606, the piston cap portion 262 will be drawn downward in the pump cylinder 112, causing fluid to be drawn into the pump cylinder 112 from the fluid source (not shown) through the inlet tube 304, the bubble trap 104, and the first passageway 128. When the pump cylinder 112 is filled, the inlet valve actuator 620A is closed. Only after the inlet valve actuator 620A is fully closed will the outlet valve actuator 620B be opened. FIG. 114 shows the system with the outlet valve actuator 620B opened, prior to any fluid being pumped out. The main pump unit responds to an electronic control system (not shown) which operates the system. This electronic control system, which is preferably microprocessor-based, may be either conventional as known in the art, or it may differ to enhance the unique mechanical design of the system discussed herein.

Fluid will be pumped by the motor 606 turning the power module cam 580 to drive the piston cap portion 262 upward in the cylinder, forcing fluid out of the pump cylinder 112, and eventually out of the assembled cassette 302 through the outlet tube 306, from which it is supplied to the patient through the injection set (not shown). It will be appreciated by those skilled in the art that the system may pump fluid at any rate chosen, by operating the motor 606 to pump fluid. In addition, the use of the position sensor 614 will provide a feedback signal indicating the exact position of the power module cam 580 and the piston assembly 280, thereby indicating how much fluid has been pumped by the device.

As noted previously, the rear-most portion of the assembled cassette 302 is located in the notch 680 of the optical sensor module 670 when the cassette is installed in the main pump unit. This is illustrated in FIGS. 101 and 102, which illustrate only the assembled cassette 302 and the optical sensor module 670. In some situations it may be desirable to use several different types of assembled cassettes 302 with the system described herein. For example, different cassettes may require different stroke volumes to provide different flow ranges, or require different fittings on the inlet tube 304 and/or the outlet tube 306 of the cassettes. Special application cassettes such as enteral pump cassettes, continuous arterio-venous hemofiltration (CAVH) cassettes, continuous blood sampling cassettes, or auto-transfusion cassettes may be manufactured.

The use of the wrong cassette may present a high degree of danger, so it will be perceived that it is highly desirable to identify the particular cassette installed. This may be accomplished by the use of the three cassette identifying indicia 148, 150, and 152. By making each of these indicia a binary bit, up to eight different codes may be generated. By using redundant coding to ensure fail-safe operation, three different cassettes can be identified. In addition, the absence of a cassette can also be detected. In the example illustrated in the drawings, the first cassette identifying indicia 148 and the third cassette identifying indicia 152 are of a first type (identified as a logical one for convenience), and the second cassette identifying indicia 150 is of a second type (identified as a logical zero for convenience).

With the assembled cassette 302 installed with its rear-most portion located in the notch 680 of the optical sensor module 670, the first cassette identifying indicia 148 is aligned with the first pair of sensor elements, namely the optical light source 686 and the optical light sensor 692. Similarly, the second cassette identifying indicia 150 is aligned with the second pair of sensor elements, namely the optical light source 688 ad the optical light sensor 694. Likewise, the third cassette identifying indicia 152 is aligned with the third pair of sensor elements, namely the optical light source 690 and the optical light sensor 696.

The second cassette identifying indicia 150 (the logical zero) and the second pair of sensor elements are shown in FIG. 103. Light from the optical light source 688 shines through the aperture 208 in the retainer cap 190, and onto the cassette body 100, where it is dispersed by the second cassette identifying indicia 150, which comprises an inverted V molded into the bottom of the upper surface 102 of the cassette body 100. Note that various prism types of construction could also be used to disperse the light, which does not reach the optical light sensor 694, resulting in a logical zero being output by the optical light sensor 694. For example, the inverted V could be molded into the top side of the upper surface 102 of the cassette body 100. Other alternatives include using paint or other physical blocking expedients instead of a dispersing lens, or selectively molding or not molding one or more of the apertures 206, 208, and 210 in the retainer cap 190 (FIGS. 13 and 14).

The third cassette identifying indicia 152 (the logical one, like the first cassette identifying indicia 148, which is not shown here) and the third pair of sensor elements are shown in FIG. 104. Light from the optical light source 690 shines through the aperture 210 in the retainer cap 190, and onto the third cassette identifying indicia 152 on the cassette body 100. The third cassette identifying indicia 152 is a cylindrical projection extending up from the upper surface 102 of the cassette body 100, which cylindrical projection acts like a light pipe to conduct the light to the optical light sensor 696, where it causes the optical light sensor 696 to generate a logical one output. Note that in the preferred embodiment, the cassette body 100 is constructed of clear plastic to allow the first cassette identifying indicia 148 and the third cassette identifying indicia 152 to conduct light therethrough. Also in the preferred embodiment, when there is no cassette 302 in place, all three outputs are logical ones, and this signal is used to indicate that no cassette has been installed or that the cassette 302 is improperly installed.

It will therefore be appreciated that the use of the three cassette identifying indicia 149, 150, and 152 allows the generation of three digital cassette identifying signals which are supplied from the optical sensor module 670 to the microprocessor (not shown) to identify the particular type of cassette which is installed. By using this cassette identifying system, inappropriate use of an installed cassette and/or improper cassette installation may be prevented.

It is desirable to provide an indication that the assembled cassette 302 has been properly installed on the main pump unit, with the latching mechanism properly closed. This occurs when the slide lock 560 is pushed fully back against the rear of the cassette guide 510. This is accomplished by sliding the slide latch 240 fully into the assembled cassette 302, with the tab 257 on the slide latch 240 fitting into the notch 564 on the slide lock 560 to drive the slide lock 560 back, thereby also latching the jaws assembly 360 onto the piston assembly 280.

Figure 107:
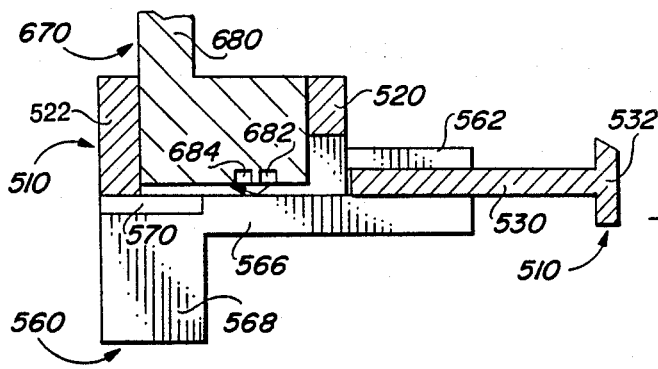
FIG. 107 is a cutaway view from FIG. 100 showing the slide lock in the closed position over the cassette-in-place sensor of the optical sensor module, with the light beam being reflected back onto the cassette-in-place sensor.

An indication of latching is provided through use of the optical light source 682 and the optical light sensor 684 on the bottom of the optical sensor module 670. When the slide lock 560 is in its loading or forward position shown in FIG. 99, the bevel 570 on the optical sensor module 670 is adjacent the optical light source 682 and the optical light sensor 684 on the bottom of the optical sensor module 670, as shown in FIGS. 105 and 106. The presence of the bevel 570 reflects the light coming from the optical light source 682 to the right, away from the optical light sensor 684, thereby preventing a latch closed signal. When the slide lock 560 is pushed fully back to its closed or rear-most position shown in FIG. 100, the bevel 570 on the optical sensor module 670 is not adjacent the optical light source 682 and the optical light sensor 684 on the bottom of the optical sensor module 670, as seen in FIG. 107. Rather, a reflective surface 567 installed on the flat bottom of the rectangular connecting segment 566 of the slide lock 560 reflects light from the optical light source 682 into the optical light sensor 684, thereby generating a latch closed signal. The reflective surface 567 acts as a mirror, and may be a foil segment which is, for example, hot stamped into the rectangular connecting segment 566 or adhesively secured to the bottom of the rectangular connecting segment 566.

Additional confirmation that the slide lock 560 was closed with an assembled cassette 302 in place may be obtained by verifying the cassette identifying indicia, as described above. In order to result in an absolutely positive confirmation that a cassette is properly installed and that the slide lock 560 is in the closed position, the preferred embodiment will require correct signals from both the optical light sensor 684, and from the optical light sensors 692, 694, and 696.

Figure 108:
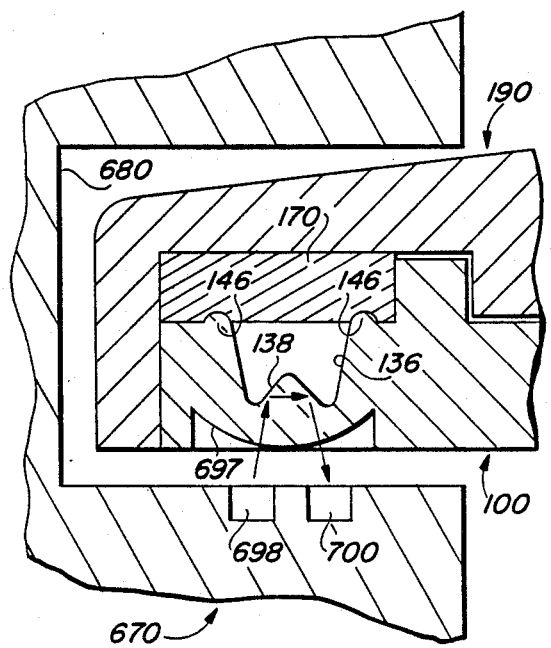
FIG. 108 is a third cutaway view of the cassette and the optical sensor module of FIGS. 101 and 102, showing the air-in-line detection apparatus of the preferred embodiment.

One of the essential functions of the system is to enable the detection of air in the fluid line of the system. The air-in-line detection (AILD) system of the preferred embodiment is shown in FIG. 108, and includes the recessed lens portion 138 in the assembled cassette 302, and a pair of sensor elements, namely the optical light source 698 and the optical light sensor 700 in the optical sensor module 670. The recessed lens portion 138 is an optical viewing area in the fluid pathway through the assembled cassette 302, and in the preferred embodiment shown in FIG. 108 is an inverted prism. The recessed lens portion 138 in any embodiment also includes a focusing lens, indicated generally at 697. The optical light source 698 and the optical light sensor 700 are both mounted in the optical sensor module 670 below the recesses prismatic lens portion 138 in the installed cassette 302.

The optics of the system of FIG. 108 makes use of the properties of light as it moves from one media to a less dense media, and is a "reverse reflected" configuration. When air is in the fluid channel, the light from the optical light source 698 follows the path shown in FIG. 108, reflecting off of one bottom side of the recessed prismatic lens portion 138 onto the other, and thence downward to the optical light sensor 700. Even if the upper surfaces of the recessed prismatic lens portion 138 are wetted with a fluid film, total internal reflection still occurs. When fluid is in the channel, the light refracts through the recessed prismatic lens portion 138 into the fluid. If the fluid is clear, the light passes through the liquid to 170, where it is either absorbed by the valve diaphragm 170 or the retainer cap 190, or passes through both the valve diaphragm 170 and the retainer cap 190. Accordingly, the valve diaphragm 170 may be clear, absorptive of light, or may scatter the light, not returning enough light to the optical light sensor 700 to generate a signal indicative of air being in the fluid path. If the valve diaphragm 170 is clear, then the retainer cap 190 may be clear, absorptive of light, or may scatter the light, again not returning enough light to the optical light sensor 700 to generate a signal indicative of air being in the fluid path. If the fluid is opaque, the light is absorbed by the fluid. In any event, the light does not return to the photodetector. What little reflection of light may occur will be small compared to the air case.

Material requirements of the preferred embodiment shown in FIG. 108 are that the cassette body 100 be made of clear material, that the valve diaphragm 170 be made of material which is clear, absorptive to light, or effectively scatters light. If the valve diaphragm 170 is clear, the retainer cap 190 must then be made of material which is clear, absorptive to light, or effectively scatters light. In summary, the fluid channel in the assembled cassette 302 is designed so that with the presence of air in the fluid channel, light sent by the optical light source 698 will be detected by the optical light sensor 700. With fluid contained in the fluid channel, little or no light will be detected, irrespective of the clarity or opaqueness of the fluid. It will therefore be appreciated by those skilled in the art that air bubbles in the line may be easily detected with the apparatus discussed above.

Figure 109:
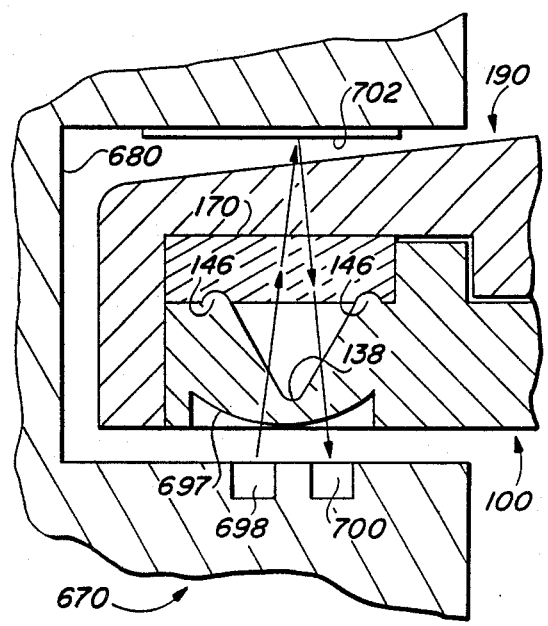
FIG. 109 is a cutaway view like FIG. 108, but showing a first alternate air-in-line detection apparatus.

There are three alternate embodiments to the arrangement illustrated in FIG. 108. First, in FIG. 109, a reflective surface 702 is installed on the side of the notch 680 in the optical sensor module 670 opposite the optical light source 698 and the optical light sensor 700. The recessed lens portion 138 in this embodiment is V-shaped, with light being directed from the bottom of the V. The materials of the cassette body 100, the valve diaphragm 170, and the retainer cap 190 are all clear. When a clear fluid is contained in the fluid pathway, light from the optical light source 698 will refract through to the reflective surface 702, and return to the optical light sensor 700, giving a high signal. When air is present in the fluid pathway, the light from the optical light source 698 will reflect off of the recessed lens portion 138 without passing therethrough, thereby not reaching the optical light sensor 700. However, when lipids are contained in the fluid pathway, the light will refract through the recessed lens portion 138 and be absorbed by the lipids, giving a signal indicative of air in the fluid pathway. It will thereby be appreciated that the arrangement shown in FIG. 109 is suitable for use with clear fluids only.

Figure 110:
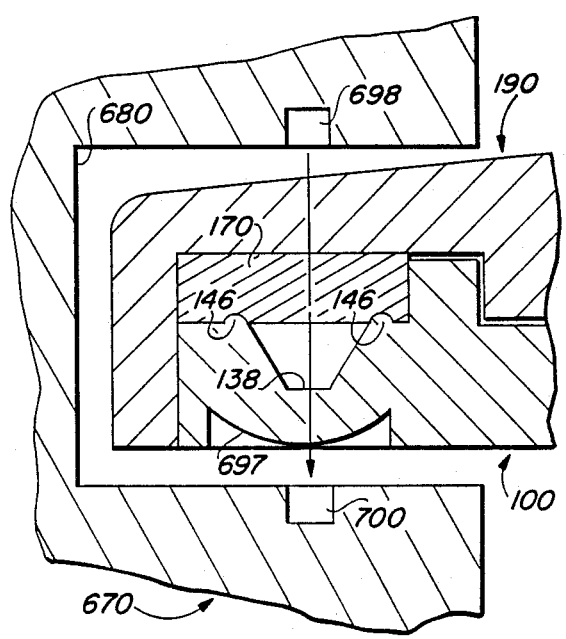
FIG. 110 is a cutaway view like FIG. 108, but showing a second alternate air-in-line detection apparatus.

Referring next to FIG. 110, a further variation is illustrated which uses a V-shaped channel, with the bottom of the V being flat. Light is directed from the optical light source 698, which is mounted on the top of the notch 680 in the optical sensor module 670, directly opposite the optical light sensor 700 on the bottom of the notch 680 in the optical sensor module 670. The materials of the cassette body 100, the valve diaphragm 170, and the retainer cap 190 are again clear. It will at once be appreciated that the signal received by the optical light sensor 700 will be low for lipids in the fluid pathway, and high for clear fluids in the fluid pathway. When air is present in the fluid pathway, some of the light will reflect off of the sides of the V, not reaching the optical light sensor 700, while some of the light will pass through the flat bottom of the V, reaching the optical light sensor 700. Therefore, for air a medium level signal will be received. The system of FIG. 110 is accordingly a three level system, and not digital.

Figure 111:
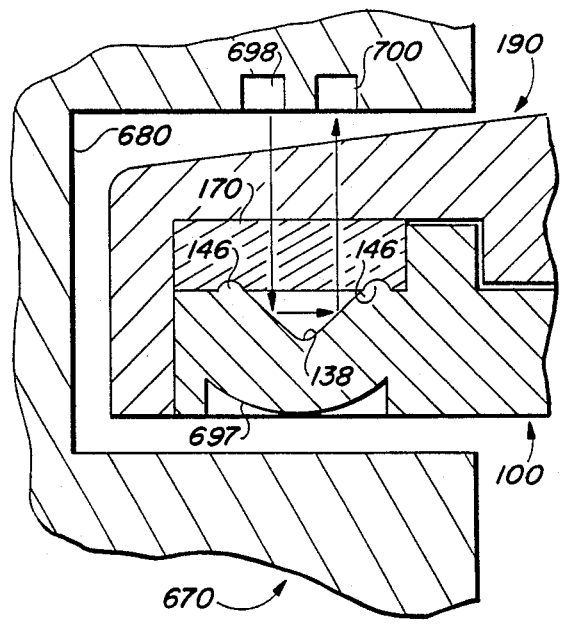
FIG. 111 is a cutaway view like FIG. 108, but showing a third alternate air-in-line detection apparatus.

Referring next to FIG. 111, a third variation is illustrated which uses a V-shaped recessed lens portion 138, with light being directed from the top of the V. In this embodiment, the optical light source 698 and the optical light sensor 700 are mounted on the top of the notch 680 in the optical sensor module 670, rather than on the bottom. The materials of the cassette body 100, the valve diaphragm 170, and the retainer cap 190 are again all clear. The signal received by the optical light sensor 700 will be high with air in the fluid pathway, low with clear liquids in the fluid pathway, and generally medium with lipids contained in the fluid pathway. The system of FIG. 111 is a three level system like the system of FIG. 110, but the optics of the system of FIG. 110 are superior to the optics of the system of FIG. 111.

Referring next to FIGS. 115 and 116, the operation of the pressure transducer system, which is the subject of the above-identified application entitled "Pressure Diaphragm for a Medication Infusion System," may be discussed. As may be seen, the pressure diaphragm 182 contacts the bottom of the pressure transducer 660, which is flat. Additionally, the pressure diaphragm 182 does not contact the pressure plateau 130 either on the top or on the sides thereof, making the movement of the pressure diaphragm 182 highly accurate and sensitive.

The pressure transducer 660 has a thin stainless steel diaphragm 710 at the bottom thereof. The diaphragm 710 is supported from the edges by a stainless steel housing 712, which housing 712 contains therein a passageway 714 leading to the square segment 664. The square segment 664 contains a sensor element (not shown in detail) communicating with the passageway 714, which sensor element is a standard silicon piezoresistive wheatstone bridge type device 716. The passageway 714 is filled with silicone oil to communicate pressure on the diaphragm 710 to the silicon piezoresistive wheatstone bridge type device 716.

It will be appreciated by those skilled in the art that the fluid pressure within the assembled cassette 302 will be communicated through the pressure diaphragm 182 and the diaphragm 710 to the silicone oil in the passageway 714, and thereby to the silicon piezoresistive wheatstone bridge type device 716, which provides an electrical indication of pressure on the leads 666. Accordingly, pressure may be measured to provide an indication of downstream occlusion, pumping, fluid pressure, etc.

Through the above discussion of the entire system, it will be appreciated that the drive system of the present invention utilizes a main pump unit which drives a reciprocating fluid pump having active inlet and outlet valves, with the pump and valves being contained in the disposable cassette. The system is highly sophisticated while mechanically uncomplex and inherently reliable. It is capable of driving a pump with a high degree of precision and accuracy, both of which remain constant throughout the extended operating life of the main pump unit.

Other additional features of the system include a simple and uncomplicated installation of the cassette onto the main pump unit, and a wide range in the volume which may be pumped by the system over a particular period of time. The valves and the pump are incapable of being operated out of synchrony; they are always properly and perfectly synchronized. Free flow through an installed cassette is impossible due to the construction and timing of the valve actuators. The valves in the cassette are placed in position to be driven by the drive system by merely installing the cassette with the valves in proximity to the drive mechanism. The drive system of the present invention is capable of varying the flow rate over a broad range while retaining a high degree of accuracy across the complete range of delivery rates. No other system currently known in the art has satisfactorily accomplished all of these objectives.

Despite the inclusion of more features than contained in any competing design, the drive system of the present invention utilizes a minimum number of parts, all of which parts are of inexpensive construction yet which afford a high degree of precision and accuracy in operation. The system accomplishes all these objects in a manner which retains all of the advantages of reliability, durability, and safety of operation. The drive system of the present invention provides all of these advantages and overcomes the limitations of the background art without incurring any relative disadvantage. All the advantages of the present invention result in a superior medication infusion system which represents a highly desirable alternative to systems presently available.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invenion.

What is claimed is:

1. A drive system for the main unit of a medication infusion system having a disposable cassette installable thereon, said disposable cassette including a reciprocating pump with inlet and outlet valves, said system comprising:
   a chassis, said disposable cassette for detachable mounting on one side of said chassis;
   a motor for driving said system, said motor being mounted onto said chassis;
   an essentially cylindrical power module cam rotatable driven by said motor, said power module cam being located on the other side of said chassis, one end of said power module cam facing said other side of said chassis;
   a continuous groove located in the side surface of and extending around said power module cam, said groove being of essentially uniform width and depth in the surface of said power module cam and varying in distance from said one end of said power module cam;
   means for driving said reciprocating pump in said disposable cassette, said driving means being mounted for reciprocal movement on said chassis, one end of said driving means being operably engaged with said groove in said power module cam, said driving means thereby being driven in a reciprocating direction by said power module cam as said power module cam is rotated by said motor;
   a washer-shaped cam surface on said one end of said power module cam, said cam surface varying in height around the periphery of said cam surface;
   an inlet valve actuator driven by said cam surface to open and close said inlet valve in said disposable cassette as said power module cam is turned by said motor; and
   an outlet valve actuator driven by said cam surface to open and close said outlet valve in said disposable cassette as said power module cam is turned by said motor.

2. A drive system as defined in claim 1, additionally comprising:
   means for receiving said disposable cassette in the proper position on said one side of said chassis, said receiving means aligning said reciprocating pump of said cassette with said driving means, said receiving means also aligning said inlet and outlet valves of said cassette with said inlet and outlet valve actuators, respectively.

3. A drive system as defined in claim 1, wherein said motor is an ironless core DC motor.

4. A drive system as defined in claim 1, additionally comprising:
- a gear reduction unit driven by said motor, said gear reduction unit for reducing the output speed of said motor; and
- a one-way clutch driven by said gear reduction unit, said one-way clutch supporting a drive shaft for rotation therein, said one-way clutch allowing said drive shaft to rotate in one direction only, said power module cam being mounted on one end of said drive shaft.

5. A drive system as defined in claim 4, additionally comprising:
- a drive pulley mounted on and driven by said gear reduction unit;
- a drive belt mounted over said drive pulley and in a circumferential drive groove located in said power module cam, and said motor thereby driving said power module cam and said drive shaft in said one direction when said motor is energized.

6. A drive system as defined in claim 4, additionally comprising:
- a sensor disk for an angular incremental position sensor mounted on the other end of said shaft, said sensor disk rotating with said drive shaft and said power module cam;
- an angular incremental position sensor fixedly mounted in position to monitor said sensor disk, said position sensor being used to provide angular incremental and absolute position feedback for control of the drive mechanism and cassette.

7. A drive system as defined in claim 6, wherein said position sensor is also capable of direction sensing.

8. A drive system as defined in claim 1, wherein the portion of said groove closest to said one end of said power module cam is essentially opposite the portion of said groove furthest away from said one end of said power module cam.

9. A drive system as defined in claim 1, wherein said groove being divided into first, second, third, and fourth consecutive portions around said power module cam, said first portion moving away from said one end of said power module cam as said first portion is traversed in the direction of rotation of said power module cam, said third portion moving toward said one end of said power module cam as said third portion is traversed in the direction of rotation of said power module cam, said second portion between said first and third portions being longitudinal around said power module cam, and said fourth portion between said third and first portions also being longitudinal around said power module cam.

10. A drive system as defined in claim 9, wherein said first and third portions each comprise approximately one-hundred-twenty degrees around said power module cam, and said second and fourth portions each comprise approximately sixty degrees around said power module cam.

11. A drive system as defined in claim 1, wherein said driving means comprises:
- a pump shaft mounted for reciprocal movement;
- means for connecting one end of said pump shaft to said reciprocation pump in said disposable cassette; and
- bearing means mounted at the other end of said pumpshaft for engagement in said groove in said power module cam.

12. A drive system as defined in claim 11, further comprising:
- means for inhibiting rotational movement of said pump shaft.

13. A drive system as defined in claim 12, wherein said inhibiting means comprises:
- two fingers extending from said other side of said chassis parallel to said pump shaft; and
- bearing means mounted on said pump shaft and located between said two fingers, said bearing means moving longitudinally between said two fingers when said pump shaft is reciprocating.

14. A drive system as defined in claim 1, wherein said inlet and outlet valve actuators are driven by portions of said cam surface which are approximately one-hundred-eighty degrees apart.

15. A drive system as defined in claim 1, wherein said washer-shaped cam surface is divided into first, second, third, and fourth consecutive portions around said washer-shaped cam surface, said first portion increasing in height over said one end of said power module cam as said first portion is traversed in the direction of rotation of said power module cam, said third portion decreasing in height over said one end of said power module cam as said third portion is traversed in the direction of rotation of said power module cam, said second portion between said first and third portions being at the maximum height above said power module cam, and said fourth portion between said third and first portions being at the minimum height above said power module cam.

16. A drive system as defined in claim 15, wherein said first and third portions each comprise approximately sixty degrees around said power module cam, and said second and fourth portions each comprise approximately one-hundred-twenty degrees around said power module cam.

17. A drive system for the main unit of a medication infusion system having a disposable cassette installable thereon, said disposable cassette including a reciprocating pump with inlet and outlet valves, said system comprising:
- a chassis, said disposable cassette for detachable mounting on one side of said chassis;
- an essentially cylindrical power module cam for rotatable motion, said power module cam being located on the other side of said chassis, one end of said power module cam facing said other side of said chassis;
- a motor for driving said power module cam, said motor being mounted onto said chassis;
- a continuous groove located in the side surface of and extending around said power module cam, said groove being of essentially uniform width and depth in th surface of said power module cam, said groove being divided into first, second, third, and fourth consecutive portions around said power module cam, said first portion moving away from said one end of said power module cam as said first portion is traversed in the direction of rotation of said power module cam, said third portion moving toward said one end of said power module cam as said third portion is traversed in the direction of rotation of said power module cam, said second portion between said first and third portions being longitudinal around said power module cam, and said fourth portion between said third and first portions also being longitudinal around said power module cam;

a pump shaft for driving said reciprocating pump in said disposable cassette, said pump shaft being mounted for reciprocal movement on said chassis, one end of said pump shaft being operably engaged with said groove in said power module cam, said pump shaft thereby being driven in a reciprocating direction by said power module cam as said power module cam is rotated by said motor;

a washer-shaped cam surface on said one end of said power module cam, said cam surface varying in height around the periphery of said cam surface;

an inlet valve actuator driven by said cam surface to open and close said inlet valve in said disposable cassette as said power module cam is turned by said motor; and an outlet valve actuator driven by said cam surface to open and close said outlet valve in said disposable cassette as said power module cam is turned by said motor, said inlet and outlet valve actuators being driven by portions of said cam surface which are approximately one-hundred-eighty degrees apart.

18. A drive system for the main unit of a medication infusion system having a disposable cassette installable thereon, said disposable cassette including a reciprocating pump with inlet and outlet valves, said system comprising:

a chassis, said disposable cassette for detachable mounting on one side of said chassis;

an essentially cylindrical power module cam for rotatable motion, said power module cam being located on the other side of said chassis, one end of said power module cam facing said disposable cassette;

first driving means for selectively driving said power module cam in rotational movement;

a continuous groove located in the side surface of and extending around said power module cam, said groove being of essentially uniform width and depth in the surface of said power module cam and varying in longitudinal position on said power module cam;

second driving means for driving said reciprocating pump in said disposable cassette in reciprocal movement, one end of said second driving means being operably engaged with said groove in said power module cam, said second driving means and said reciprocation pump being driven in reciprocating fashion by said power module cam as said power module cam is rotated by said first driving means;

a washer-shaped cam surface on said one end of said power module cam, said cam surface varying in height around the periphery of said cam surface; and inlet and outlet valve actuators driven by said cam surface to open and close said inlet and outlet valves in said disposable cassette as said power module cam is turned by said first driving means.

19. A method of driving the main unit of a medication infusion system having a disposable cassette installable thereon, said disposable cassette including a reciprocating pump with inlet and outlet valves, said method comprising:

rotatably driving an essentially cylindrical power module cam, one end of said power module cam facing said disposable cassette, said power module cam having a continuous groove located in the side surface thereof which groove extends around said power module cam, said groove being of essentially uniform width and depth in the surface of said power module cam and varying in distance from said one end of said power module cam;

driving said reciprocating pump in said disposable cassette with a pump shaft, one end of said pump being operably engaged with said groove in said power module cam, said driving means thereby being driven in a reciprocating direction by said power module cam as said power module cam is rotated by said motor;

driving an inlet valve actuator with a washer-shaped cam surface on said one end of said power module cam to open and close said inlet valve in said disposable cassette as said power module cam turns, said cam surface varying in height around the periphery of said cam surface; and driving an outlet valve actuator with said washer-shaped cam surface to open and close said valve in said disposable cassette as said power module cam turns.

* * * * *

UNITED STATES PATENT AND TRADEMARK OFFICE
CERTIFICATE OF CORRECTION

PATENT NO. : 4,850,817

DATED : July 25, 1989

INVENTOR(S) : Clyde K. Nason; John P. Pelmulder

It is certified that error appears in the above-indentified patent and that said Letters Patent is hereby corrected as shown below:

In Column 1, line 44, delete "small" and insert --smaller--;

In Column 1, line 60, delete "pums" and insert --pumps--;

In Column 2, line 24, delete "has" and insert --have--;

In Column 2, line 45, delete "it that they" and insert --that it--;

In Column 4, line 37, delete "operation" and insert --operating--;

In Column 5, line 62, delete "throug" and insert --through--;

In Column 7, line 50, delete "an" and insert --a--;

In Column 8, line 3, delete "indentification" and insert --identification--;

In Column 9, line 19, delete "in" and insert --is--;

In Column 10, line 16, delete "of the";

In Column 10, line 20, delete "with" and insert --which--;

UNITED STATES PATENT AND TRADEMARK OFFICE
CERTIFICATE OF CORRECTION

PATENT NO. : 4,850,817
DATED : July 25, 1989
INVENTOR(S) : Clyde K. Nason; John P. Pelmulder It is certified that error appears in the above-indentified patent and that said Letters Patent is hereby corrected as shown below:

In Column 11, line 34, delete "the";

In Column 15, line 44, delete "disclosd" and insert --disclosed--;

In Column 17, line 12, delete "Telfton" and insert --Teflon--;

In Column 17, line 47, insert --cap-- after "piston";

In Column 18, line 32, delete "locally" and insert --located--;

In Column 21, line 25, delete "corner" and insert --center--;

In Column 23, line 11, delete "sement" and insert --segment--;

In Column 25, line 5, delete "assembles" and insert --assembly--;

In Column 28, line 11, delete "end" and insert --edge--;

In Column 28, line 34, delete "aperture" and insert --apertures--;

In Column 28, line 40, delete "is" and insert --in--;

In Column 29, line 8, delete "valves" and insert --valve--;

In Column 30, line 7, delete the first occurrence of "the";

In Column 35, line 7, delete "value" and insert --valve--;

In Column 36, line 36, delete "343" and insert --342--;

In Column 39, line 54, delete "ad" and insert --and--;

UNITED STATES PATENT AND TRADEMARK OFFICE
CERTIFICATE OF CORRECTION

PATENT NO. : 4,850,817
DATED : July 25, 1989
INVENTOR(S) : Clyde K. Nason; John P. Pelmulder It is certified that error appears in the above-indentified patent and that said Letters Patent is hereby corrected as shown below:

In Column 40, line 32, delete "149" and insert --148--;

In Column 41, line 32, delete "recesses" and insert --recessed--;

In Column 46, line 56, delete "th" and insert --the--;

In Column 48, line 23, delete "side" and insert --said--;

In Column 48, line 43, insert --outlet-- after "said".

Signed and Sealed this

Twenty-fifth Day of October, 1994

Attest:

BRUCE LEHMAN

*Attesting Officer*  *Commissioner of Patents and Trademarks*